United States Patent [19]
Chao

[11] Patent Number: 5,911,982
[45] Date of Patent: Jun. 15, 1999

[54] HZ-1 VIRUS PERSISTENCE-ASSOCIATED-GENE 1 (PAG1) PROMOTER USES THEREFOR, AND COMPOSITIONS CONTAINING SAME OR PRODUCTS THEREFROM

[75] Inventor: Yu-Chan Chao, Taipei, Taiwan

[73] Assignee: National Science Council, Taipei, Taiwan

[21] Appl. No.: 08/634,350

[22] Filed: Apr. 18, 1996

Related U.S. Application Data

[60] Provisional application No. 60/004,894, Oct. 6, 1995, and provisional application No. 60/005,128, Oct. 11, 1995.

[51] Int. Cl.[6] .......................... A61K 31/70; C12P 21/00; C12N 5/06; C12N 15/64

[52] U.S. Cl. ................. 424/93.2; 435/69.1; 435/320.1; 435/348; 536/24.1

[58] Field of Search ............................. 424/93.6, 204.1, 424/DIG. 8, 93.2; 435/5, 69.1, 91.4, 235.1, 240.1, 320.1, 348; 536/23.1, 24.1

[56] References Cited

U.S. PATENT DOCUMENTS

| | | | |
|---|---|---|---|
| 5,162,222 | 11/1992 | Guarino et al. | 438/348 |
| 5,169,784 | 12/1992 | Summers et al. | 435/320.1 |

OTHER PUBLICATIONS

Chao, et al.. Differential expression of Hz–1 Baculovirus genes during productive and persistent viral infections. J. Virol.. vol. 66(3):1442–1448, Mar. 31, 1992.

Boyce and Bucher. Baculovirus–mediated gene transfer into mammalian cells, PNAS (USA). 93(6):3248–2352, Mar. 31, 1996.

Askew, D. S., J. Li, and J. N. Ihle. 1994. Retroviral insertions in the murine His–1 locus activate the expression of a novel RNA that lacks an extensive open reading frame. Mol. Cell. Biol. 14: 1743–1751.

Block, T. M., J. G. Spivack, I. Steiner, S. Deshmane, M. T. McIntosh, R. P. Lirette, and N. W. Fraser. 1990. A herpes simplex virus type 1 latency–associated transcript mutant reactivates with normal kinetics from latent infection. J. Virol. 64: 3417–3426.

Brannan, C. I., E. C. Dees, and S. W. M. Brown. 1990. The product of the H19 gene may functional as an RNA. Mol. Cell. Biol. 10: 28–36.

Brockdorff, N., A. Ashworth, F. K. Graham, V. M. McCabe, D. P. Norris, P. J. Cooper, S. Swift, and S. Rastan. 1992. The product of the mouse Xist gene is a 15 kb inactive X–specific transcript containing no conserved ORF and located in the nucleus. Cell 71: 515–526.

(List continued on next page.)

*Primary Examiner*—David Guzo
*Assistant Examiner*—William Sandals
*Attorney, Agent, or Firm*—Curtis, Morris & Safford, P.C.

[57] ABSTRACT

Disclosed and claimed is the promoter, full-length or truncated, of the persistence-associated gene 1 (pag1) of Hz-1 virus, vectors containing the promoter, including with exogenous coding DNA, methods employing the vectors, compositions employing the vectors and products therefrom, and probes and primers for the promoter or functional fragment thereof. The promoter of pag1 gene is strong and if not comparable, it is better than the promoter activity demonstrated in the polyhedrin gene in insect cells. In addition, the pag1 promoter can be expressed more prominently as a short promoter. The pag1 promoter can also be expressed in transient transfected and permanently transfected cells. Further, the pag1 promoter can also be expressed when it is inserted into other viruses, such as *Autographa californica* nuclear polyhedrosis virus. The pag1 promoter has also been shown to express foreign genes strongly, such as in lacZ and luciferase. pag1 is driven by a constitutively expressed early type promoter, thus facilitating expression much earlier than the polyhedrin gene promoter.

19 Claims, 24 Drawing Sheets

OTHER PUBLICATIONS

Brown, C. J. B. D. Hendrich, J. L. Rupert, R. G. Lafreniere, Y. Xing, J. Lawrence, and H. F. Willard. 1992. The human XIST gene: Analysis of a 17 kb inactive X–specific RNA that contains conserved repeats and is highly localized within the nucleus. Cell 71: 527–542.

Calzone, F. J., J. J. Lee, R. J. Britten, and E. H. Davidson. 1988. A Long, nontranslatable poly(A) RNA stored in the egg of the sea urchin *Stronglyocentrotus purpuratus*. Genes & Devel. 2: 305–318.

Chao, Y.–C. and Wood, H. A. 1990. The physical map of Hz–1 Baculovirus genome from standard and defective interference viral particles. J. of Gen. Virol. 71: 1265–1270.

Chao, Y.–C., Wood, H. A., Chang, C. Y., Lee, H. T., and Lee, H. R. 1992. Differential Gene Expressions of Hz–1 Baculovirus During Viral Productive and Persistent Infections. J. Virol. 66: 1442–1448.

Chen, E. Y. and P. H. Seeburg, 1985. Supercoil sequencing: a fast and simple method for sequencing plasmid DNA. DNA 4: 165–170.

Costantini, F. D., R. J. Britten, and E. H. Davidson. 1980. Message sequences and short repetitive sequences are interspersed in sea urchin egg poly(A)+ RNAs. Nature 287: 111–117.

Dobson, A. T., F. Sederati, G. Devi–Rao, W. M. Flanagan, M. J. Farrell, J. G. Stevens, E. K. Wagner, and L. T. Feldman. 1989. Identification of the latency–associated transcript promoter by expression of rabbit beta–globin MRNA in mouse sensory nerve ganglia latently infected with a recombinant herpes simplex virus. J. Virol. 63: 3844–3851.

Fini,M. E., W. G. Bendena, M. L. Pardue. 1989. Unusual behavior of the cytoplasmic transcript of hsr omega: An abundant, stress–inducible RNA that is translated but yields no detectable protein product. J. Cell Biol. 108: 2045–2057.

Fritz, J. D., M. L. Greaser, and J. A. Wolff. 1991. A novel 3' extension technique using random primers in RNA–PCR. Nucl. Acids Res. 19: 3747.

Guarino, L. A., Smith, G., and Dong. W. 1995. Ubiquitin is attached to membranes of Baculovirus particles by a novel type of phosphokipid anchor. Cell 80: 301–309.

Henikoff, S. 1984. Unidirectional digestion with exonuclease III creates targeted breakpoints for DNA sequencing. Gene 28: 351–359.

Hills, D., and Crane–Robinson, C. 1995. Baculovirus expression of human basic fibroblast growth factor from a synthetic gene: role of the Kozak consensus and comparison with bacterial expression. Biochim. Biophys. Acta 1260: 14–20.

Hink, W. F. 1970. Established insect cell line from the cabbage looper, *Trichoplusia ni*. Nature 226: 466–467.

Ho, D. Y., and E. S. Mocarski. 1989. Herpes simplex virus latent RNA (LAT) is not required for latent infection in the mouse. Proc. Natl. Acad. Sci. USA 86: 7596–7600.

Hughes, D. S., R. D. Possee, and L. A. King. 1993. Activation and detection of a latent Baculovirus resembling *Mamestra brassicae* nuclear polyhedrosis virus in *M. brassicae* insects. Virology 194: 608–615.

Jacks, T., and H. E. Varmus. 1985. Expression of the Rous sarcoma virus pol gene by ribosomal framshifting. Science 230: 1237–1242.

Kay, G. F., G. D. Penny, D. Patel, A. Ashworth, M. Brockdorff, and S. Rastan. 1993. Expression of Xist during mouse development suggests a role in the initiation of X chromosome inactivation. Cell 72: 171–182.

Kimelman, D., M. W. Kirschner. 1989. An antisense MRNA directs the covalent modification of the transcript encoding fibroblast growth factor in Xenopus oocyte. Cell 59: 687–696.

Klein, G. 1989. Viral latency and transformation: the strategy of Epstein–Barr virus. Cell 58: 5–8.

Laakkonen, P., Hyvonen, M., Peranen, J., and Kaariainen, L. 1994. Expression of Semliki Forest virus nsP1–specific methyltransferase in insect cells and in *Escherichia coli*. J. Virol. 68: 7418–7425.

Lee, J. C., H. H. Chen, H. L. Wei, and Y. C. Chao. 1993. Superinfection–induced apoptosis and its correlation with the reduction of viral progeny in cells persistently infected with Hz–1 Baculovirus. J. Virol. 67: 6989–6994.

Lee, S. T., S. M. Yu, E. L. Hsu, and Y. C. Chao. 1995. Identification of a very early promoter of insect of Hz–1 virus using a novel dual–expression shuttle vector. Nucleic Acids Res. 23: 4683–4689.

Lee, S. E. and G. Brawerman. 1971. Pulse labelled ribonucleic acid complexes released by dissociation of rat liver polysomes. Biochemistry 10: 510–516.

Leib, D. A., C. L. Bogard, M. Kosz–Vnenchak, K. A. Hicks, D. M. Coen, D. M. Knipe, and P. A. Schaffer. 1989. A deletion mutant of the latency–associated transcript of herpes simplex virus type 1 reactivates from the latent state with reduced frequency. J. Virol. 63: 2893–2900.

Liebovitch, M. P., V. C. Nguyen, M. S. Gross, B. Solhonne, S. A. Liebovitch, and A. Bernheim. 1991. The human ASM (adult skeletal muscle) gene: expression and chromosomal assignment to 11p15. Biochem. Biophys. Res. Commun. 180: 1241–1250.

Metzenberg, S. 1990. Levels of Epstein–Barr virus DNA in Lymphoblastoid cell lines are correlated with frequencies of spontaneous lytic growth but not with levels of expression of EBNA–1, EBNA–2, or latent membranes protein. J. Virol. 64: 437–444.

Nowak, R. 1994. Mining reasures from junk DNA. Science 263: 608–610.

Poirier, F., C. T. J. Chan, P. M. Timmons, E. J. Robertson, M. J. Evans, and P. W. J. Rigby. 1991. The murine H19 gene is activated during embryonic stem cell differentiation in vitro and at the time of implantation in the developing embryo. Development 113: 1105–1114.

Powell, L. M., S. C. Wallis, R. J. Pease, Y. H. Edwards, T. J. Knott, and J. Scott. 1987. A novel form of tissue–specific RNA processing produces apolipoprotein–B48 in intestine. Cell 50: 831–840.

Schmidt, E. E., and G. F. Merrill. 1991 Changes in dihydrofolate reductase (DHFR) MRNA levels can account fully for changes in DHFR synthesis rates during terminal differentiation in a highly amplified myogenic cell line. Mol. Cell. Biol. 11: 3726–3734.

Smith, G. S., Summers, M. D., and Fraser, M. J. 1983. Production of human beta interferon in insect cells infected with a Baculovirus expression vector. Mol. Cell. Biol. 3: 2156–2165.

Spivack, J., and N. W. Fraser. 1987. Detection of herpes simplex virus type 1 transcripts during latent infection in mice. J. Virol. 61: 3841–3847.

Steiner, I., J. G. Spivack, R. P. Lirette, S. M. Brown, A. R. McLean, J. H. Subak–Sharpe, and N. W. Fraser. 1989. Herpes simplex virus type 1 latency associated transcripts are evidently not essential for latent infection. EMBO J. 8: 505–511.

Stevens, J. G., E. K. Wagner, G. B. Devi–Rao, M. L. Cook, and L. T. Feldman. 1987. RNA complementary to a herpesvirus gene MRNA is prominent in latently infected neurons. Science 235: 1056–1059.

Tabor, S., and C. C. Richardson. 1987. DNA sequence analysis with a modified bacteriophage T7 DNA polymerase. Proc. Natl. Acad. Sci. U.S.A. 84: 4767–4771.

Takayama, K. M., and M. Inouye. 1990. Antisense RNA, Crit. Rev. Biochem. 25:155–184.

Volkman, L. E. 1995. Virus Taxonomy: the classification and nomenclature of viruses. In The sixth report of the ICTV. Springer–Verlag, Vienna. In press.

Wilson, M. 1991. The family and groups of Baculoviridae. In Classification and nonenclature of viruses. Fifth report of the International Committee on Taxonomy of Viruses. Archives of Virology Supplementum 2. pp. 117–123. Francki, R. I. B., Fauquet, C. M., Knudson, D. L., and Brown, F. eds. Springer–Verlag Wien, Inc., New York.

Zwaagstra, J. C., H. Ghiasi, S. M. Slanina, A. B. Nesburn, S. C. Wheatley, K. Lillycrop, J. Wood, D. S. Latchman, K. Patel, and S. L. Wechsler. 1990. Activity of herpes simplex virus type 1 latency–associated transccript (LAT) promoter in neuron–derived cells: evidence for neuron specificity and for a large LAT transcript. J. Virol. 64: 5019–5028.

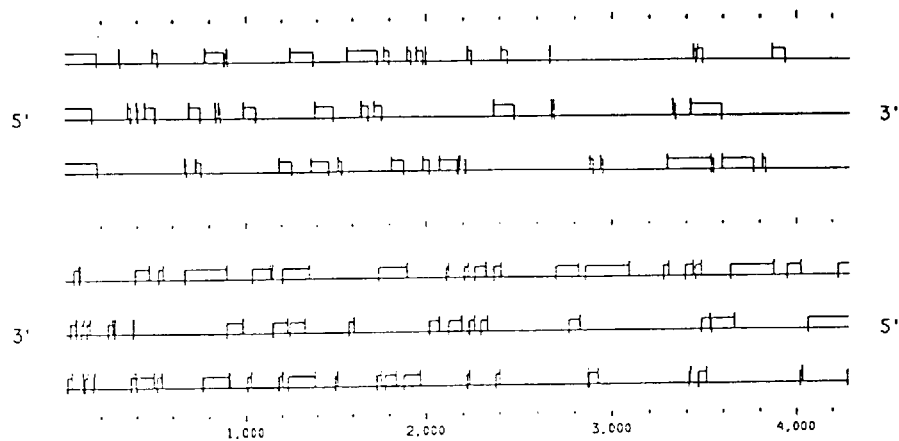

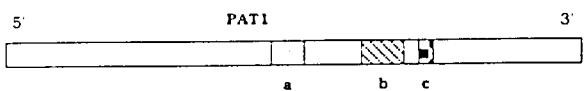

```
a.
1416        TCGGTTAGTT              1425
1466      AGGCTCGGTTAGTT             1479
1427       TAGGCTCGGTTAGT            1440
1486       TAGGCTCGGTTAG             1498
1453        CGGCTAGTTTATAAG          1467
1526      GTGCGGCTAGTTTATAAG         1543
1517              TATAAGTCGGTG       1528
1571              TATAAGTCGGTG       1582
1559       GTGCGGCTAGT               1569 b.
1830        CTCTGGTAAA              1839
1912      CTATACTCTGGTA             1924
1943        TACTCTGGTACTCTGATA      1960
1964      CTATACTCTGGTA             1976
1978       ATACTCTGGTA              1988
1996             GTACTCTGATA        2006
2005      TATACTCTGGTACT            2018 c.
2094         TGGTATTGGTAT           2105
2100         TGGTATTGGT             2109
2114        AAAGGTATCAA             2124
2132       AAACAAAGGTATTGGTAT       2149
2163         CAAAGGTATTA            2173
2175        ACAAAGGTATTAAACAAA      2192
2188       AAACAAAGGTATTAAACAAA     2205
2204        AAAGGTATCAAACAA         2218
```

FIG. 9A
A. PROFILE
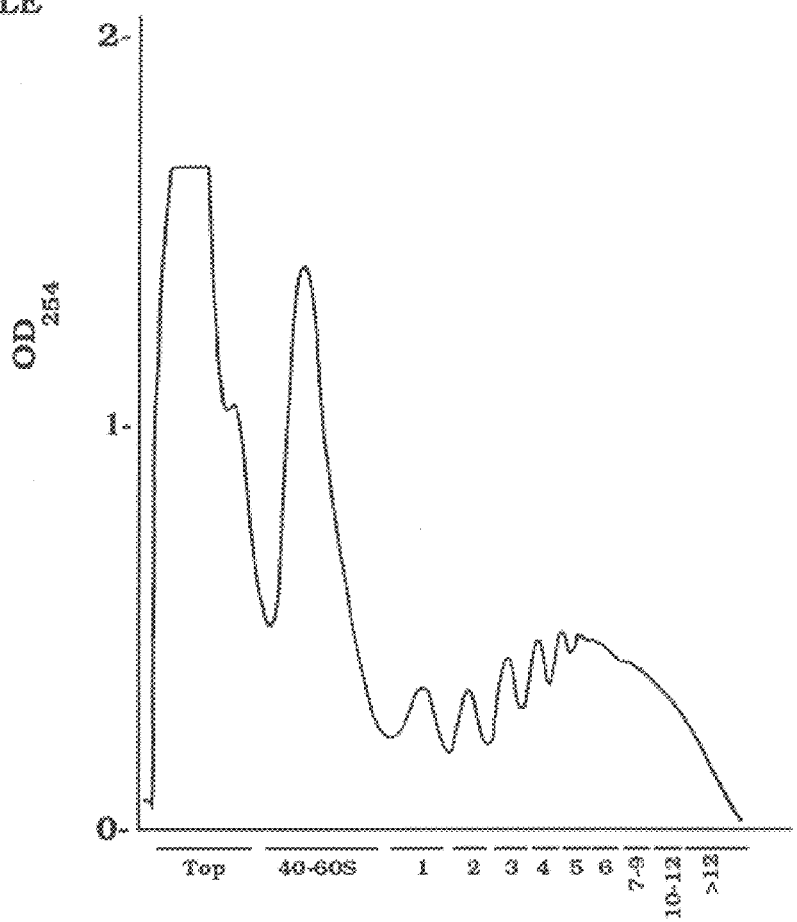
B. PAT1
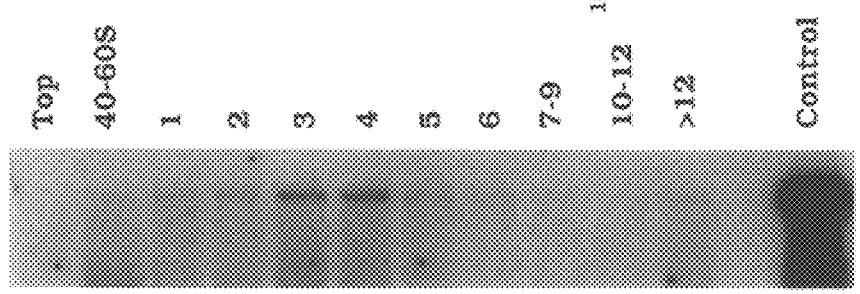
FIG. 9B
C. ACTIN
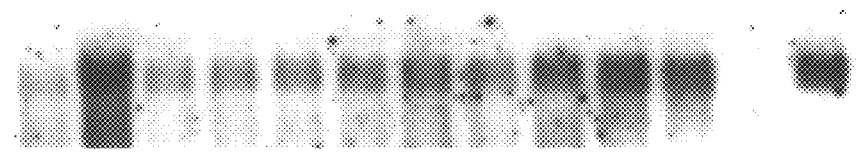
FIG. 9C

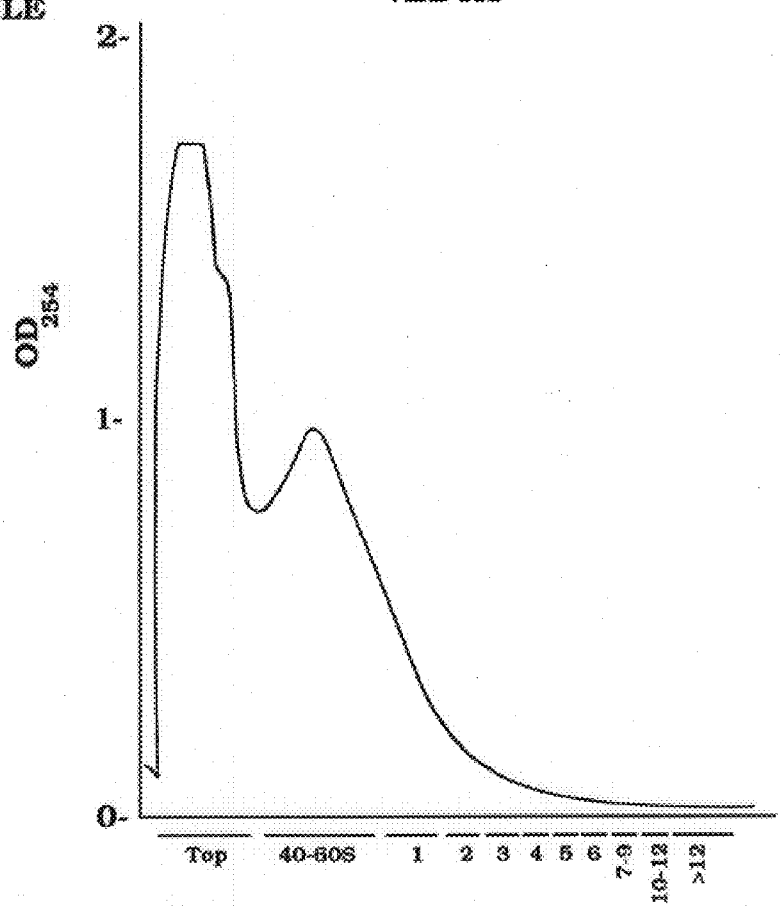
FIG. 10A A. PROFILE
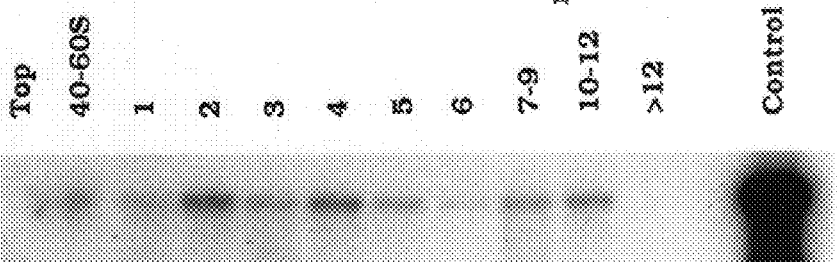
FIG. 10B B. PAT1
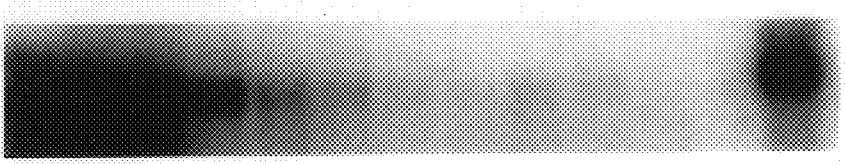
FIG. 10C C. ACTIN FIG. 11A
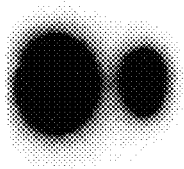
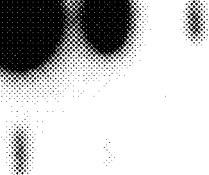
FIG. 11B
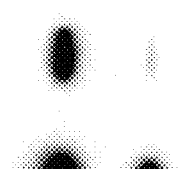
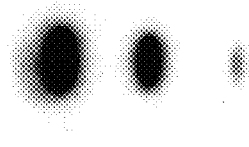

FIG. 12A-a
A.
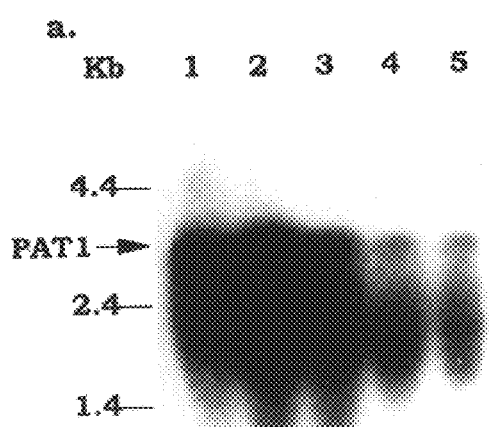
FIG. 12A-b
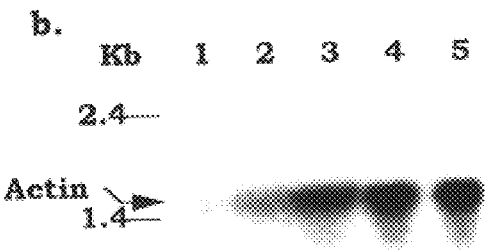
FIG. 12B
B.
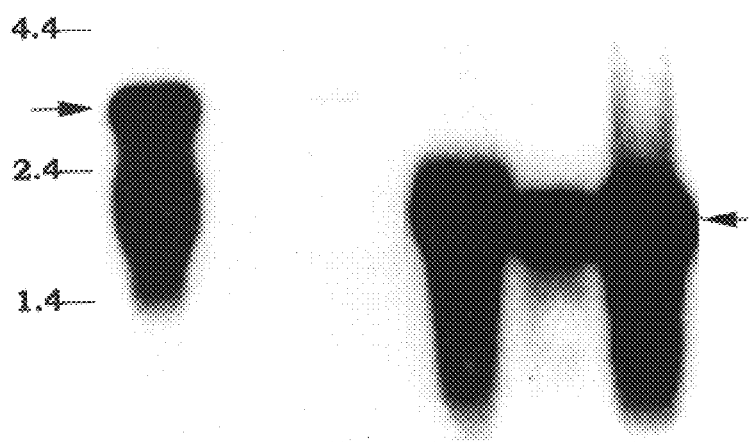

FIG. 13A
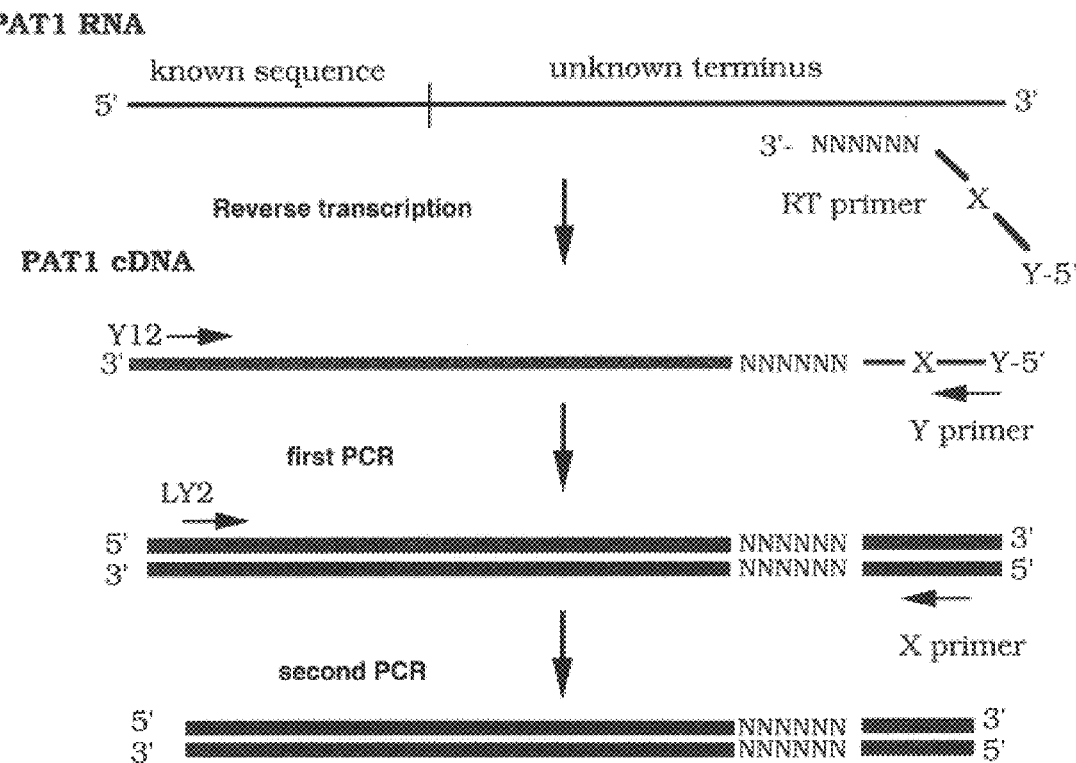
B. 1st PCR
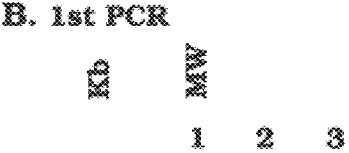
C. 2nd PCR
FIG. 13B
FIG. 13C

| A. TN368 | B. TNP1 | C. TNP2 | D. TNP3 |
|---|---|---|---|
| μg | μg | μg | μg |
| 0.10 | 0.10 | 0.10 | 0.10 |
| 0.50 | 0.50 | 0.50 | 0.50 |
| 1.00 | 1.00 | 1.00 | 1.00 |
| 5.00 | 5.00 | 5.00 | 5.00 |
| 10.0 | 10.0 | 10.0 | 10.0 |

FIG.17A   FIG.17B   FIG.17C   FIG.17D

| E. SF21AE | F. SFP2 | G. SFP4 | H. Hz-1DNA |
|---|---|---|---|
| μg | μg | μg | μg |
| 0.10 | 0.10 | 0.10 | 0.01 |
| 0.50 | 0.50 | 0.50 | 0.02 |
| 1.00 | 1.00 | 1.00 | 0.04 |
| 5.00 | 5.00 | 5.00 | 0.08 |
| 10.0 | 10.0 | 10.0 | 0.16 |
| | | | 0.32 |
| | | | 0.64 |

FIG.17E   FIG.17F   FIG.17G   FIG.17H

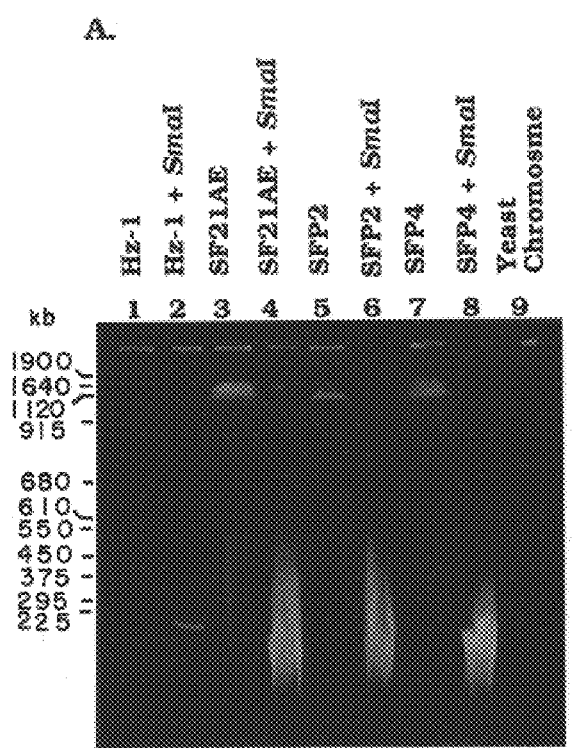 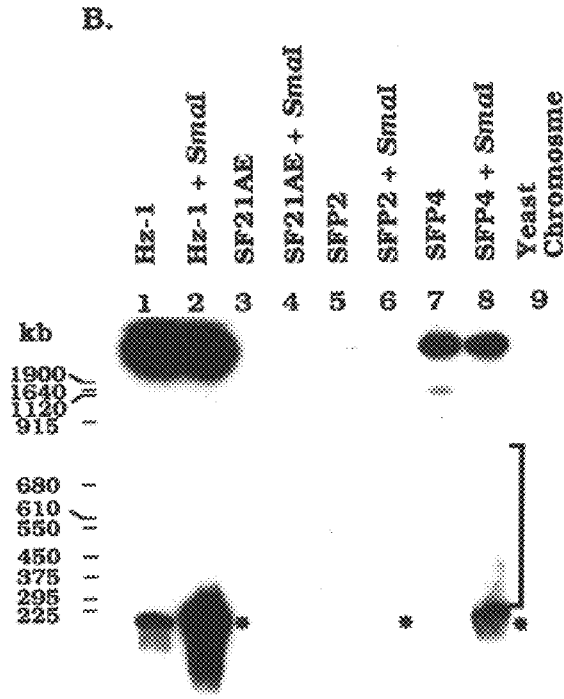

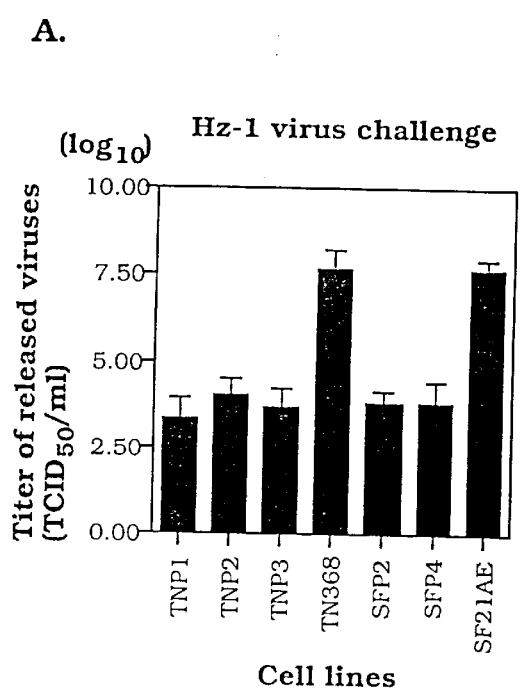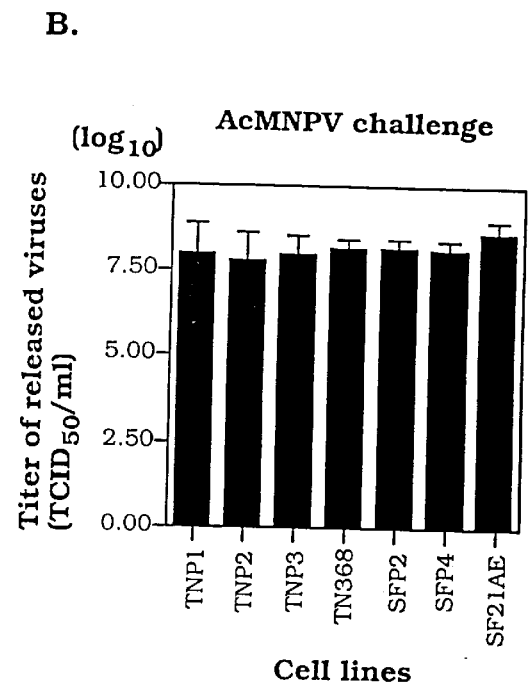
FIG.23A
FIG.23B

HZ-1 VIRUS PERSISTENCE-ASSOCIATED-GENE 1 (PAG1) PROMOTER USES THEREFOR, AND COMPOSITIONS CONTAINING SAME OR PRODUCTS THEREFROM

REFERENCE TO RELATED APPLICATION

Reference is made to U.S. application Ser. No. 08/249,617, filed May 26, 1994 and U.S. Provisional applications Ser. Nos. 60/004,894 filed Oct. 6, 1995 and 60/005,128 filed Oct. 11, 1995, each of which is incorporated herein by reference.

FIELD OF THE INVENTION

This invention relates to the production and the application of the nucleotide sequence (DNA) encoding the persistence-associated gene 1 (pag1) of Hz-1 virus (also called Hz-1 Baculovirus or Hz-1 V), the promoter thereof, the transcript thereof (RNA; i.e., persistence-associated transcript 1; PAT1), a vector system employing the gene and/or promoter and/or transcript, particularly for expression of DNA exogenous to the vector system, especially, a Baculovirus, an E. coli, avipox virus, vaccinia virus, lambda virus, herpes virus, polio virus, or adenovirus system, preferably a Baculovirus system. The invention further relates to expression products from use of the gene and/or promoter and/or transcript in a vector system for expression of DNA exogenous to the vector system. The expression products can be antigens or immunogens; and therefore, the invention further relates to immunological, antigenic or vaccine compositions containing the expression products. Further, since the vector, in certain instances, can be administered directly to a suitable host, the invention relates to compositions containing the vector. Additionally, since the expression product can be isolated from the vector in vitro or from cells infected by the vector in vitro, the invention relates to methods for expressing a product, e.g., comprising: inserting the gene and/or promoter and/or transcript with exogenous coding nucleotide sequence into a suitable vector, e.g., by recombination, followed by infection of suitable cells in vitro; or infecting suitable cells in vitro with a recombinant virus containing the gene and/or promoter and/or transcript and the exogenous coding nucleotide sequence; and, optionally extracting, purifying or isolating the expression product from the cells.

As the expression products can provide an antigenic, immunological or protective (vaccine) response, the invention further relates to products therefrom; namely, antibodies and uses thereof. More in particular, the expression products can elicit antibodies. The antibodies can be formed into monoclonal antibodies; and, the antibodies or expression products can be used in kits, assays, tests, and the like involving binding, so that the invention relates to these uses too.

Several publications are cited in the following text, with full citation of each set forth in the section headed References or with full citation occurring where cited. The publications cited throughout the text are hereby incorporated herein by reference.

BACKGROUND OF THE INVENTION

Hz-1 virus is a member of the family Baculoviridae (Wilson, 1991) and is the first invertebrate virus in which differential viral gene expression during productive and persistent viral infections is demonstrated (Chao, et al., 1992). Thus far, two subfamilies have been described in the Baculoviridae insect virus family: the Eubaculovirinae and the Nudibaculovirinae.

The characteristic feature of Eubaculovirinae is the occlusion of virion in polyhedra proteinaceous inclusion body. The Eubaculovirinae is further divided into two genera: the first genus is "nuclear polyhedrosis virus", with $Autographs$ $californica$ multiple nuclear polyhedrosis (AcMNPV) as an exemplary type species of this genus; and, "granulosis virus" being the second genus.

Nudibaculovirinae, are known as nonoccluded viruses since virions are not packaged into inclusion bodies at any stage of their life cycle. (Wilson, 1991). Hz-1 virus was classified as a species of the Nudibaculovirinae family (Wilson, 1991). Recently Hz-1 virus and other non-occluded Baculoviruses were removed from the Baculovirus family and are temporarily unclassified (Volkman, 1995). Hz-1 virus was originally identified as a persistently infected virus in the $Heliothis$ $zea$ cell line, IMC-Hz-1 (Granados et al. 1978). Hz-1 virus is a rod-shaped virus containing 228 kb double-stranded circular DNA genome (Chao et al., 1990 a, b; Huang et al., 1982; Ralston et al., 1981). Relative to being a Baculovirus, the host range of Hz-1 virus is broad and persistent Hz-1 virus infections have been established in many insect cells (Chao et al., 1990a; Wood and Burand, 1986; Granados et al., 1978). Infection of Hz-1 virus can produce both productive and persistent viral infections (Ralston, et al., 1981; Burand et al., 1986; Chao et al., 1992).

More specifically, persistent viral infection has long been reported to occur naturally in insects. Many of the persistently infected viruses can be activated (Burand et al., 1986; Chao et al., 1985; Jurkovicoba, 1979; Hughes et al., 1993; Podgwaite and Mazzone, 1986; Wood and Burand, 1986) upon the change of rearing temperature, high humidity, decrease of food quality, superinfection of different viruses, and/or other stimuli. However, due to the difficulty in establishing persistent viral infection in laboratory insect stocks, persistent viral infection is usually studied after an unexpected viral activation from a previously healthy-looking insect or cell. It would therefore be advantageous to have a vector system in which persistent viral infection may be achieved, with activation or replication available if desired for virus propagation (e.g., cloning) or if necessary or desired for expression, such as of exogenous DNA.

The persistently infected Hz-1 virus was shown to be activated by heterologous viruses (Burand et al., 1986) and the host cells can be resistant to the superinfection of homologous virus due to induction of apoptosis (Lee et al., 1993).

Differential viral gene expression is also known in the herpes viruses in mammals. In the Epstein-Barr virus, approximately 12 genes are expressed during latent infection and approximately 50 to 100 viral genes were expressed in cells that have entered a lytic phase of viral growth (Klein, 1989; Metzenberg, 1990). In herpes simplex virus, the virus probably encodes more than 70 polypeptides during productive viral infection. During latent viral infection, only three related latent associated transcripts (LATS) generated by the same gene are detectable (Spivack and Fraser, 1987; Stevens et al., 1987).

The patent and scientific literature includes various viral vector systems, uses therefor, and exogenous DNA for expression of protein by such systems, as well as uses for such proteins and uses for products from such proteins.

For instance, recombinant poxviruses (e.g., vaccinia, avipox virus) and exogenous DNA for expression in viral vector systems can be found in U.S. Pat. No. 5,174,993 (e.g., recombinant avipox virus, vaccinia virus; rabies glycoprotein (G), gene, turkey influenza hemagglutinin gene, gp51, 30 envelope gene of bovine leukemia virus, Newcastle Disease Virus (NDV) antigen, FeLV envelope gene, RAV-1 env gene, NP (nudeoprotein) gene of Chicken/Pennsylvania/1/83 influenza virus, matrix and preplomer gene of infectious bronchitis virus; HSV gD; entomopox promoter, inter alia), U.S. Pat. No. 5,338,683, e.g., recombinant vaccinia virus, avipox virus; DNA encoding HSV glycoproteins, inter alia; U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, BVDV, HCMV, canine parvovirus, equine influenza, FeLV, FHV, Hantaan, C. tetani, avian influenza, mumps, NDV, inter alia); WO 92 08789 (e.g., recombinant vaccinia, avipox, Morbillivirus [e.g., measles F, hemagglutinin, inter alia); U.S. Pat. No. 4,722,848 (e.g., recombinant vaccinia virus; HSV tk, glycoproteins [e.g., Gb, Gd], influenza HA, Hepatitis B [e.g., HBsAg], inter alia); U.K. Patent GB 2 269 820 B (recombinant poxvirus; flavivirus structural proteins); WO 92/22641 (e.g., recombinant poxvirus; immunodeficiency virus, inter alia); WO 93/03145 (e.g., recombinant poxvirus; IBDV, inter alia); WO 94/16716 (e.g., recombinant poxvirus; cytokine and/or tumor associated antigens, inter alia).

U.S. Pat. No. 4,769,331 relates to herpesvirus as a vector. There are also poliovirus and adenovirus vector systems.

Baculovirus expression systems, exogenous DNA for expression therein, and purification of recombinant proteins therefrom can be found in Richardson, C. D. (Editor), *Methods in Molecular Biology* 39, "Baculovirus expression protocols" (1995 Humana Press Inc.) (see, e.g., Ch.18 for influenza HA expression, Ch.19 for recombinant protein purification techniques), Smith et al., "production of huma beta interferon in insect cells infected with a Baculovirus expression vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus Vector," Molecular and Cellular Biology March 1984, Vol. 4, No. 3, pp. 399–406; EPA 0 370 573 (Skin test and test kit for AIDS, discussing Baculovirus expression systems containing portion of HIV-1 env gene, and citing U.S. application Ser. No. 920,197, filed Oct. 16, 1986 now abandoned and EP Patent publication No. 0 265785); U.S. Pat. No. 5,147,788 (Baculovirus vectors and methods of use); U.S. Pat. Nos. 5,155,037, 5,278,050 (insect signal sequences replacing CD4 natural signal peptide coding in recombinant Baculovirus expression vector); U.S. Pat. No. 5,162,222 (Baculovirus first IE promoter/Baculovirus second IE promoter (opposite orientation to first)/cloning restriction site (for insertion of heterologous coding DNA sequence Baculovirus vector); U.S. Pat. No. 5,244,805 (Baculovirus expression vectors); U.S. Pat. No. 5,169,784 (Baculovirus dual promoter expression vector); U.S. Pat. No. 5,194,376 (Baculovirus expression system); U.S. Pat. No. 5,322,774 (procaryotic leader sequence in recombinant Baculovirus expression system); U.S. Pat. No. 5,110,729 (peptide production using Baculovirus in cultured cells); U.S. Pat. No. 5,179,023 (Baculovirus expression vectors expressing recombinant human alpha-Galactosidase in cell cultures); U.S. Pat. No. 5,186,933 (method to express rotavirus gene in Baculovirus); U.S. Pat. No. 5,229,293 (Baculovirus-JEV recombinant; JEV E protein as exogenous DNA); U.S. Pat. No. 5,260,199 (1,25-dihydroxyvitamin $D_3$ receptor protein produced in Baculovirus); U.S. Pat. No. 5,290,686 (influenza A M2 expression in Baculovirus); U.S. Pat. No. 5,294,548 (hepatitis A virus expression in Baculovirus); U.S. Pat. No. 5,272,063 (human nerve growth factor expression in Baculovirus); U.S. Pat. Nos. 5,180,581 and 5,352,451 (Baculovirus with inactivated gene optionally as modified to express A protein as insect control agent); U.S. Pat. No. 5,300,435 (cell line susceptible to Baculovirus); and U.S. Pat. No. 5,179,007 (production and isolation of protein through lepidopteran cells transfected or infected with recombinant Baculovirus).

Baculovirus vector systems offer unique advantages. For instance, the advantages of: eliminating non-specific reactions from human cell cultures, having a relatively narrow host range which is restricted to arthropods, and, of having U.S. EPA approval of use of species thereof for control of insect pests (with *Autographa californica* nuclear polyhedrosis virus ("AMNPV") having been applied to crops for many years under EPA Experimental Use Permits).

However, Baculovirus vector systems have suffered from disadvantages such as reliance upon the very late polyhedrin promoter. That is, the polyhedrin promoter based Baculovirus expression system ("PPBE") or, the use of the polyhedrin promoter, has disadvantages. For instance, the polyhedrin promoter is so very late as a promoter, expression can occur 15 to 18, average 16, hours after infection when nucleocaspids are enveloped within the nucleus and viral occlusions begin to form (each occlusion containing many viral particles embedded in a paracrystalline protein matrix, formed from polyhedrin, a single matrix, which accumulates to high levels and can constitute 25% or more of total protein mass in infected cell).

Further, Baculovirus is a lytic virus. That is, lyses of the host cells occurs. This lyses of host cells can complicate production and purification of proteins not naturally occurring in Baculovirus. Lysis results in the release of numerous host and viral proteins, as well as loss of control of the enzymatic system of the host cells. This release and loss of control can lead to degradation on any structural level of foreign protein expressed with Baculovirus. Accordingly, harvesting of foreign proteins must be carefully timed.

Thus, the possibility of avoiding lysis would be advantageous. It would therefore be advantageous to have a strong and early to very early promoter. It would even be more advantageous to have an early to very early promoter which is stronger or has greater expression than polyhedrin. It would also be advantageous to provide such a strong to very strong, early to very early promoter which can be used in the polyhedrin coding region of typical Baculovirus presently used, e.g., AcMNPV, since the polyhedrin coding region is an already known non-essential site in Baculovirus, or even in other viral vector systems. It would even be further advantageous if rather than lysis there was the possibility even of persistent infection such that through cell life and replication there is expression of the foreign protein. It would additionally be advantageous to provide nucleic acid molecules encoding such a strong to very strong, early to very early promoter, or functional portions thereof, or, nucleic acid molecules which hybridize to the promoter or functional portion thereof, so as to be useful for detecting presence or for PCR amplification.

However, given the similarity in replication between herpes virus and Baculovirus (nuclear replication) and of a latency or persistent infection, use of pag1, the promoter thereof, and fragments thereof, especially operably linked to exogenous DNA, in herpes virus, are envisioned.

OBJECTS AND SUMMARY OF THE INVENTION

It is therefore an object of the invention to provide any of the aforementioned as being advantageous.

More in particular, it is an object of the invention to provide a promoter, preferably a promoter that can take advantage of the well-developed insect cell or Baculovirus expression systems, more preferably a promoter which avoids any drawback of or has any advantageous attribute over PPBE, and most preferably a promoter which can be as strong, if not stronger than polyhedrin while also being an early to very early promoter.

It is a further object of the invention to provide a protein expression system, e.g., a promoter and/or promoter with some coding, which may express foreign proteins in any of viruses, bacterium, yeast, insect cells, and animal cells.

It is yet another object of the invention to provide a vector system having an early to very early, strong to very strong promoter.

It is yet a further object of the invention to provide, and the present invention provides, a nucleic acid molecule comprising a nucleotide sequence encoding pag1 promoter, or a functional portion thereof, including a nucleotide sequence encoding any of pag1, PAT1, and any of bases −728 to +1, −728 to +6, −728 to +9, −728 to +29, −728 to +198, −727 to +29, −607 to +29, −493 to +29, −403 to +29, −315 to +29, −212 to +29, −158 to +29, −90 to +29, −69 to +29, −42 to +29, −14 to +29, and 0 to +29 of the nucleotide sequence of pag1. The nucleotides of the aforementioned recited sequences can have additions or deletions of up to about 15%, preferably up to about 10%, more preferably up to about 5%, of the number of bases recited.

It is still a further object of the invention to provide and the present invention provides, a nucleic acid molecule comprising a nucleic acid sequence which sufficiently hybridizes to any of the aforementioned promoter, or functional portion thereof, or to a sufficient portion of the promoter or functional portion thereof, including at least about 20, preferably about 20 to 110, more preferably about 50 to 110, bases (±10%) of promoter or of the functional fragments identified above by position numbers, with sufficient hybridization including at least about 80% hybridization being mild conditions, at least about 90% hybridization being preferred and being moderate conditions, and most preferred being at least about 95% hybridization which is stringent conditions, so that the nucleic acid sequence can be used as a probe for detection (e.g. labeled) or as a primer for amplification, e.g., by PCR, of the promoter or functional portion thereof.

The present invention even further provides a vector containing the pag1 promoter, or a functional portion thereof. The invention includes yet further, such a vector containing exogenous nucleic acids or nucleotides sequence, e.g., DNA, preferably exogenous coding nucleic acids or nucleotide sequence, e.g., DNA encoding an antigenic or immunologically active protein functionally or operably linked to the pag1 promoter or functional portion thereof; or alternatively or additionally, such a vector having engineered or natural restriction sites for insertion of exogenous or heterologous nucleic acids or nucleotide sequences, preferably in a position for functional or operable linkage when so inserted. In certain preferred embodiments the invention provides such a vector wherein the promoter or promoter and exogenous nucleotides or nucleotide sequence are situated in a nonessential region of the vector genome. The vector is most preferably a Baculovirus, e.g., AcMNPV, Hz-1, but can also be another type of virus, e.g., poxvirus (since entomopox promoters have been shown to function in vaccinia or avipox virus), and preferably herpes virus (since like Baculovirus, herpesvirus replicates in the nucleus, not the cytoplasm, as does poxvirus). The vector can also be a bacteria, e.g., E. coli, a higher animal or vertebrate, e.g., mammalian, or invertebrate, e.g., insect cell, yeast, and the like. The exogenous DNA can be any of the aforementioned exogenous DNA for expression of protein by a vector system. The exogenous DNA can include a marker, e.g., a color or light marker. The exogenous DNA can also code for a product which would be detrimental to an insect host such that by in vivo expression the vector can be a pesticide or insecticide. The vector can also have an inactivated gene for insect control. The vector can be for cloning or expression.

The invention also provides methods for obtaining expression from a vector containing exogenous DNA and the pag1 promoter or functional portion thereof as well as for obtaining a product from expression of the exogenous DNA by a vector containing the pag1 promoter or functional portion thereof. Such methods can include introducing the vector to a host: for in vivo expression, e.g., administering or infecting a host with a recombinant virus, or for in vitro expression, e.g., introducing a recombinant virus to host cells cultured in vitro with optional isolation or purification of the expression product.

It is yet an additional object of the invention to provide, and the invention provides, antigenic, vaccine, immunological, insecticide or pesticide compositions comprising the vector or expression products of the vector containing the pag1 promotor or functional portion thereof and coding nucleic acids or nucleotide sequence (e.g., DNA). For instance, a composition comprising the vector and a suitable carrier, or a composition comprising a product of expression of the vector and a suitable carrier.

Still further, the invention provides methods employing the compositions. The invention includes a method to elicit an antigenic, vaccine or immunological response in a host comprising administering to the host, or inoculating the host with, the composition. The invention likewise comprehends a method for controlling insects or invertebrates comprising applying to desired plants, foliage or crops, or their seeds, or a cultivated area containing the plants or seeds, an insecticidal or pesticidal composition.

It is yet another object of this invention to provide, and the invention provides products from such compositions, or from the methods; for instance antibodies. The antibodies, or the product which elicited them, or monoclonal antibodies from the cells which produced the antibodies, can be used in binding assays, tests or kits to determine the presence or absence of an antigen or antibody.

The present invention involves the elucidation of the pag1 promoter and functional portions thereof, vectors employing the promoter or functional portion thereof, primers and probes for the promoter or functional portions thereof, antigenic, vaccine, immunological, insecticide or pesticide compositions employing vectors or expression products thereof, antibodies elicited thereby, uses for the expression products and antibodies, and methods for making and using the promoter or functional portion thereof, vectors, primers, probes, compositions, expression products and antibodies.

These and other objects and embodiments within the present invention are described or are obvious from the following Detailed Description.

BRIEF DESCRIPTION OF DRAWINGS

FIG. 1 contains (A) and (B) and shows: Location and sequence of pag1 gene.

FIG. 2 contains (A) and (B) and shows: The definition of the 5' and 3' ends of PAT1.

FIG. 3 contains (A), (B), and (C) and shows: DNA sequence analysis of pag1.

FIG. 3(A): Computer ORF analysis of pag1 is shown. ORFs are indicated as open boxes. Start codons are marked with upper bars and stop codons are marked with lower bars. The orientations of the top three frames are the same as for PAT1. The orientations of the bottom three reading frames are opposite from PAT1. The transcriptional region of PAT1 is indicated by an arrow.

FIG. 3(B): Relative locations of clustered repeats on PAT1 are shown.

FIG. 3(C): Sequences of three major direct repeats and their positions are shown (SEQ. ID. NOS. 2–25). Only those repeats larger than 10 bases are included.

FIG. 6 contains (A) and (B) and shows: Definition of the region upstream from the transcription site which regulates the promoter activity of pag1.

FIG. 9 contains (A), (B), and (C) and shows: Polysome fractionation of the persistently infected TNP3 cells without the addition of EDTA. Profile of $OD_{254}$ absorbency of postmitochondrial lysates isolated from $1 \times 10^7$ cells are shown (A). Each fraction was then collected and analyzed by Northern hybridization using either pag1 (B) or actin (C) probes. One-twelfth of the total RNA extracted from $1 \times 10^7$ TNP3 cells was loaded into the control lanes to serve as a control.

FIG. 10 contains (A), (B), and (C) and shows: Ribosome knock-out by EDTA treatment in the polysome fractionation experiment. Postmitochondrial lysates collected from persistently infected $1 \times 10^7$ TNP3 cells were subjected to sucrose gradient centrifugation. Profile of $OD_{254}$ absorbency of the gradients (A) and Northern hybridization of each fractions with either pag1 (B) or actin (C) probes are shown. One-twelfth of the total RNA extracted from $1 \times 10^7$ TNP3 cells was loaded into the control lanes to serve as a control.

FIG. 11 contains (A) and (B) and shows: Slot blots of nuclear and cytoplasmic RNAs from persistently infected TNP3 cells. Slot blots with a series of 10× dilutions of nuclear and cytoplasmic RNAs starting from 5 ug per slot. These blots were hybridized with pag1 probe (A) or actin probe (B).

FIG. 12 contains (A) and (B) and shows: The analysis of post-transcriptional modifications of PAT1.

FIG. 12(A): Salt elution of a PBA column showed that PAT1 is not capped. Total RNAs were harvested from the cells persistently infected with the Hz-1 virus. After PBA column elution, eluted RNA fractions were analyzed by Northern hybridization. The results show that PAT1 was mainly eluted by high-salt elution buffer (a. lanes 1, 2, and 3), however, the control actin mRNA was mainly eluted by low-salt buffer (b. lanes 3, 4, and 5). This indicates that PAT1 is not 5' capped.

FIG. 12(B): OligoKdT) binding experiments showed that PAT1 is not polyadenylated. Total RNA (75 mg) harvested from the persistently infected cells was captured by oligo (Dt)-conjugated Dynabeads™. After washing three times with the washing buffer, poly(A)-containing mRNAs were eluted with 75 ul $H_2O$ and analyzed by Northern hybridization. Then 2.5 ug of total RNAs was loaded in lanes 1 and 4; 2.5 ul of the eluted solution was loaded in lanes 2 and 5; and 12.5 ul of the eluted solution was loaded in lanes 3 and 6. Lanes 1, 2, and 3 were hybridized with a pag1 probe and lanes 4, 5 and 6 were hybridized with an actin probe. These experiments revealed that PAT1 is not polyadenylated.

FIG. 13 contains (A), (B), and (C) and shows: Synthesis 3' end of cDNA fragment using random primer-primed PCR.

FIG. 13(A): This panel shows CDNA synthesis strategy using random primer-primed PCR. RT primers are primers with known X and Y sequences linked with random hexamers by which the CDNA of PAT1 is synthesized. Y12 and LY2 are known sequences derived from the genomic DNA sequence.

FIG. 13(B): Results of the first PCR using Y12 and Y primers are shown. The largest amplified 1.3-kb band is indicated.

FIG. 13(C): The 1.3-kb band (see panel B) was gel purified and further amplified using LY2 and X primer. A much stronger 1.3-kb band was amplified.

FIG. 15 contains (A), (B), and (C) and shows: In vitro transcription and translation experiments showing the non-protein encoding nature of PAT1.

FIG. 16 contains (A), (B), (C), (D), (E), (F), (G), and (H) and shows: Examples of infectious center assay to study the final fate of cells upon viral reactivation.

FIG. 17 contains (A), (B), (C), (D), (E), (F), (G), and (H) and shows: Dot hybridization to calculate the percentage of viral DNA contained in persistently infected cells. Various amounts of total genomic DNAs from two parental and five persistently infected cell lines were dotted onto filters and hybridized with viral genomic DNA. Various amounts of Hz-1 viral DNA was also dotted onto filters and hybridized simultaneously to serve as standards for the calibration of viral DNA contained in different cell lines.

FIG. 20 contains (A) and (B) and shows: The analysis of physical status of viral genomes in the persistently infected TN cells by PFGE. The genomes of virus, parental cell TN368, and persistently infected cells TNP1, TNP2, and TNP3 were treated as follows:

FIG. 21 contains (A) and (B) and shows: Pulsed-field gel electrophoresis analysis of the persistently infected cells SFP2, and SFP4. Virus, parental cell SF21AE, and persistently infected SFP2, and SFP4 cells were treated as follows:

FIG. 21(A) shows: fractionated through PFGE with or without SmaI digestion, and

FIG. 21(B) shows: The gel was then blotted onto a filter gel and hybridized with viral genomic DNA probe. An asterisk (*) marks the bands or regions where linearlized viral genomic DNA resided. After SmaI digestion, viral DNAs which are possibly inserted in the host genomes are marked with brackets.

FIG. 23 contains (A) and (B) and shows: Viral interference assay of the persistently infected cells. Parental and persistently infected cells were challenged with either Hz-1 virus (A) or AcMNPV (B). The titers of the viruses released into the media by the infection of different viruses to two parental and five persistently infected cells were assayed. Data (means±standard deviations) were collected from three sets of experiments with three independent $TCID_{50}$ analyses.

DETAILED DESCRIPTION

Figures 1A, 1B:
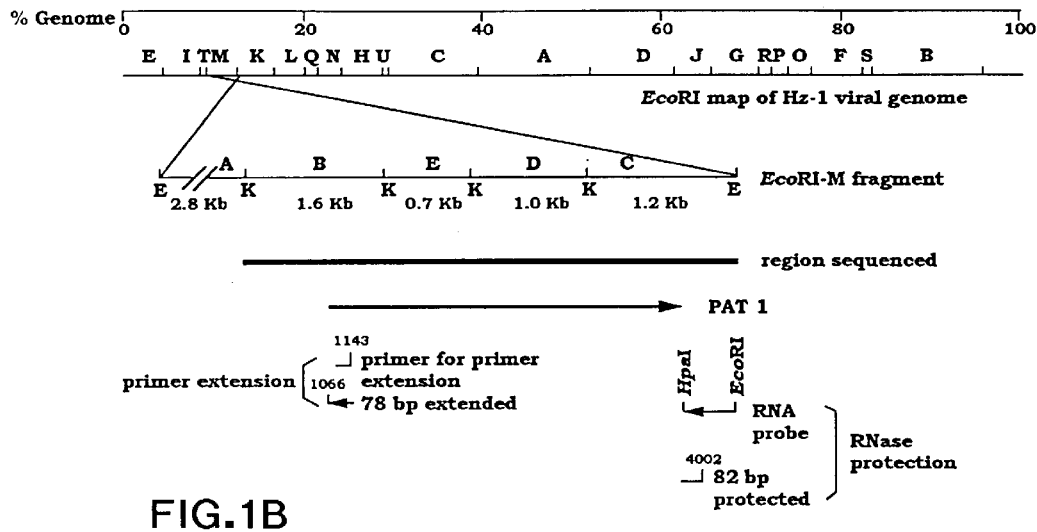
FIG. 1(A): The % viral genome is shown in the first line. The EcoRI map of the linearized 228 kb Hz-1 viral genome is shown in the second line. The KpnI map of the EcoRI-M fragment is shown in the third line. The region which has been sequenced is shown in the fourth line. The orientation and transcriptional region of PAT1 is shown in the fifth line. The alphabetical designations above the line denote the viral DNA restriction fragments and under the line denote restriction sites: K, KpnI; E, EcoRI.
FIG. 1(B): The nucleotide sequence of pag1 is shown (SEQ. ID. NO. 1). The putative GATA motif, AP1 consensus sequence, and CAAT and TATA boxes are underlined. The transcription start site is indicated by an arrow and the transcription termination site is marked by a star.

As discussed above, the present invention entails the pag1 promoter, or a functional portion thereof, i.e., a nucleic acid molecule comprising a nucleotide sequence encoding pag1 promoter, or a functional portion thereof of Hz-1. The nucleic acid can be DNA or RNA. The coding can be for pag1, PAT1, or a functional portion thereof. Considering the pag1 sequence when the promoter region is counted from 1 to 1095 and the coding region is from 1066 to 4002, best promoter activity is from 976 to 1095 bases, and positively counting from the start site (the coding region conserving the transcription start site) such that 1066 is +1, best promoter activity is from bases −90 to 29; but, functional portions can generally include bases −728 to +1, −728 to +6, −728 to +9, −728 to +29, −728 to +198, −727 to +29, −607 to +29, −493 to +29, −403 to +29, −315 to +29, −212 to +29, −158 to +29, −90 to +29, −69 to +29, −42 to +29, −14 to +29, and 0 to +29. These base recitations can have additions or deletions, preferably end (5' or 3') additions or deletions, of up to about 15%, preferably up to about 10%, more preferably up to about 5%, of the number of bases recited. Midstream insertional or deletional mutations can occur at about the same preference. Thus, a promoter or functional portion thereof should have at least 85% homology, preferably at least 90% homology, more preferably at least 95% and most preferably about 95% homology to pag1, PAT1, or a portion thereof as stated above in terms of bases. A probe or primer therefor should include at least about 20, preferably about 20 to 110, more preferably about 50 to 110 bases (±10%) of pag1, PAT1 and the fragments identified by position numbers, with at least 80% hybridization being mild conditions, at least about 90% hybridization being moderate conditions, and at least about 95% hybridization being stringent conditions.

The pag1 or functional portion thereof has expression as strong as polyhedrin to ten times greater strength, and, expression is observed as early as 30 minutes post infection. More than 100 viral specific transcripts can be detected during Hz-1 virus viral infection; however, only one transcript is detectable during persistent viral infection. The latter RNA is named the persistence-associated transcript 1 (PAT1) (Chao et al., 1992). The gene encoding PAT1 is pag1 (FIG. 1).

In this discussion, it should be understood that uses for pag1 promoter on the DNA level can be extrapolated to PAT1 on the RNA level.

Differential viral gene expression was previously elucidated during productive and persistent infections of Hz-1 virus in insect cells. In spite of numerous expressions of viral transcripts during productive viral infection, only one persistency associated transcript, namely PAT1, was detectable during viral persistency. The PAT1 encoding gene pag1 does not contain any significant ORFs. PAT1 was found not to associate with the cellular translation machinery and is located exclusively in the nucleus. The PAT1 molecule is neither capped nor polyadenylated and the sequence of CDNA is identical to that of the genomic DNA. This suggests that it is not spliced or further edited after transcription. A 90 bases sequence which includes a typical TATA box at −27 bases from the transcription start site was found to be crucial for a strong promoter activity. The PAT1 promoter appears juxtaposes to its transcription start site which suggests that PAT1 is driven by this closely associated promoter and is not to be an intron of other Hz-1 viral transcripts. Accordingly, PAT1 is a novel viral nuclear RNA which may not necessarily be functional at the protein level.

Thus far, PAT1 is the only known constitutively-expressed transcript throughout Hz-1 virus baculoviral productive infection. In addition, during persistent viral infection, PAT1 is still strongly expressed while all other viral-specific transcripts are turned off (Chao et al. 1992). Test code analysis using UWGCG program also indicates that PAT1 is not likely to encode a protein. A functional ORF may be generated by RNA editing (Powell et al., 1987) or multiple splicing. However, this is not likely because the sequence of CDNA is virtually identical to the genomic DNA. Another possibility that cannot be excluded is that a functional ORF can be generated by frameshift translation (Jacks and Varmus, 1985). If so, large numbers of multiple frameshifts may be necessary to generate a protein of reasonable size. Although this has not been previously demonstrated, it does not seem likely to occur in PAT1 translation.

Thus, the expression of exogenous proteins from the pag1 promoter presents surprising, unexpected and exciting embodiments. Since pag1 is the operational transcript during persistent infection, insertion of exogenous DNA sufficiently downstream from the promoter, and downstream or within the pag1 coding region such that the pag1 gene remains functional, while in Hz-1 virus or as a chimeric or multiple insert into another virus, e.g., another Baculovirus, presents a vector which can have persistent infection with expression of the exogenous DNA during persistent infection, or expression of the DNA during persistent infection and when or after the virus is activated, or expression only when the virus is activated, or no expression at all, whereby the vector is useful for expressing the exogenous DNA before activation, before and when or after activation, after activation, or not at all, such that the vector can be a selectable cloning and/or cloning and expression vector.

Indeed, multiple cellular generations expressing the exogenous DNA can provide a source of the product without lysis problems. Simply cloning the exogenous DNA by multiple cellular generations or subsequent activation with optional expression on or during activation can mean an exponential product yield of the expression product, or even just of the cloned DNA; or of both the expression product and the cloned DNA.

Further, the observed strength of the pag1 promoter and fragments thereof presents the opportunity of increased expression when exogenous DNA is operably linked thereto and this is either a chimeric or multiple insertion into a suitable vector, e.g., Baculovirus such as Hz-1 or ACMNPV. Indeed, as discussed and shown in the Examples and Figures, the pag1 promoter and fragments thereof can be employed in the non-essential polyhedrin region of AcMNPV with such surprisingly increased expression as well as a Hz-1 virus expression system.

Moreover, the early to very early nature, e.g., the onset of expression by use of the pag1 promoter or fragments thereof within 30 minutes post infection means that the virus vector has the opportunity for expression without productive replication when administered to other than a natural host of the virus, since cellular defense mechanisms which terminate productive viral replication or terminate cellular activities may achieve such termination later than 30 minutes post infection. Thus, recombinant Baculovirus, e.g., AcMNPV, Hz-1 virus or herpes virus employing pag1 promoter or fragment thereof may be useful for expression in other than insect cells, e.g., vertebrate, such as avian or mammalian cells, without productive replication. Suitable recombinant viruses and host cells for this exciting embodiment may be selected on the basis of the normal duration of the cellular mechanisms to terminate productive viral replication of a non-recombinant virus or to terminate cellular activities, post infection.

Recombinant Baculoviruses that express foreign genes are constructed by way of homologous recombination between Baculovirus DNA and chimeric plasmids containing the gene of interest. Recombinant viruses can be selected by hybridization, marker or other expression, or plaque morphology, and selected viruses can be plaque purified (a type of cloning) for homogeneity. Baculoviruses, with *Ac*MNPV being a prototypic Baculovirus, replicate in insect cells, including cell lines derived from the fall armyworm (*Spodoptera frugipenda* [Lepidoptera Nactuidae]) e.g., *Sf*900+, *Sf*9, and cells from *Bombix mori, Galleria mellanoma*, Trichplusiani or *Lamanthria dispar*. Upon productive infection of Hz-1 virus in insect cells, more than 100 different viral transcripts are expressed and eventually most of the infected cells die by necrosis. However, a very small proportion of the infected cells, usually less than 0.2%, become persistently infected. Although tremendous amount of viral transcripts were expressed during productive viral infection, all of them becomes undetectable except a 2.9 kb RNA species, the persistence-associated transcript 1 (PAT1) (Chao et al., 1992), keeps on expressing.

To obtain the inventive promoter and fragments thereof, the region used to transcribe PAT1 within the EcoRI-M fragment of the Hz-1 viral genome was localized. The pag1 gene which transcribes PAT1 was cloned and its sequence analyzed. Polysome fractionation experiments show that PAT1 does not associate with ribosomes and is primarily found to be localized in the nucleus. PAT1 is a novel viral transcript which likely does not have a protein-coding potential and is likely to be functional at the RNA level. This may be the most compelling evidence that pag1 not encode a protein. Despite these unusual feature, the pag1 promoter surprisingly was found to drive protein-coding sequences such as luciferase and lacZ genes. These findings demonstrate that non-protein-coding and nuclear localization of PAT1 is not due to a unique feature or position effect of the promoter in the nuclear matrix. In addition, since the pag1 is a very strong promoter which can be constitutively expressed in different infection cycles of the virus, it is very useful for the expression of foreign proteins, including in the Baculovirus expression system.

pag1 is localized in a heavily transcribed region during productive viral infection; thus, prior efforts at trying to delete the gene to analyze its function had failed. By blocking the function of PAT1 by using antisense RNA, a function for pag1 may be elucidated. Indeed, pag1 may be essential during productive and/or persistent viral infection. Thus, the identification of pag1 fragments thereof and vectors employing them, including for driving expression of exogenous coding DNA, is especially surprising. Nonetheless, given transcription of PAT1 during persistent infection it is therefore within the ambit of the skilled artisan from this disclosure, without undue experimentation, to operably link exogenous DNA to the pag1 or promoter or fragment thereof, or restriction sites for insertion of such exogenous DNA, for useful expression in a vector such as Baculovirus such as Hz-1 virus or ACMNPV, for expression or cloning, with or without persistency.

As discussed above, the invention comprehends a vector which can include exogenous or heterologous nucleic acids or nucleotide sequences, e.g., DNA, including coding DNA, methods for obtaining expression from the vector, compositions, and methods and products from the compositions.

In particular, the nucleotides of this invention encoding pag1, PAT1, the promoter thereof or a fragment thereof, alone, or with exogenous DNA or RNA either as a chimeric insert or multiple insertions, can be inserted into any suitable vector system for expression. For instance, the nucleotides can be inserted into any suitable bacterial vector system such as the *E. coli* system, employing known methods (see, e.g., Robbins, EPA 0162738A1; Panicali, EPA 0261940A2).

The nucleotides can be inserted into any suitable phage or viral vector system such as lambda, poxvirus, herpesvirus (see Roizman, U.S. Pat. No. 4,769,331, incorporated herein by reference), Baculovirus (see the U.S. Patents and other documents cited under Background of the Invention), polio virus (see Kitson et al., J. Virol. 65, 3068–3075, 1991, incorporated herein by reference), and adenovirus (see Grunhaus et al., 1992, "Adenovirus as cloning vectors," Seminars in Virology (Vol. 3) p. 237–52, 1993; Ballay et al., EMBO Journal, vol. 4, p. 3861–65; Graham, Tibtech 8, 85–87, April, 1990; Prevec et al., J. Gen. Virol. 70, 429–434, each of which is incorporated herein by reference) systems employing known methods.

The Baculovirus system, e.g., *Ac*MNPV or Hz-1, is preferred, with *Ac*MNPV presently most preferred especially since *Ac*MNPV is prototypic, and the polyhedrin region non-essential, and infected cells usually survive longer.

*Ac*MNPV does not naturally contain pag1 gene. Although the virus was reported to establish persistent infection in natural insect populations, no one heretofore succeeded in establishing in vitro persistent infection in insect stocks or cell lines. In addition, since several other transcripts also run across pag1 coding region during productive infection, the construction of pag1-deleted or inactivated mutant of Hz-1 virus may be extremely difficult to achieve and possibly lethal to the virus; but, this does not exclude operably linking exogenous DNA to pag1, or the promoter thereof or a fragment thereof, in Hz-1, either in the pag1 region such that it is not necessarily inactivated or deleted, or in a nonessential region of the Hz-1 virus genome.

The *Ac*MNPV containing pag1 or the promoter thereof or a fragment thereof ("*Ac*PAG") were used to infect SF9 cells. The yield of viral progenies of these recombined viruses was not significantly different from the wild type *Ac*MNPV and the yield of *Ac*MNPV viral progeny is not interfered by pag1 gene. SF9 cell was challenged with *Ac*pag1 or *Ac*MNPV viruses by moi=10. The progenies which were released into media were collected and their titers tested. The yielded recombined viruses were not significantly different from the wild type *Ac*MNPV, indicating that pag1 does not interfere with the infection of *Ac*MNPV. Since persistently infected cell clones were neither found upon the infection of *Ac*PAG virus nor found upon the infection of wild type *Ac*MNPV, pag1 may not necessarily be solely responsible for the establishment of persistent viral infection but, this does not exclude obtaining recombinant persistently infecting viruses from use of pag1, the promoter thereof or a fragment thereof.

*Ac*PAG and wild type viruses were used to infect *Bombyx mori* ("*Bm*") cells, a non-host cell of *Ac*MNPV. However, *Ac*MNPV can enter this cell and express its early gene. This viral internalization and early gene expression kills *Bm* cells when the infection dosage is high. When the dosage of ACMNPV is low, the killing of the *Bm* cell is not detectable (Kamita and Maeda, 1993; Maeda et al., 1993). No significant changes were detected between the infection of *Ac*PAG viruses and the wild type *Ac*MNPV were found when low dosage (moi=0.1, no *Bm* cell killing) or high dosage (moi=10, all *Bm* cells were killed) were used. Recombinant virus *Ac*pag1 was used to compare the cytocidal effect with wild type virus *Ac*MNPV by calculating the survival/propagation cells after virus infection. However, significant differences were observed when moi=1 were used. At this dosage, almost all the *Bm* cells were killed by *Ac*PAG viruses. pag1 may somehow enhance killing capability of *Ac*MNPV in challenging *Bm* cells, but nonetheless, expression in non-hosts, in general, preferably without productive replication of the virus, and any enhancement in *Bm* killing is not seen as disadvantageous.

By using a similar procedure as used in the establishment of a cell line which is persistently infected with Hz-1 virus by serial high multiplicity of infection (moi) passages as described in the examples below, cells persistently infected by *Ac*MNPV can be established. Insects that are persistently infected with *Ac*MNPV were reported. Accordingly, establishing persistently infected *Ac*PAG cell lines, even such cell lines wherein pag1 , its promoter or a fragment thereof is operably linked to exogenous DNA are within the ambit of the skilled artisan from this disclosure. In particular, since *Ac*MNPV is the best studied Baculovirus with the entire genome sequenced, the responsive gene (deleted in this case) for the establishment of persistent viral infection can be identified without undue experimentation by examining the deletion sites in the genome of DI particle.

After growing the bacteria or infecting cells with the recombinant virus, the protein(s) from the exogenous are collected by known techniques such as chromatography (see e.g., Robbins, EPA 0162738A1; Panicali, EPA 0261940A2); Richardson, supra; Smith et al., supra; Pennock et al., supra; EP Patent Publication No. 0265785 and the U.S. Patents cited in the Background of the Invention).

The collected protein(s) can then be employed in a vaccine, antigenic or immunological composition which also contains a suitable carrier.

Alternatively, the viral vector system, especially the preferred Baculovirus vector system, can be employed in a vaccine, antigenic, immunological, insecticide or pesticide composition which also contains a suitable carrier.

Additionally, the inventive vectors, e.g., recombinant Baculovirus and the expression products therefrom can stimulate an immune or antibody response in animals. From those antibodies, by techniques well-known in the art, monoclonal antibodies can be prepared and, those monoclonal antibodies or the antigen(s), can be employed in well known antibody binding assays, diagnostic kits or tests to determine the presence or absence of antigen(s) and/or antibodies therefrom or the presence or absence of the natural causative agent of the antigen or, to determine whether an immune response to that agent or to the antigen (s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Antigenic, immunological or vaccine compositions typically can contain an adjuvant and an amount of the recombinant virus or expression product to elicit the desired response (it being noted that an antigenic, immunological or vaccine composition containing a recombinant virus expressing a product detrimental to growth or development of insects, with insects being a natural host of the virus, is also an insecticide or pesticidal composition. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as "NOVASOME" lipid vesicles (Micro Vescular Systems, Inc., Nashua, N.H.) should also be useful.

The composition may be packaged in a single dosage form for immunization by parenteral (i.e., intramuscular, intradermal or subcutaneous) administration or orifice administration, e.g., perlingual (i.e., oral), intragastric, mucosal including nasopharyngeal (i.e., intranasal) intraoral, intraanal, intravaginal, and the like administration. The effective dosage and route of administration are determined by the nature of the composition, by the nature of the expression product, by expression level if recombinant virus is directly used, and by known factors, such as age, sex, weight, condition and nature of host, as well as $LD_{50}$ and other screening procedures which are known and do not require undue experimentation. A carrier can be water or a buffered saline, with or without a preservative. The expression product or recombinant virus may be lyophilized for resuspension at the time of administration or in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148.

Microencapsulation has been applied to the injection of microencapsulated pharmaceutical to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Example of useful polymers are polycarbonates, polyesters, polyurethanes, polyorthoesters and polyamides, particularly those that are biodegradable.

A frequent choice of a carrier for pharmaceutical and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceutical including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology,* 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginate, polyvinylpyrrolidone (PVP), methyl cellulose) and the solvent removed by either drying in vacuo or solvent extraction.

Thus, solid, including solid containing liquid, liquid, and gel (including "gel caps") compositions are envisioned.

For insecticidal or pesticidal compositions, the vector or expression products therefrom can be in a suitable agriculturally acceptable carrier or diluent. Such compositions can include customary auxiliaries or agents, and be formulated to maintain an amount of moisture or other substance for a period after application so as to enhance vector viability in the field (especially if vector used). Application rates, and crops, foliage or plants for application thereto, can be determined without undue experimentation, considering the expression product of the vector, and vector (if used) and the amount and rate of expression from the vector (if used). Application rates presently employed for such expression products, or for vectors expressing such products, or of the vector itself, may be used in the practice of this invention; or, such application rates of the vector so as to achieve expression of the products at rates analogous to rates presently used for such expression products (including from in vitro expression) may be used. Reference is made to U.S. Pat. Nos. 5,180,581, 5,266,314, 5,352,451 and 5,420,031 which involve insecticidal viruses, and, to U.S. Pat. No. 5,169,784 which relates to a recombinant Baculovirus said to be capable of being designed to produce a pesticide.

The following non-limiting Examples are given by way of illustration only and are not to be considered a limitation of this invention.

EXAMPLES

Example I

The identification and analysis of the promoter of pag1

Hz-1 virus can establish both productive and persistent infections in several lepidopteran cell lines (Burand et al., 1986). Upon productive infection of insect cells, more than 100 different viral transcripts are expressed and eventually most of the infected cells die by necrosis. However, a very small proportion of the infected cells, usually less than 0.2%, become persistently infected. In these cells, only one 2.9-kb viral transcript is expressed and it was named the persistence-associated transcript 1 (PAT1) (Chao et al., 1992).

Previously, the region transcribing PAT1 was localized within the EcoRI-M fragment of the Hz-1 viral genome (Chao et al., 1992). This invention involves the persistence-associated gene 1 (pag1) which encodes PAT1 which has been cloned and characterized. Applicant demonstrates that pag1 is unique in that it contains no significant open reading frames.

MATERIALS AND METHODS

Cell lines. Parental cells—TN368 was derived from *Trichoplusia ni* (Hink, 1970) and the other two cell lines, SF21-AE and SF9, were from *Spodoptera frugiperda*. Persistently infected cells—TNP3 (Chao et al., 1992) were the TN368 cells persistently infected with Hz-1 virus. All the cells were maintained at 26° C. in TNM-FH medium supplemented with 8% fetal bovine serum (GIBCO/BRL Inc., USA). *Bombyx mori Bm*N cells were propagated in IPL41 medium (GIBCO/BRL Inc. USA). *Drosophila melanogaster* SL-2 cells were propagated in Drosophila Schenider medium (GIBCO/BRL Inc., USA). All these media were supplemented with 8% fetal bovine serum.

DNA sequencing, primer extension, and Rnase protection analysis. Nested deletion clones were constructed in both directions from viral genomic EcoRI-M fragment using an exonuclease III/mung bean nuclease technique (Henikoff, 1984). The nucleotide sequence was determined directly from double-stranded plasmid DNA by the dideoxynucleotide chain termination method (Chen and Seeburg, 1985). Both strands were sequenced, and each base was sequenced at least twice. Computer ORF analysis of pag1 was done by using the Sequence Analysis Software Package of the Genetics Computer Group (University of Wisconsin, Biotechnology Center). Clusters of direct repeats were analyzed by self-comparison analysis of the pag1 sequence using a Dotplot program of the same software package.

The transcription start site was determined by primer extension. A 35-bp primer from nucleotides 1109(3') to 1143(5'), antisense to PAT1, was used. Total RNAs extracted from both productively infected TN368 cells and persistently infected TNP3 cells were used as templates for the experiments.

The 3' end of PAT1 was mapped by Rnase protection assays. Plasmid pHzEM-C which contains the sub-fragment C of EcoRI-M of the viral genome was used (FIG. 1A). Antisense probes were transcribed using T3 polymerase from Phzem-C, which was restricted with HpaI, and hybridized to the total RNAs (30 ug) from persistently infected cells. After Rnase A and T1 digestion, the protected fragments were fractionated on 6% polyacrylamide/urea gels.

RESULTS

No significant ORFs except clustered repeated sequences were found in PAT1. Previously we showed that the PAT1 sequence resides in the EcoRI-M fragment of the viral genome (Chao et al., 1992). This fragment was further sub-divided into A, B, C, D, and E fragments using the restriction enzyme KpnI (FIG. 1A). The PAT1 region including the putative promoter region was sequenced (FIGS. 1A, 1B). The initiation and termination sites of PAT1 have been roughly analyzed previously using Rnase protection assay in an agarose gel. The 5' end of PAT1 was found to be located in fragment B, and the 3' end of PAT1 was found to be located in fragment C (FIG. 1A and Chao et al., 1992).

Figure 2A:
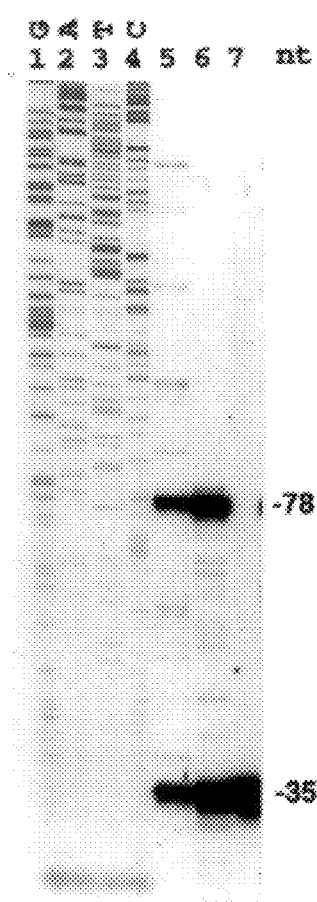
FIG. 2(A): Primer extension was used to determine the transcription start site of PAT1. Lanes 1–4 are sequence ladders; extended (78 bp) or primer (35 bp) bands derived from total RNAs which were extracted from both productively infected TN368 (lane 5) and persistently infected TNP3 (lane 6) cells are shown. Labeled primer was loaded to mark its size (lane 7).
Figure 2B:
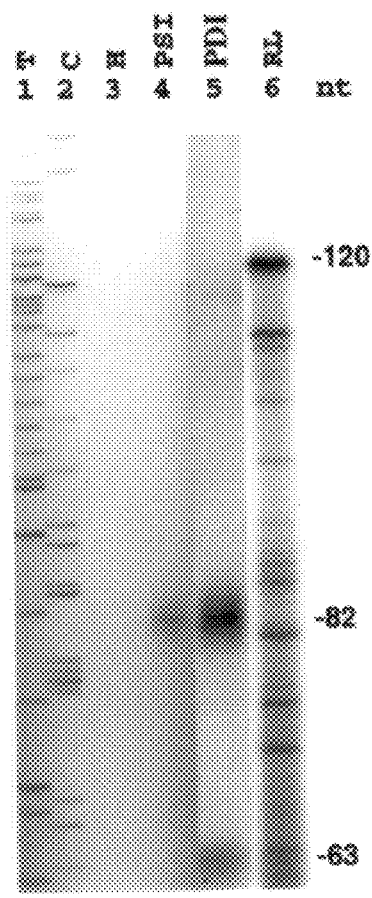
FIGS. 2(B): Rnase protection was used to map the 3' end of PAT1. In order to generate a $^{32}$P-labelled single-stranded RNA probe, a plasmid containing the sub-fragment C from viral EcoRI-M fragment (FIG. 1(A)) was constructed. This plasmid was further digested with HincII site and $^{32}$P labelled by in vitro transcription using bacteria phage T3 polymerase. Total RNAs extracted from both healthy and persistently infected TNP3 cells were protected and subjected to PAGE analysis. Two sets of size markers were used, lanes 1 and 2, and lane 4 are DNA and RNA size markers, respectively. Although nothing was protected from RNA extracted from healthy cells (lane 3), three closely associated bands were protected from productively infected TN368 (lane 4) and persistently infected TNP3 (lane 5) cells. The size of the major protected 82 bp band is marked.

To position both the 5' and 3' ends of PAT1 precisely, primer extensions and Rnase protection analyses in a high resolution polyacrylamide gel were performed. A 78-bases extended product was resulted from primer extension experiment (FIG. 2A) using a 35-base primer beginning from position 1143 (FIG. 1A) which showed that the transcript is initiated from nucleotide A at position 1066. This position is very close to a conserved transcription start sequence, CAGT, of Baculovirus early transcripts (FIG. 1B). Twenty-seven bases upstream from this start site is a typical TATA box of the RNA polymerase II transcription system; 56 bases from the transcription start site is a GATA (TTATC) motif; and 76 bases upstream from the transcription start site is a typical CAAT box (FIG. 1B). Multiple bands with a main band at the 82-base position were protected by the Rnase protection experiment (FIG. 2B). The transcription termination site of PAT1 was thus mapped to a nucleotide C at position 4002 (FIG. 1B). A putative poly-A signal, AATAAA, was detected 18 bases upstream from the 3' termination site. However, this signal seems to have no function to the PAT1 since this transcript contains no poly (A) tail (Chao et al., this issue).

To determine whether PAT1 contains a protein-coding region, pag1 was subjected to ORF computer analysis. There was no significant ORF in any forward or reversed translation frames found (FIG. 3A). GCG Dotplot analysis showed that pag1 contains several clustered direct repeats. These repeats are primarily organized into 3 clusters within nucleotides in the 1400–1550, 1800–2000, and 2100–2200 regions (FIG. 3B and C). The lack of a significant ORF together with unusual clustered repeats suggest that PAT1 may not encode a protein.

Example II

The pag1 is driven by a short and very strong promoter which is capable to drive protein-coding foreign genes Differential viral gene expression has been previously elucidated during both productive and persistent infections of the Hz-1 virus in insect cells. In spite of numerous viral transcripts being expressed during productive viral infection, the persistence-associated transcript 1 (PAT1) is the only one detectable during viral persistency. The promoter which drives PAT1 has been identified. It was found that both upstream and downstream sequences from the transcription start site (+1 bp) are necessary for promoter activity. A downstream region from +1 to +29 bp is required for the best promoter activity. Although the upstream region is important for promoter activity, a region from +1 to –90 bp, which includes a typical TATA box at –27 bases from the transcription start site, was found to be crucial for strong promoter activity, suggesting that PAT1 is driven by this closely associated promoter and is not an intron of other Hz-1 viral transcripts. Applicant shows that a short DNA fragment from –90 to +29 bp possesses an extremely strong promoter activity. Such a short promoter is stronger than polyhedrin and actin promoters in transient expression systems, suggesting that it is a novel promoter with biotechnological potential.

MATERIALS AND METHODS

Analysis of the promoter region of pag1. Nested deletions in the promoter region of pag1 were generated by polymerase chain reactions. These synthesized fragments were then ligated to the upstream of a full-length lacZ coding sequence in the plasmid PTSV-2 (Lee et al., 1995). All the regions generated by polymerase chain reactions were confirmed by DNA sequencing. Then $5 \times 10^5$ SF9 cells were cotransfected with two different plasmids. One was the plasmid PTSV-2 containing nest-deleted pag1 promoters and an intact lacZ coding sequence (1 ug). The other was a construct containing a chloramphenicol acetyltransferase (CAT) coding sequence driven by the Drosophila actin promoter (0.25 ug). The latter construct was used as an internal control to normalize the efficiency of transfection. The results of these experiments are shown in Table 1 and FIGS. 5 and 6A and 6B.

Plasmids for the assay of different promoters. The plasmid vector used in this experiment, PTSV-2, contained an intact bacteria lacZ gene downstream to a unique HindIII site for insertion of different promoters (Lee et al., 1995). Promoters used were pag-727 and pag-90 from pag1 promoter; IEO, IE1, and polyhedrin promoters from the genome of AcMNPV (Lee et al.,1995); and three promoters other than Hz-1 virus or AcMNPV also used for comparisons. These three are the actin promoter from D. melanolgaster (Han et al., 1989) and SV40 late (Templeton and Eckhart, 1984) and CMV immediate early (Wilkinson and Akrigg, 1992) promoters from mammalian viruses. All these constructs (0.5 ug) were co-transfected with Pactin-CAT (0.0625 ug), which contained an E. coli CAT gene under the control of the D. melanogaster actin promoter, as an internal control. When polyhedrin promoters were co-transfected with viral DNA, 0.58 ug of the AcMNPV genomic DNAs were used. The results are shown in FIG. 7.

RESULTS

Figure 4:
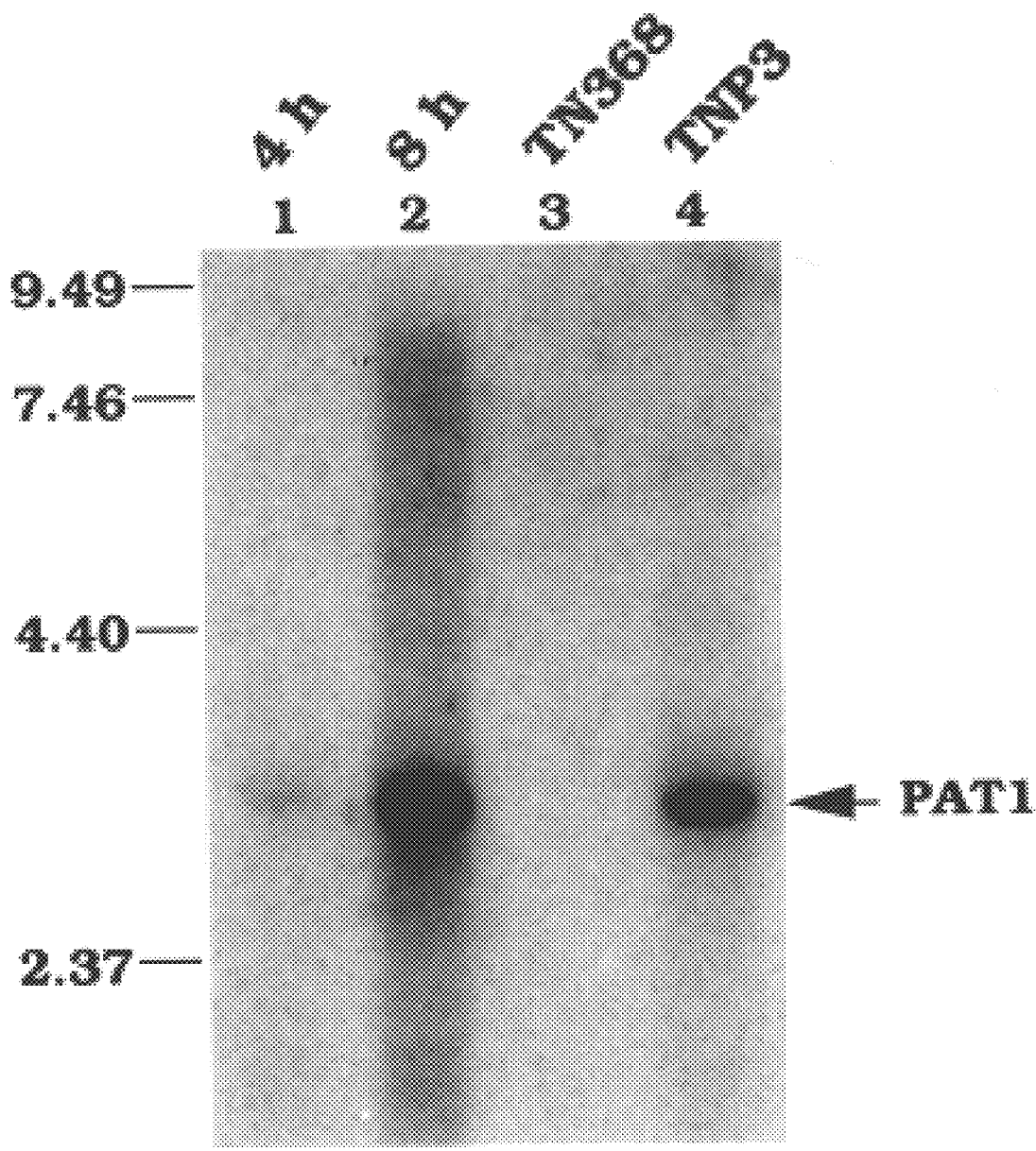
FIG. 4 shows: Transfection of pag1 into host cells indicating that viral factors are not required for the transcription of PAT1. Plasmid pHzE-M (Chao et al., 1992) which contains the entire pag1 gene was transfected into the host cell. After transfection, total RNAs were harvested and analyzed by Northern hybridization. PAT1 signals can be found at 4 and 8 h after transfection. Total RNAs harvested from parental TN368 and persistently infected TNP3 cells were also used as negative and positive controls, respectively.

Viral factor is not essential for pag1 transcription. It was previously shown that PAT1 can be detected from a very early stage during productive viral infection and is the only viral-specific transcript expressed during persistent viral infection (Chao et al., 1992). To test whether the expression of PAT1 is independent from the expression of other viral genes, a plasmid, Phze-M, which contains only the putative promoter and PAT1 coding region (FIG. 4 and Chao et al., 1992) was transfected into the SF21 cells. At 4 and 8 h after transfection, total RNAs were extracted and analyzed by Northern hybridization. The results in FIG. 4A show that PAT1 could be detected 4 h after transfection and the intensity of the signal had increased greatly 8 h after transfection (FIG. 4). These results indicate that host factors are sufficient for the expression of PAT1.

Figure 5:
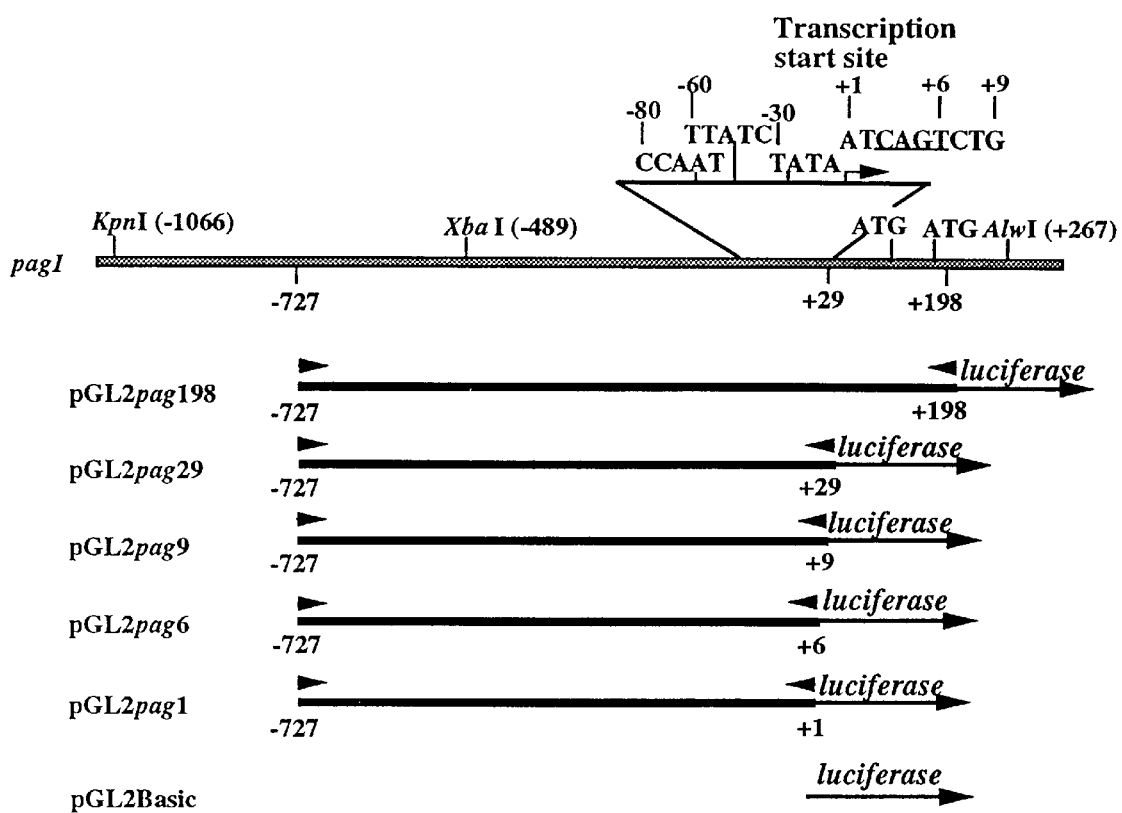
FIG. 5 shows: Definition of the region downstream from the transcription start site which is required for the promoter activity of pag1. Viral genomic DNA fragments which contain transcription start sites were nest deleted at their 3' ends. These fragments were ligated with the protein coding region of the luciferase gene and the activity of this enzyme was determined after the transfection of the constructs to an SF9 cell. All of these constructs were co-transfected with a construct containing a Drosophila actin promoter-driven CAT gene to serve as controls.
Figure 6A:
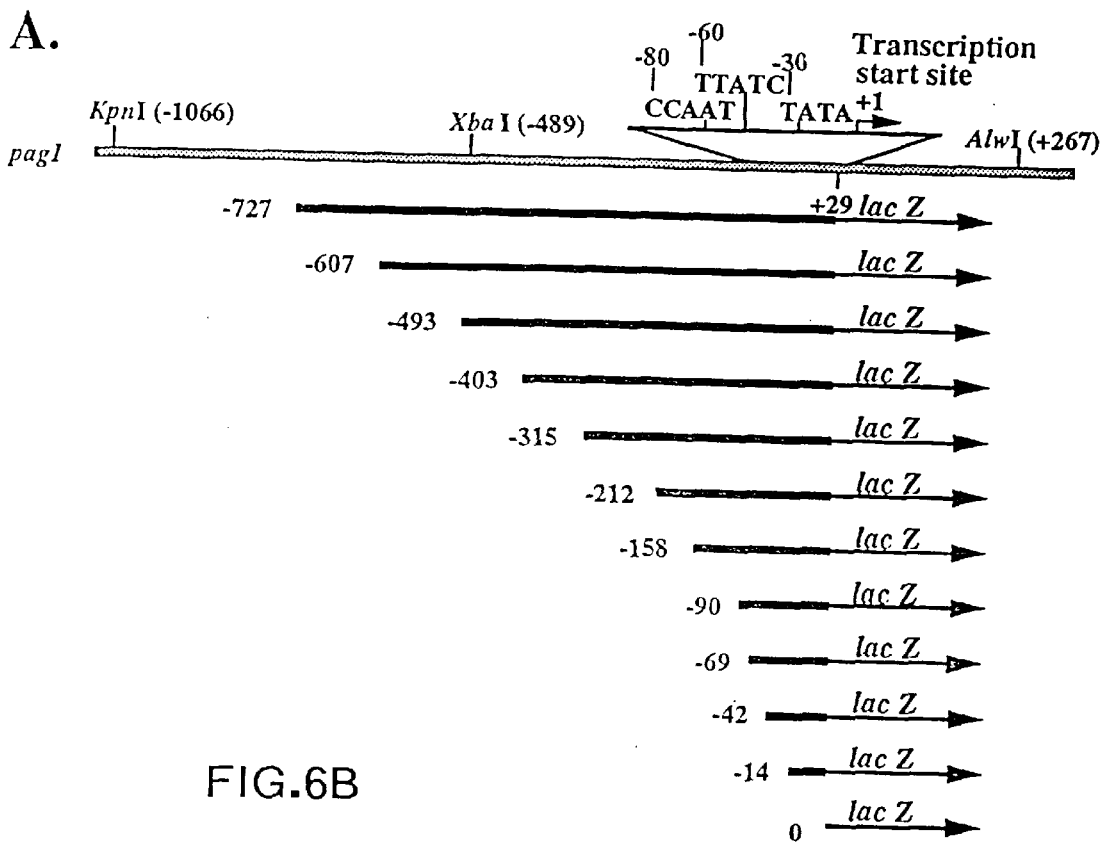
FIG. 6(A): Viral genomic DNA fragments which contain transcription start sites were nest deleted at the 5' ends. All these fragments were ended at +29 bp and further ligated with the protein coding region of the lacZ gene. CAAT and TATA boxes and the GATA (TTATC) motif are shown.

The identification of pag1 promoter. To further characterize the promoter of pag1, both upstream and downstream sequences from the transcription start site were analyzed. Regions between –727 and various positions of +1, +6, +9, +29 and +198 were cloned and fused to a luciferase gene (FIG. 5). The activity of luciferase was analyzed after transfection of these constructs. The results showed that a sequence contain between nucleotides –727 and +1 gave rise to weak, some, albeit luciferase activity. The luciferase activity gradually increased when the 3' end of the promoter regions included were increased up to nucleotide +29. However, the promoter activity dropped significantly upon further increase of the promoter region to nucleotide +198, the interval from nucleotides +29 to +198 contains two ATG codons (Table 1). The results showed that nucleotides +1 to +29 bases region downstream of the transcription start site are important for the best expression of the ligated luciferase gene (Table 1 and FIG. 5).

Figure 6B:
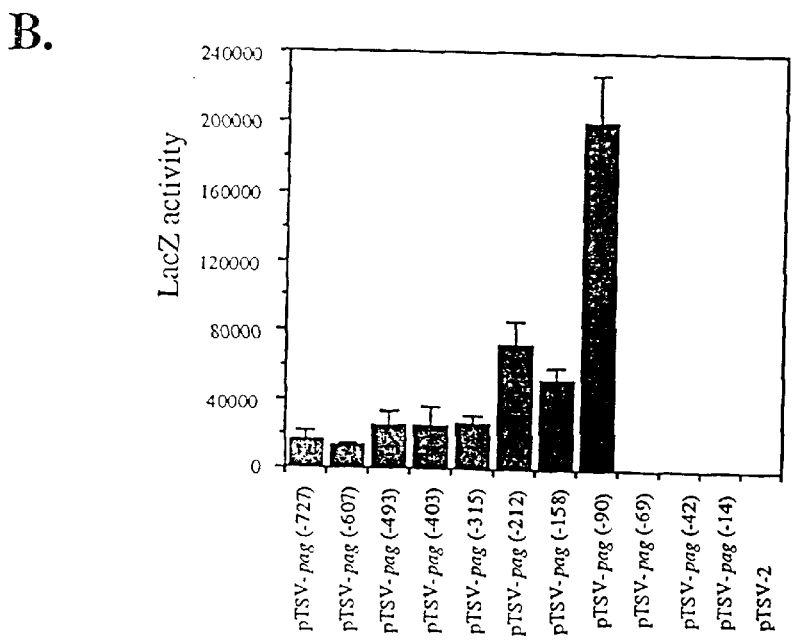
FIG. 6(B): Following transfection of the constructs to an SF9 cell, the activities of lacZ were determined. The transfection of all these constructs were co-transfected with a construct containing a Drosophila actin promoter-driven CAT gene to serve as controls. One unit of lacZ activity is equal to the intensity emitted by 0.1 Nm 4-methylumbelliferone.
Figure 7A:
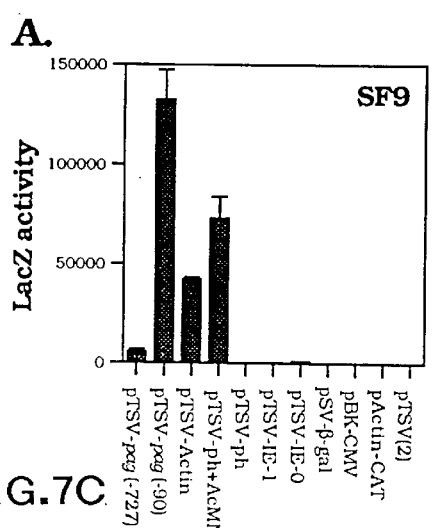
FIG. 7 contains (A), (B), (C), and (D) and shows: Promoter activity comparisons between pag1 and other promoters in SF9 cells. The lacZ protein coding region in plasmid pTSV-2 is expressed by miscellaneous promoters including full-length (pag-727) or deleted (pag-90) pag1, actin, polyhedrin (ph), polyhedrin plus virus (ph+AcMNPV), immediate early gene 1 (IE-1) and immediate early gene 0 (IE-0) of AcMNPV, SV40 (pSV-b-gal), and CMV-IE (CMV) promoters in SF9 cells. Plasmids pActin-CAT and a promoter-less PTSV-2 are controls. One unit of lacZ activity is equal to the intensity emitted by 0.1 Nm 4-methylumbelliferone.
Figure 7B:
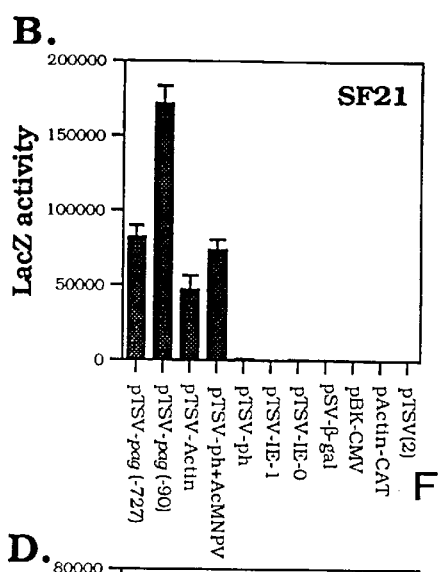
Figure 7C:
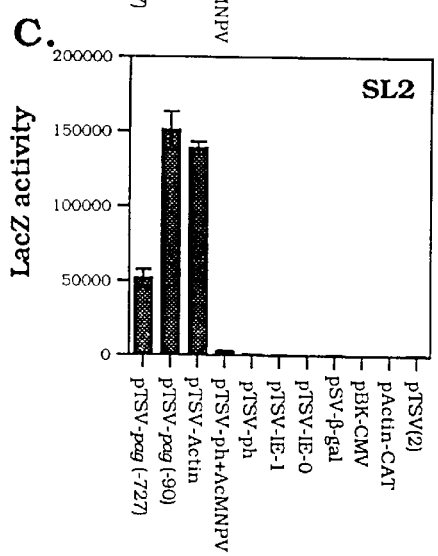
Figure 7D:
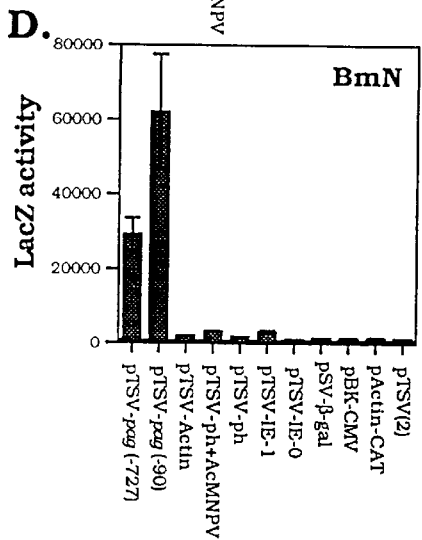

To analyze the upstream sequence needed for promoter activity, a region between nucleotides –727 and +29 which was ligated with a LacZ coding sequence, was constructed. Plasmids which contained nest-deleted sequences upstream from the transcription start site to a fixed position +29 (see FIG. 6A) were transfected separately into SF9 cells. After transfection, the intensity of lacZ expression from individual promoter deletion constructs was analyzed. Similar levels of promoter activity were observed in the promoter constructs containing regions from nucleotides −727/+29 to −315/+29. The promoter activity increased when the construct was deleted up to nucleotide −212. Interestingly, when the construct was further deleted to nucleotide −90, which still retained the putative CAAT and TATA boxes and a GATA motif, the strongest promoter activity was observed. These expression patterns indicate a distinctive control mechanism for the pag1 promoter, suggesting that a repressor and/or activator may be utilized during viral infection. Further deletion into the nucleotide −90/+29 region abolished the activity of the promoter, indicating that the closely associated TATA box, and CAAT and GATA motifs are crucial for PAT1 expression (FIG. 6B). Therefore, PAT1 expression appears regulated by a strong promoter in the −90/+29 region, and the promoter which contains only this region is denoted as the pag-90 promoter. PAT1 is expressed from a promoter which is unlikely to be an intron of other viral transcripts.

The comparison of promoter activity between pag1 and other genes. Since the promoter of pag1, especially the pag-90 promoter, is strongly expressed in insect cells, many other promoters were collected and compared. The activity of several promoters of insects, insect viruses, and mammalian viruses were compared with that of pag1 promoter by DNA transfection in insect cells using a vector PTSV. The PTSV is a promoter-less construct which contains an intact lacZ gene ready to be expressed in bacterial and insect cells by the insertion of functional promoters inserted to the convenient HindIII site (Lee et al 1995). The results are shown in FIG. 7. Although the SV40 (Templeton, and Eckhart, 1984) and CMV (Wilkinson and Akrigg, 1992) promoters are strong promoters in mammalian systems, they are not strongly expressed in insect cells. The actin promoter of Drosophila (Han et al., 1989) was strongly expressed in most insect cells tested except in the silkworm BmN cells. The activity of the actin promoter was stronger than the full-length pag1 promoter in SF9 and Drosophila SL2 cells, however, it is weaker than pag-90 in all cells tested, including the SL2 cells where the actin promoter was originally derived.

AcMNPV is a typical Baculovirus used for Baculovirus expression systems. The early promoters of AcMNPV, like IE1 and IE0 (Chisholm and Henner, 1988), were not strongly expressed in any of the tested cells. The polyhedrin promoter of AcMNPV is a very strong promoter and the major promoter for the expression of a large quantity of foreign proteins using the Baculovirus expression system. Because the polyhedrin promoter is a very late promoter, it was not properly expressed when transfected into the cells alone. However, upon co-transfection of the polyhedrin promoter-driven PTSV-2 (PTSV-ph) with purified viral genomic DNA, the activities of the polyhedrin promoter were enhanced drastically in SF9, SF21, and BmN cells. Even so, the activity of the polyhedrin promoter was still not as strong as the pag-90 promoter in any of the tested cell lines (FIG. 7).

DISCUSSION

These experiments illustrated many interesting and unique results. It was found that during persistent Hz-1 virus infection most of the productive-specific transcripts are turned off leaving PAT1 as the only detectable viral transcript (Chao et al., 1992). Although such phenomenon has only been reported in the infection of Hz-1 virus among insect viruses and also uncommonly observed in the infection of other viruses, the differential viral gene expression during productive and latent/persistent viral infection of DNA viruses has been best studied in the infection of herpes viruses in mammals.

Thus, given the similarity in replication between herpes virus and Baculovirus (nuclear replication) and of a latency or persistent infection, use of pag1, the promoter thereof, and fragments thereof, especially operably linked to exogenous DNA, in herpes virus are envisioned.

The genome of herpes simplex virus type 1 (HSV-1) of mammals has the capacity to encode at least 72 unique proteins during the course of productive infection. During the latent infection, however, viral gene expression is limited to the transcription of only a latency-associated gene which gives rise to 3 nuclear-localized LATs (Spivack and Fraser, 1987, and Stevens et al, 1987). Mutation analysis has demonstrated that the LATs are not responsible for the initiation of latent infection (Steiner et al 1989; Ho and Mocarski, 1989). Rather, they could be involved in HSV-1 reactivation (Dobson et al., 1989; Leib et al., 1989; Steiner et al., 1989), although contradictory results have also been reported (Block et al., 1990; Ho and Mocarski 1989). LATs are also identified as the introns of a larger unstable 8.3 kb-RNA which is transcribed only 28 bases downstream from the promoter (Zwaagstra et al. 1990). This result at least partially resolves the puzzle as to why the promoter predicted for the LATs is over 660 bases upstream from their 5' ends.

Although pag1 is situated in a heavily transcribed region (Chao et al, 1992), PAT1 is not an intron of another longer transcript for several reasons. 1) PAT-1, not the other 2 upstream transcripts, is the only viral-specific transcript detected during persistent viral infection. 2) Unlike LATs, the TATA box of the PAT-1 promoter is only 27 bases upstream from its transcription start site. 3) PAT-1 was readily detectable when a viral EcoRI-M fragment, which contains pag1, was transfected into virus-free cells. Fragment EcoRI-M contains only the promoter of PAT-1 but not the promoters or the transcription start sites for the 2 other longer transcripts upstream from the PAT1 coding region (Chao et al., 1992). 4) The 90-base region which contains the TATA, CAAT and GATA motifs and is juxtaposed to the transcription start site appears to be important for promoter activity. These results argue strongly that PAT1 is a viral transcript. And, these results allow the skilled artisan to fashion useful, e.g., functional fragments; for instance, by having any or all of these motifs suitably within the fragment, without undue experimentation. Further, promoter activity may reside within a 500 bases region upstream from the transcription site, thereby providing further results enabling production of useful fragments, without undue experimentation.

The experiments also indicated that pag1 is driven by a strong promoter. Interestingly, nest deletion of the promoter region showed that the activity of the promoter becomes much stronger if only the region between −90 bp to +29 bp (pag-90 promoter) is conserved. This suggests a possibility that the promoter region further upstream of −90 bp may contain sites which exhibit repressor activity. Since the repression was observed without the infection of the virus, this suggests that host cell factors play important roles for the expression of this transcript.

The polyhedrin promoter has been shown to be one of the strongest promoters of a typical Baculovirus, the *Ac*MNPV, for the expression of genetically engineered foreign proteins (Kidd and Emery, 1993; Miller, 1988; Smith et al., 1983). The strong activity of pag-90 promoter gives rise to a new, perhaps better, alternative for the expression of foreign proteins using the Baculovirus expression system.

There are many advantages in using pag-90 promoter for the expression of foreign proteins. 1) The pag-90 promoter expresses protein much earlier; pag-90 is expressed immediately right after viral infection and constitutively expressed thereafter. Therefore, the genetically engineered protein will be expressed much earlier and likely to cumulate more protein products compared with the very late promoter of polyhedrin. 2) The pag-90 promoter is short; pag-90 is about as short as the promoter of polyhedrin (Possee and Howard, 1987) which makes cloning easy. 3) Early expression may generate better proteins. Early expression of foreign proteins avoids the effect of host translation shut off and thus better protein modification can be achieved (Chazenbalk and Rapoport 1995). 4) Permanent, strong foreign protein-expression cells can be established. The pag-90 promoter can direct permanent expression of foreign proteins in cell lines without the trouble of viral infection procedures and the interference of final cell lysis after viral maturation. The lysis of cells may result in degradation of target proteins in cells or releases of contaminating cellular proteins in the medium if genetically engineered secretory proteins are to be recovered. Furthermore, a protein expressed without Baculovirus could be free from the destruction of viral-encoded ubiquitin (Guarino, et al., 1995).

Example III

PAT1 is a non-coding viral RNA predominately localized in the nucleus of cells persistently infected with Hz-1 virus Hz-1 virus, also termed as Hz-1 virus (Wood and Burand, 1986; Chao et al., 1992) or Hz-1V (Burand et al., 1986), is a rod-shaped virus which contains a double-stranded circular 228 kb DNA genome (Chao et al., 1990; Huang et al., 1982). This virus was originally identified as a persistently infected virus in the *Heliothis zea* cell line, IMC-Hz-1 (Granados et al. 1978). Smith and Summers (1982) later demonstrated that Hz-1 virus has low but general DNA sequence homology with most of the tested Baculoviruses in the family Baculoviridae. Among these, the nucleotide sequence homology of Hz-1 virus is greater with viruses in the Granulosis virus group, including *Heliothis armiger* and *Plodia interpunctella granulosis* viruses. This virus was originally referred as a member of the family Baculoviridae (Wilson, 1990) and it together with other non-occluded Baculoviruses were recently removed from the family and are temporarily unclassified (Volkman, 1995).

The host range of Hz-1 virus is broad. Insect cell lines from 5 lepidopterans, including *Trichoplusia ni* (TN368), *Spodoptera frugeperda* (IPLB-SF-212), *H. zea* (IPLB-1075), *Mamestra brassicae, Porthetria dispar* (IPLB-65Z), *Lymantria dispar* (LD252Y) and *H. virescens* (BCIRL-HB-AM1) are susceptible to infection (Burand et al., 1986; Lee et al., 1993; Wood and Burand, 1986). Persistent Hz-1 viral infections have been established in 3 of these insect lines: *H. zea, T. ni* and *S. frugiperda* (Chao et al., 1992; Wood and Burand, 1986; Granados et al., 1978). The Hz-1 virus is one of the very few insect viruses by which persistent viral infection can be established consistently by viral infection in the laboratory.

Previously it was reported that Hz-1 virus produces at least 100 viral-specific transcripts during productive viral infection. However, only 1 RNA species, the persistence-associated transcript 1 (PAT1), is detectable during persistent viral infection (Chao et al., 1992). In insects, the differential viral gene expression during productive and persistent viral infections had only been demonstrated in the case of Hz-1 virus. It is rather similar to the case of herpes viruses of mammals.

Persistent viral infection in insects has been reported frequently from either field collection or laboratory stocks. This persistence is usually known after dramatic onset of virus epizootics in nature or in the laboratory stocks (Burand et al., 1986; Chao et al., 1986; Hughes et al., 1993).

This invention involves characterization of the persistence-associated transcript PAT1 and that it is not associated with ribosomes but, instead, accumulates in the nucleus. These features suggest that PAT1 is a novel viral transcript which does not code for a protein and most likely functions at the RNA level.

MATERIALS AND METHODS

Cell lines. (a) Parental cells—TN368 was derived from *Trichoplusia ni* (Hink, 1970), whereas 2 other cell lines, SF21-AE and SF9, were from *Spodoptera frugiperda*. (b) Persistently infected cells—TNP3 (Chao et al., 1992) were the TN368 cells persistently infected with Hz-1 virus. All cells were maintained at 26° C. in TNM-FH medium supplemented with 8% fetal bovine serum (Gibco/BRL, Inc., USA).

Polysome fractionation. Procedures for isolation and analysis of polysomes followed Schmidt and Merrill (1991). TNP3 cells ($1\times10^7$) were lysed and subjected to sucrose gradient centrifugation. One-tenth aliquots of the fractionated RNA were assayed by Northern blotting.

Nuclear localization. Cells were first fractionated into the nuclear and cytoplasmic fractions by following the procedure of Summers and Smith (1988). Nuclear RNA was extracted from the nuclear pellets with guanidinium thiocyanate. Five micrograms of each of the resultant RNAs was serially diluted and slot blotted. Two in vitro transcribed probes containing either the PAT1 encoding gene, the persistence-associated gene 1 (pag1), from the genome of Hz-1 virus (FIG. 8) or actin sequences from the genome of Drosophila (Han et al., 1989) were used to hybridize to both Northern and slot blots.

Determination of 5' capping and 3' poly(A) tailing. Total RNA was extracted from the persistently infected cell line TNP3 (Chao et al., 1992). It was then fractionated into capped and uncapped species by using an m-aminophenyl boronate agarose (PBA) column (Sigma Co., MO, USA). A 3-ul bed volume of PBA was washed with 20 bed volumes of $H_2O$ and then with 10 bed volumes of 0.1M sodium acetate. The column was equilibrated with 7 to 10 bed volumes of binding buffer (50 Mm HEPES; Ph 8.5, 1M NaCl, 100 Mm $MgCl_2$). RNA (500 ug) was resuspended in 0.5 ml of $H_2O$ and brought to 1× with binding buffer in a final volume of 1 ml. Each sample was reloaded 10 times through the column and then rinsed with 7 to 10 bed volumes of binding buffer. RNA was eluted with a discontinuous gradient of NaCl concentrations from 0.9 Mm to 0.2 Mm at 0.1 Mm intervals and 0.5 ml per interval. Yeast tRNA was added as a carrier and samples were precipitated with ethanol.

For the determination of 3' poly(A) tailing, total RNA was extracted from TNP3 cells and MRNA was captured by "DYNABEADS" oligo $(Dt)_{25}$ (200 ul beads/75 ug RNA) following the manufacturer's instructions (Dynal A. S., Oslo, Norway). The captured and flow-through MRNAS were size-fractionated on 1% agarose gels and transferred by vacuum blotting onto "GENESCREEN" (NEN Research Products, Dupont, Inc., MA, USA). These blots were hybridized using strand-specific probes derived from either the pag1 or actin genes.

RESULTS

Figure 8:
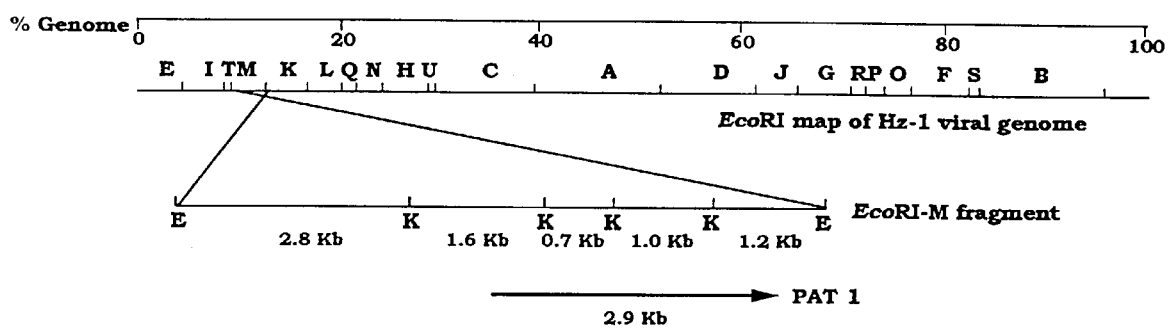
FIG. 8 shows: The location and orientation of PAT1. The circular 228 kb DNA genome of Hz-1 virus is linearlized and the EcoRI-M fragment which contains entire pag1 is further magnified. Alphabetical designations above the second line represent the EcoRI-restriction viral genomic fragments in order of decreasing size. Alphabetical designations under the third line represent restriction sites as following: E, EcoRI; K, KpnI.

PAT1 is not associated with ribosomes and predominantly localized in the nucleus. The PAT1 was encoded by the persistence-associated gene 1 which resides in the viral genomic EcoRI-M fragment (FIG. 8). Although computer program predicted that PAT1 lacks protein coding potential, supporting evidence is needed to show if PAT1 is associated with the cellular protein synthesis machinery or not. For this purpose, postmitochondrial fractions were obtained from the persistently infected TNP3 cells (Chao et al., 1992). Polysome profiles were subsequently generated by measuring the absorbency at 254 nm of fractions collected by sucrose density gradient fractionation. As a control, polysomes were dissociated from MRNA by adding EDTA. Fractions were harvested and assayed by Northern analysis. A low level of PAT1 was detected in sucrose gradient fractions with or without EDTA treatment (FIGS. 9A, 9B and 10A, 10B) indicating that PAT1 is not associated with ribosomes. In contrast, actin MRNA, which were used as translatable MRNA, was mainly detected in the heavy polysome regions (FIG. 9C). However, in the presence of EDTA, the majority of actin MRNA shifted drastically to the free ribosomes fractions (FIG. 10C).

The total signal intensities of PAT1 added up from all the postmitochondrial fractions (panels B in FIGS. 9 and 10) were found to be much lower than the total PAT1 in the RNA extracted from intact cells (the controls in FIGS. 9D and 10B) suggesting that the majority of PAT1 may not be in the postmitochondrial fractions. To identify the location of the majority of PAT1, RNAs from both isolated nuclei and pooled cytoplasmic fractions of TNP3 cells were analyzed separately in dot blots. Those results indicated that PAT1 was present almost exclusively in the nuclear fraction, with less than 1% of the PAT1 signal detected in the cytoplasm. In contrast, over 90% of the actin RNA was found in the cytoplasmic fraction (FIG. 11).

PAT1 is neither capped nor poly(A) tailed. Since PAT1 is not associated with ribosomes and is localized primarily in the nucleus (FIG. 11), it was interesting to know whether it is 5' capped and poly(A) tailed. For the determination of 5' capping, an m-aminophenyl boronate agarose column was used. The majority of PAT1 was eluted with a high-salt solution (FIG. 12A), indicating that PAT1 is not capped. For the determination of 3' poly(A) tailing, "DYNABEADS" oligo $(Dt)_{25}$ was used to capture the poly(A)-tailed RNA species. PAT1 was not well captured by "DYNABEADS" (FIG. 12B), indicating that PAT1 is either not poly(A) tailed or the poly(A) is too short to be captured by the oligo $(Dt)_{25}$ tail of "DYNABEADS".

DISCUSSION

Virus-host interactions during productive and persistent viral infection cycles are a complicated biological phenomenon. Generally, it is believed that escaping immune surveillance in vertebrates is one of the reasons why viruses enter persistency and minimize its protein expression in the host cells (Oldstone, 1989). However, these results showed that Hz-1 virus greatly reduces its transcription and essentially terminates the synthesis of all its proteins in the persistently infected insect cells. This suggests that insects, although lacking the vertebrate immune system, still exert very intense pressure on invading viruses, thus resulting in strong repression of viral gene expression during persistent viral infection. This has forced the Hz-1 virus to evolve in a way that there is no detectable expression, particularly no protein expression, except a nuclear RNA PAT1 is expressed in persistency. Thus, the damage of the viral infection to the cells is greatly reduced and at the same time the host cells can protect the persistently infected viruses from the exposure of virus or viral DNA to the severe environment.

PAT1 is unique in several aspects. There is no significant ORF in its sequence, polysome fractionation experiments indicated that it is not associated with ribosomes, it was not translated in vitro, it is neither capped nor tailed with a poly(A) sequence, and it is localized primarily in the nucleus. All evidence demonstrates conclusively that PAT1 is not translated into a protein. However, despite these unusual features, the promoter of pag1 was found capable of driving transcription of protein-coding genes strongly such as the luciferase and lacZ genes. These findings suggest that the non-protein coding nature and the nuclear localization of PAT1 are not solely due to a unique feature of the promoter.

There are a few precedents for genes which are transcribed by RNA polymerase II, but the transcripts do not code for proteins. One such case is the Hsrw gene in Drosophila melanogaster, whose transcript has been suggested to function as a translational regulator (Fini et al. 1989). A second example is an antisense RNA in Xenopus laevis, which may regulate the concentration of fibroblast growth factor MRNA (Kimelman and Kirschner 1989). A developmentally controlled gene, the lin-4, from Caenorhabditis elegans, encodes a small RNA that binds to the 3'-untranslated region of lin-14 MRNA, blocking the ability of lin-4 MRNA to make a protein (Takayama and Inouye, 1990). In sea urchin eggs and Xenopus oocytes, nontranslatable RNA containing interspersed repetitive sequence elements constitutes about 68% of the total poly (A) RNA in the cytoplasm (Calzone et al., 1988; Costantini et al., 1980) without an identified developmental function.

The mouse Xist gene, a recently described gene which maps to the X chromosome inactivation center (XIC) of female mice, is expressed only from the inactive X chromosome when the majority of the X-linked genes are inactivated (Brockdorff et al. 1992; Kay et al. 1993). The product of the mouse Xist gene is a 15-kb transcript with no conserved ORF to human XIST gene. Xist RNA is not associated with the translational machinery of the cell, and is located almost exclusively in the nucleus. Despite the apparent lack of conserved protein-coding potential, the degree of sequence conservation (76% identity) and overall comparable gene structure between mice and human suggest that this gene does have a function (Brockdorff et al. 1992; Brown, et al. 1992). A unique feature of the Xist sequence is the presence of several regions comprised of direct tandem repeats. The similarity of many repeats in both mice and humans suggests that they may have functional significance. Although the discrepancy in sizes between Xist and pag1 is significant, pag1 does contain unique clustered direct repeats (FIG. 3B, C), and is worthy of further investigation.

More recently, Askew et al. (1994) have shown that the His-1 gene, while lacking extensive ORF in the entire sequence, is a conserved single-copy gene in several vertebrate species and is expressed as a spliced and polyadenylated RNA. Thus the His-1 transcript, although its function remains to be illustrated, is believed to be another member of a family of RNA molecules that function without being translated into a protein. It may turn out that there is a whole family of regulatory RNA molecules that function in the absence of translation (Nowak, 1994), and PAT1 is a new addition from viral origin.

During latent infection of the herpes simplex virus type 1 (HSV-1), viral gene expression is limited to the transcription of only a latency-associated gene which gives rise to the latency-associated transcripts—LATs (Spivack and Fraser, 1987, and Stevens et al, 1987). The function of LATs might be involved in HSV-1 reactivation although it is puzzling that viral reactivation still takes place without having these transcripts (Dobson et al., 1989; Leib et al., 1989; Steiner et al., 1989) and they could be the introns of a larger unstable 8.3-kb RNA (Zwaagstra et al. 1990). The PAT1 is unlikely to be an intron of another longer transcript, however, since it is the only transcript detectable during persistent viral infection, stay in the nucleus, and behaves like a stable intron without obvious capping and poly(A) tailing, we can not rule out the possibility that it could be designed through evolution for similar mechanisms to exert their functions or for similar purposes as to the LATs. Due to the nature that Hz-1 virus can induce both productive and persistent viral infections in insect cell lines versus HSV1 usually only induces latent viral infection in the tissue, PAT1 could be viewed with different angles and compared with the studies of LATs in the future.

The pag1 is localized in a heavily transcribed region during productive viral infection. The study of PAT1 will contribute to the understanding of the basis of persistent viral infection of Hz-1 virus in insects. Since PAT1 is relatively small (2.9 kb) as compared with other MRNAS located in the nucleus, its study contributes useful information on nuclear RNA. In addition, although pag1 only transcribes a non-protein-encoding nuclear RNA, exogenous protein coding regions, for instance, of bacteria lacZ and firefly luciferase genes were capable being expressed using pag1 promoter when fused to the 5' end RNA coding region of PAT1 up to +198 bp. This suggests that the promoter and 5' lateral region of PAT1 is independent of nuclear localization and protein translation of the conjugated RNA sequences. Therefore, PAT1 is suitable to explore the mechanism of nuclear localization and possible nuclear/cytoplasm transportation of nuclear RNAs.

Example IV

PAT1 is a unspliced RNA without 5' capping and 3' poly(A) tailing.

During persistent Hz-1 viral infection, the expression of all productive-specific genes are turned off except the persistence-associated transcript 1 (PAT1). It was previously shown that the encoding region of PAT1 contains no significant ORFs. Furthermore, PAT1 was found to be unassociated with the cellular translation machinery and to be located exclusively in the nucleus. In these experiments, it was found that the PAT1 molecule is neither capped nor polyadenylated, and the sequence of CDNA is identical to that of the viral genomic DNA, suggesting that PAT1 is neither spliced nor further edited after transcription. However, PAT1 is not likely an intron of other Hz-1 viral transcripts due to its driven by a closely associated promoter. This evidence collectively indicates that PAT1 is a novel viral transcript which is most likely to functional at the RNA level in nucleus.

MATERIALS AND METHODS

Random-primer directed RT-PCR for the cloning of 3' end PAT1 sequence. RT-PCR was carried out using a primer which contains 2 defined recognition sequences, X and Y, and a random primer at the 3' end (5'-ACGAC GCCAC TAAAG CTTAA GGAGC TCTCT AAGTT CGAAN NNNNN-3') (SEQ. ID. NO. 26), as described by Fritz et al. (1991) and illustrated in FIG. 13A. Five micrograms of Dnase-digested total RNA from TNP3 cells was reverse transcribed in 25 ul of reaction mixture which contained 30 ng of the primer and 200 U MLV reverse transcriptase. Single-stranded CDNA was digested by Rnase A followed by ethanol precipitation. CDNA was first PCR amplified using pag1-specific primer Y12 (nucleotides 2626–2653 of pag1 sequence) and Y primer (5'-ACGCC ACTAA AGCTT AAGGA-3') (SEQ. ID. NO: 27) (See FIG. 13(A)). The 1.3-kb fragment, which was the largest one from the first PCR amplification, was gel purified and further amplified by the second PCR using LY12 (basepairs 2643–2671 of the pag1 sequence) and X primer (5'-CTTAA GGAGC TCTCT AAGTT CGAA-3') (SEQ. ID. NO: 28) (See FIG. 13B). The 1.3-kb fragment was gel purified again, cloned and its sequence determined.

Cloning of overlapping CDNA fragments by RT-PCR. CDNA fragments other than the aforementioned 3' end 1.3-kb fragment were amplified by RT-PCR. Using paired primer sets, the H, M1, M2, and M fragments were amplified, cloned, and sequenced. The region covered by the P fragment (FIG. 14, lane 2) is the promoter region which cannot be generated by RT-PCR and thus served as a negative control.

In vitro transcription and translation. Full-length CDNA of PAT1 was cloned into pBluescript vector (Stratagene, Inc., CA, USA) and named PPAT1. Plasmid PPAT1 was linearized and transcribed by the in vitro Transcription Kit (Stratagene, Inc., CA, USA) with T7 RNA polymerase following the manufacturer's instructions. The in vitro-transcribed sense RNA was translated in the uncapped form, using the Rabbit Reticulocyte Lysate Translation System (GIBCO/BRL Inc. MD, USA) and the proteins thus synthesized were analyzed by gel electrophoresis.

RESULTS

Cloning of the 3' end of PAT1. It is difficult to use conventional cloning procedures to define a transcript without having a poly(A) tail, therefore, the 3' end of PAT1 is determined using a random primer RT-PCR technique (Fritz et al., 1991). Random primers which were tailed with X and Y sequences (Fritz et al., 1991) were used to synthesize the 3' portion of PAT1 using reverse transcriptase (FIG. 13). The products were further PCR amplified using primers Y12 and Y (FIG. 13A). A 1.3-kb band, being the largest detectable fragment among multiple bands, was identified (FIG. 13B). It was sliced from the agarose gel and further amplified using LY2 and X primers. Significant amplifications of the 1.3-kb band (FIG. 13C) were isolated, cloned, and sequenced. The sequence was found to begin from nucleotide 2643 but ended at nucleotide 3915 suggesting that the 3' end of PAT1 does not extend beyond position 4002, the site mapped by Rnase protection (FIG. 2A, B). In other words, the 3' end mapped by Rnase protection is the actual termination site of PAT1 and the chance that the 3' end of the transcript comes from further downstream by splicing is unlikely.

Figure 14:
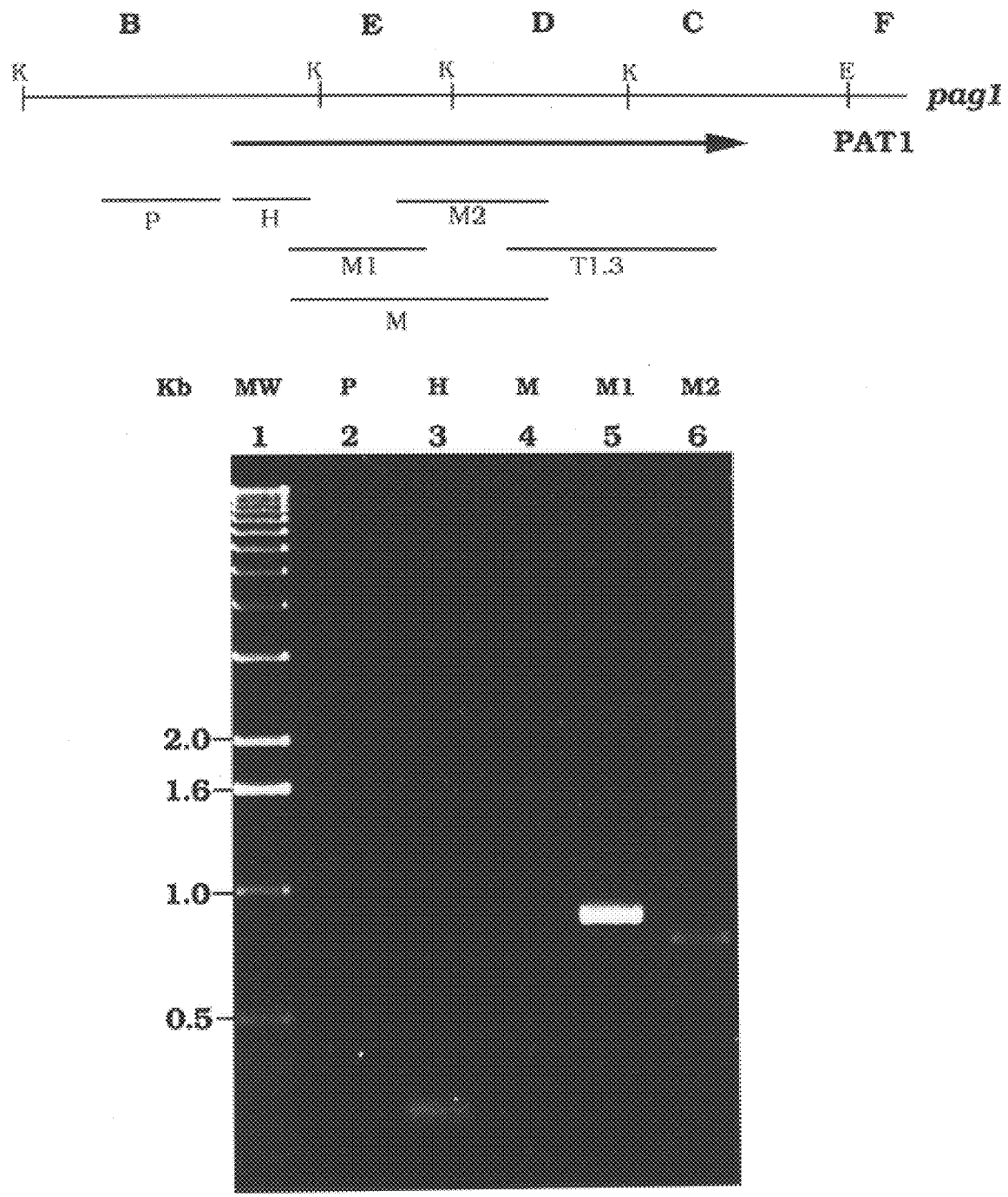
FIG. 14 shows: Amplification of sub-CDNA fragments using RT-PCR. Overlapping fragments covering the 2.8-kb CDNA region were amplified using paired primers. Regions of the amplified fragments, H, M1, M2, M, and T1.3 are indicated on top of the panel and the results are shown on an agarose gel. The P fragment which resides in the promoter region was subjected to amplification to serve as a negative control. The T1.3 fragment was the 1.3-kb fragment derived from random primer-primed PCR as shown in FIG. 13(C).

The CDNA sequence of PAT1. Results from the elution of total RNA through an oligo Dt column revealed that PAT1 either contains no poly (A) tail or only a very short poly (A) tail which can not bind strongly to the oligo Dt beads (FIG. 12B). These results indicated that the conventional CDNA cloning strategy which is synthesized by oligo Dt primer may not have worked properly with this unique transcript. Therefore, CDNA of PAT1 was amplified and cloned into several fragments using the RT PCR technique. Multiple primers were used to amplify H, M1, M2, and M CDNA fragments which run across the entire PAT1 coding region except the random primer-primed 3' end T1.3 region (FIG. 14). The entire sequence of PAT1 CDNA was determined and found to be identical to the sequence of genomic DNA, indicating that RNA editing or splicing does not occur after transcription.

Figure 15A:
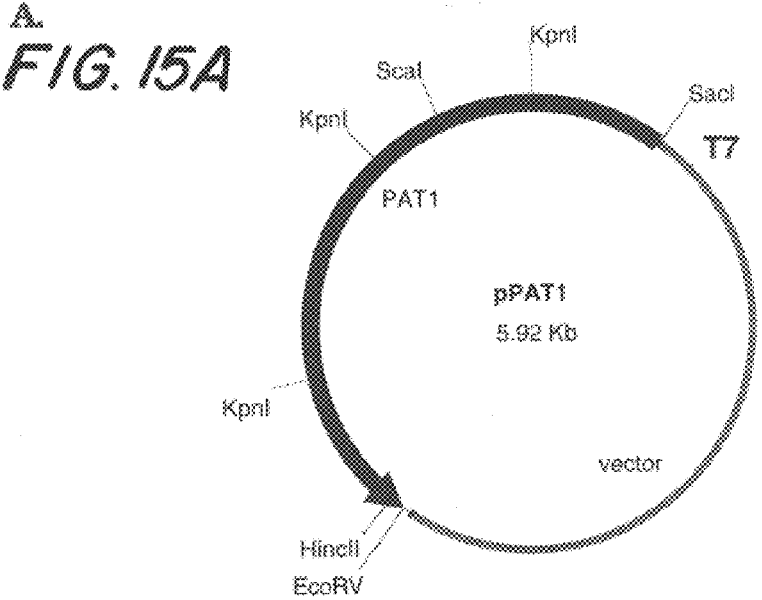
FIG. 15(A) shows: The plasmid pPAT1 which contains an intact PAT1 coding region.
Figure 15B:
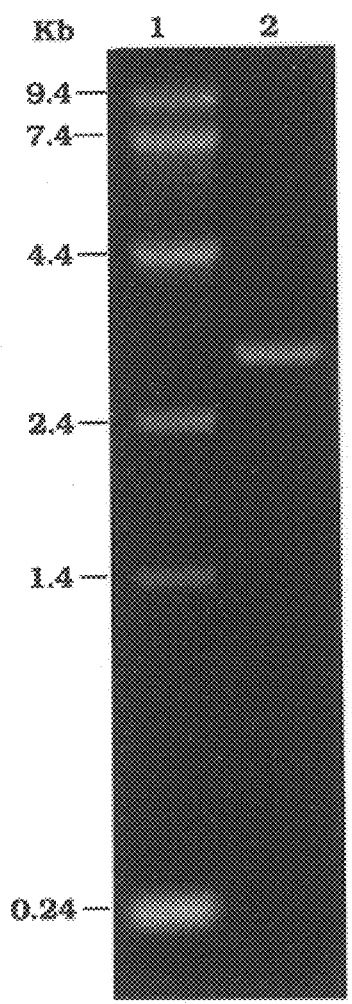
FIG. 15(B) shows: This plasmid was linearized using a unique site EcoRV and in vitro transcribed using bacteria phage T7 polymerase. A single 2.9-Kb RNA fragment was generated as shown in lane 2.
Figure 15C:
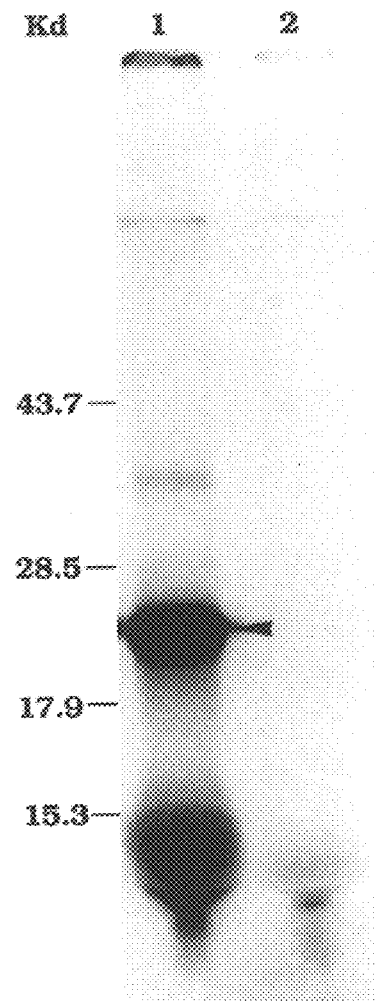
FIG. 15(C) shows: In vitro transcribed PAT1 and an uncapped CAT RNA (provided by the in vitro translation kit, Gibco/BRL, Inc., MD, USA) were in vitro translated and labeled following the instructions of the manufacturer. Lane 1 shows that, although the CAT protein was properly translated (arrow head), no peptide was translated from PAT1 as shown in lane 2.

PAT1 is not translated in vitro. The full-length CDNA of PAT1 was sub-cloned into Pbluescript (FIG. 15A). PAT1 RNA was in vitro transcribed as a single 2.9-kb RNA species (FIG. 15B). When the same amounts of PAT1 and CAT RNAs were in vitro translated, CAT protein was found to be synthesized with high abundance, whereas the PAT1 protein was not detectable (FIG. 15C). This is further evidence which suggests that PAT1 is a non-protein coding RNA.

Example V

High DNA copies were found in the cells persistently infected with Hz-1 virus

Persistent/latent viral infection is a long-term association between the host cell and the virus. It was recognized to occur in insects since the last century in that the polyhedral virus disease of the nun moth *Lymantria monacha* tended to spread slowly in an insect population and did not affect all individuals. Depending upon external conditions, this chronic course would often change suddenly into an active or acute form. Today however, one century has elapsed, and, although viral persistency has been speculated with many different viruses, little is known about the associations between these viruses and their hosts in this long period of conceal virus life cycle (Podgwaite and Mazzone, 1986; Burand et al., 1986; Hughes et al., 1993). Hz-1 virus (previously named as Hz-1 virus) was used to elucidate the association and physical status of a persistent viral infection of insect host cells. Hz-1 virus was recognized as the type species of the subfamily Nudibaculoviridae of family Baculoviridae (Willson, 1991). Recently it and other non-occluded Baculoviruses have been removed from the Baculovirus family and are currently unclassified (Volkman, 1994).

The long-term association between Hz-1 virus and host cells is generally described as a persistent viral infection and is among the best studied viral persistent infection system in insects. Hz-1 virus was identified by Granados and co-workers in 1978 (Granados et al., 1978) as a persistent infecting Baculovirus agent in the IMC-Hz-1 ovarian cell line. It is an enveloped, non-occluded, rod-shaped virus, which contains a double stranded circular 230 kb DNA genome (Chao et al., 1990; Huang et al., 1982). The virus particles are usually heterogeneous in length as viewed by the electron microscope. Later, it was shown that the virus could be isolated to fair homogeneity by plaque purification (Burand et al., 1983; Chao et al., 1990).

Electron microscopic examination of the purified homogenous virus particles (referred as standard virus) indicated that the mean particle length is 414 nm. However, after several serial, high-multiplicity passages of standard virus, the amount of defective-interfering particles increased significantly. The length of the defective-interfering particles were generally shorter than that of the standard particles. This is due to the deletions of the standard viral genome (Burand et al., 1983; Chao et al., 1990). Later, it was found that the persistently infected cell lines could be established from the few cells remaining after acute infections (Burand et al., 1986; Chal et al., 1990). Subcultures of the established persistently infected cell lines may release infectious virus into the medium (McIntosh and Ignoffo 1981; Ralston et al., 1981; Burand et al., 1986). Nevertheless, since in general the cells persistently infected with Hz-1 virus looks normal and grow well, it was not known if the virus particles were released from a small number of the spontaneous reactivated cells or were released from all the cells simultaneously with relatively low yield per cell. Also, it was not known if the cells release viruses through long term passages or if the viruses were only produced from the persistently infected cells for a certain period of passages after their establishment.

The host range of Hz-1 virus is broad. Insect cell lines from five lepidopterans, including *Trichoplusia ni* (TN368), *Spodoptera frugeperda* (IPLB-SF-212), *Heliothis zea* (IPLB-1075), *Mamestra brassicae, Porthetria dispar* (IPLB-65Z), *Lymantria dispar* (LD252Y) and *H. virescens* (BCIRL-HB-AM1) were reported to be susceptible to its infection (Wood and Burand 1986). Persistent Hz-1 virus infections have been reported to be established in three of these insect lines: *H. zea, T. ni* and *S. frugiperda* (Chao et al., 1990; Chao et al., 1990; Chao et al., 1992; Wood and Burand 1986; Granados et al., 1978). Once the host cells are persistently infected with Hz-1 virus, the host cell are resistant to superinfection with the same virus (Burand et al., 1986; Lee et al., 1993).

Hz-1 virus has long been recognized as an excellent model system for the study of viral persistent infection (Burand et al., 1983; Burand et al., 1986; Chao et al., 1990; Chao et al., 1992). Its host range is broad and both viral productive and persistent infections can be generated in cell lines. During viral productive infections, there are more than 100 RNA transcripts detectable, whereas only a single major viral RNA transcript, the persistence-associated transcript 1 (PAT1), was detected during persistent viral infections (Chao et al., 1992). Thus, this serves as a good model system for the study of the mechanism of differential viral gene expression during productive and persistent viral infections. The physical status and the associations of the virus with the persistently infected insect cells are still largely unknown. The ability for pag1 to drive expression of exogenous DNA, such as DNA encoding a marker, facilitates use of Hz-1 as a model for study, thereby providing another utility for the invention.

MATERIALS AND METHODS

Cells and viruses. The *T. ni* (TN368) and *S. frugiperda* (SF21AE and SF9) cell lines were maintained at 26° C. in a modified TN-MFH medium as described by Burand et al., (Burand et al., 1983) and Chao et al., (Chao et al., 1990). Standard Hz-1 virus was derived by plaque purification. Persistently infected cell lines TNP1, TNP2, TNP3, SFP2, and SFP4 were derived from serial high-multiplicity (moi= 10) passages of the standard virus following the procedures of Burand and Wood (Burand and Wood 1986). The TNP1, TNP2, and TNP3 cell lines were derived from TN368 cell; and the SFP2 and SFP4 cell lines were derived from SF21AE and SF9 cells, respectively. Standard Hz-1 virus was derived by plaque purification. E2 strain of *Ac*MNPV (O'Reilly et al., 1992) was used in this experiment. $TCID_{50}$ assay was performed as described (Summers and Smith 1988).

"Infectious center" assays. The "infectious center" assay was based on the idea that if any infectious viruses are released from a persistently infected cell, and if this cell is surrounded by a "lawn" of healthy cells, the released viruses will infect and lyse the surrounding healthy lawn cells forming a plaque. Presumably, if any of the persistently infected cell which can produce and release virus propagates, a colony of virus-releasing cells will be generated and grow at the center of the plaque like area.

"Infectious center" assays were performed by taking advantage of Hz-1 virus being able to infect multiple host cells including TN368 and SF21AE cells. TN368 cell is a fibroblast-shaped cell and SF21AE is a rounded cell. Once a TN368 cell is persistently infected by the Hz-1 virus, the morphology does not change significantly except that, probably due to syncytial formation, the size of some of the cells are greatly increased. Therefore, the persistently infected TN368 cells can be distinguished from the surrounding healthy SF21AE "lawn" cells or vise versa. Healthy cells ($1\times10^5$) of one species were "infected" with 10× diluted persistently infected cells derived from the other species from $1\times10^5$ to $1\times10^2$ cells per well of 24 well plates. By calculating the number of the seeded persistently infected cells and the number of plaques formed in the healthy "lawn" cells, the rates of spontaneous reactivation could be estimated.

Southern and Northern hybridizations. Total cellular and viral DNAs were purified as described previously (Chao et al., 1990; Chao et al., 1992). Purified DNAs were digested with restriction enzyme EcoRI and fractionated through a 0.8% agarose gel for 24 h at 3 V/cm. After ethidium bromide staining and UV photography, the DNA pattern was transferred to a Gene Screen (Stratagene Co., USA) filter, hybridized with the $^{32}$P-labelled standard viral DNA, and autoradiographed. Northern hybridizations were performed as described (Chao et al., 1992). Briefly, samples containing 3 ug of total RNAs extracted from the healthy and persistently infected cells were treated with glyoxal and fractionated through 1% agarose gel. After blotting, the filter was hybridized with random primer labeled probe prepared from viral EcoRI-M fragment (Chao et al., 1992).

Slot hybridizations. Total genomic DNAs were purified from healthy and persistently infected cell lines and transferred to the Gene Screen filter using "MILLIBLOT" following manufacturer's instructions (Millipore, Inc., USA). The filter was hybridized with the $^{32}$P-labelled standard viral DNA, followed by autoradiography.

Pulsed-field gel electrophoresis (PFGE) Analyses.

Healthy or persistently infected TN368 cell lines ($2\times10^7$) were mixed with equal volumes of 1% low melting agarose prepared in PBS and cooled to 45° C. These samples were then transferred to plug molds with a pipette and allowed to harden at 4° C. Sample blocks were transferred to eppendorff tubes which contain 3–5 volumes of 0.5M EDTA at Ph 9, 1% Sarcosyl, and 0.5 ug/ml proteinase K. These blocks were digested for 1–2 days at 50° C. with constant, gentle shaking. PFGE was carried out using a "CHEF-DRII" pulsed-field electrophoresis system (Bio-Rad Laboratories, USA) in a 1.0% agarose gel with 0.5×TBE buffer (40 Mm-Tris-borate, 1 Mm-EDTA) at 5.25 V/cm with pulse time 40 s for 24 h at 14° C. The gel was stained in $H_2O$ containing 0.5 ug/ml ethidium bromide and photographed under short wavelength UV illumination. The gels were transferred to a Gene Screen filter, hybridized with the $^{32}$P-labelled standard viral DNA, and autoradiographed.

Electron microscopy. TN368 and TNP3 cells ($1\times10^6$) were harvested and washed in 0.1M sodium cacodylate buffer (Ph 7.2). The cell pellets were fixed for 1 hr with a mixture of 4% paraformaldehyde and 0.2% glutaraldehyde in 0.1M sodium cacodylate buffer at 4° C., and then post fixed for 1 hr with buffered 1% osmium tetroxide at 4° C. After dehydration in a sequential ethanol series, the cells were infiltrated and embedded in LR white. Ultrathin sections were stained for 30 min in uranyl acetate and for 5 min in lead citrate. Grids were examined by EM902 (Zeiss, Inc. Germany) electron microscope. Productively infected SF9 cells were also harvested at 17 hr post viral infection (moi=5) and treated with the same procedure as mentioned above to show the size and morphology of viral particles under the same electron microscopic conditions.

RESULTS

Figure 16A:
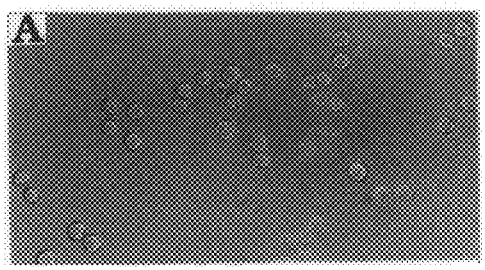
FIG. 16(A) shows: healthy SF21AE cell.
Figure 16B:
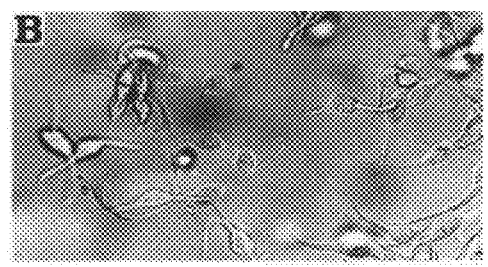
FIG. 16(B) shows: TNP3 cell.
Figure 16C:
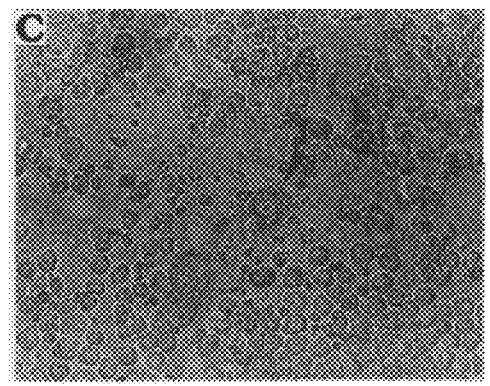
FIGS. 16(C) to (F) show: plaques formed in SF21AE cells by the infectious viruses which were released from TNP3 cells upon viral reactivation.
Figure 16D:
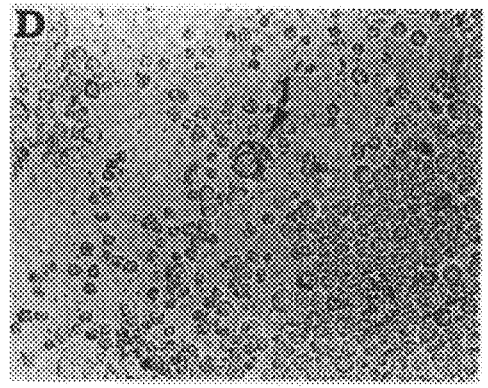
Figure 16E:
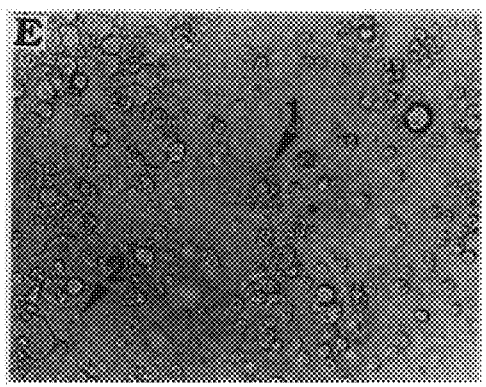
Figure 16F:
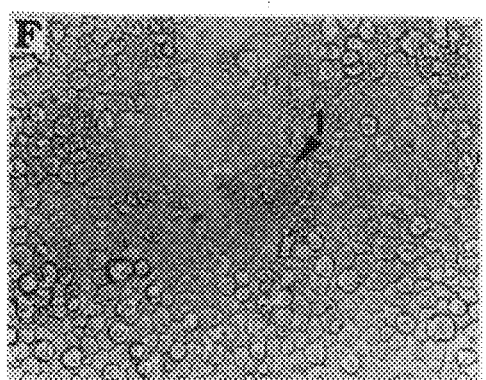
Figure 16G:
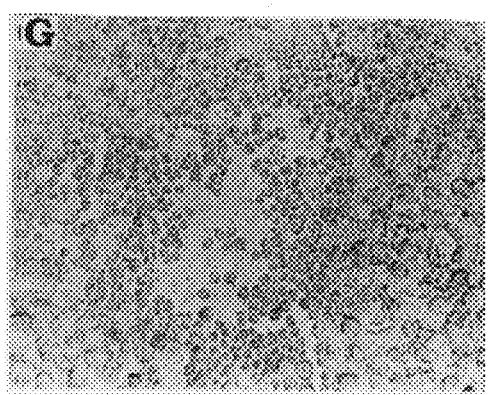
FIG. 16(G) shows: Example of few plaques formed by the residuary viruses which have been released from previous reactivated TNP3 and have not been successfully washed away before the infectious center assay was performed.
Figure 16H:
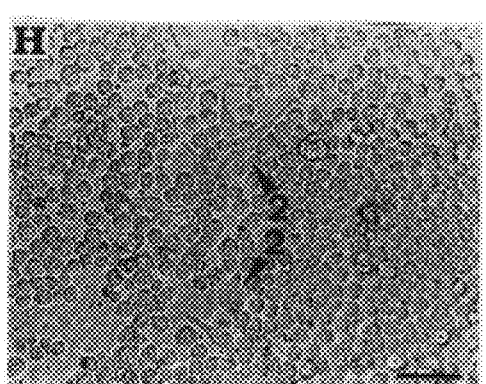
FIG. 16(H) shows: Examples of a region where infectious center was not observed. Arrowheads indicate: 1. Dead TNP3 cells after viral reactivation. 2. Living TNP3 cells without reactivation. Bar=50 um.

Mature, low rate of infectious viruses were only produced from the spontaneous reactivated cells. Five persistently infected cells—TNP1, TNP2, TNP3, SFP2 and SFP4 were analyzed. When they were newly established, infectious viruses could be detected in media; however no infectious virus were detectable in any of the persistently infected cell lines after long passages (Table 2). Although newly established persistently infected cells produced viruses, when these lines were seeded onto healthy cells as described previously, the "plaque" produced from all the lines were very few. Ranging from 21 plaques/$10^5$ cells for TNP3 and SFP2 cells to the highest 210 plaques/$10^5$ cells for the TNP1 cells (Table 2). These results clearly showed that within 5 days, the time needed for plaque formation, less than 0.2% of the tested persistently infected cells produced virus. Since these "plaques" were generated by all the persistently infected cell lines when they were newly established, the production of mature, infectious viruses from the reactivated cells were evidenced. The interesting finding came from the examination of the center of the plaque. Instead of detecting foci of persistently infected cells at the center of plaques, a dead cell originated from the input persistently infected cells were always observed. Results of such experiments was shown by seeding of TNP3 cells onto healthy SF21AE cells (FIG. 16). These reactivated cells were usually located at the center of the plaques and appeared to be lysed (FIG. 16, arrowheads 1). The remains of some of the reactivated TNP3 cells were large. Persistently infected cells which did not release virus (not reactivated) grew harmoniously with the "lawn" SF21AE cells (FIG. 16H, arrowheads 2).

High DNA content and co-existence of standard and deleted viral genomes in the persistently infected cells. The viral DNA content of several persistently infected cell lines were studied by slot hybridization technique. The genomic DNAs were purified from five persistently infected cell lines, TNP1, TNP2, TNP3, SFP2 and SFP4. Increasing amounts of total cellular DNAs and the standard viral genomic DNAs were slot blotted onto a nylon filter. The results showed that the contents of viral DNAs in TNP1, TNP2, TNP3, SFP2 and SFP4 were 12%, 0.8%, 16.4%, 0.1%, and 0.4%, respectively (FIG. 17 and Table 2).

Figure 18:
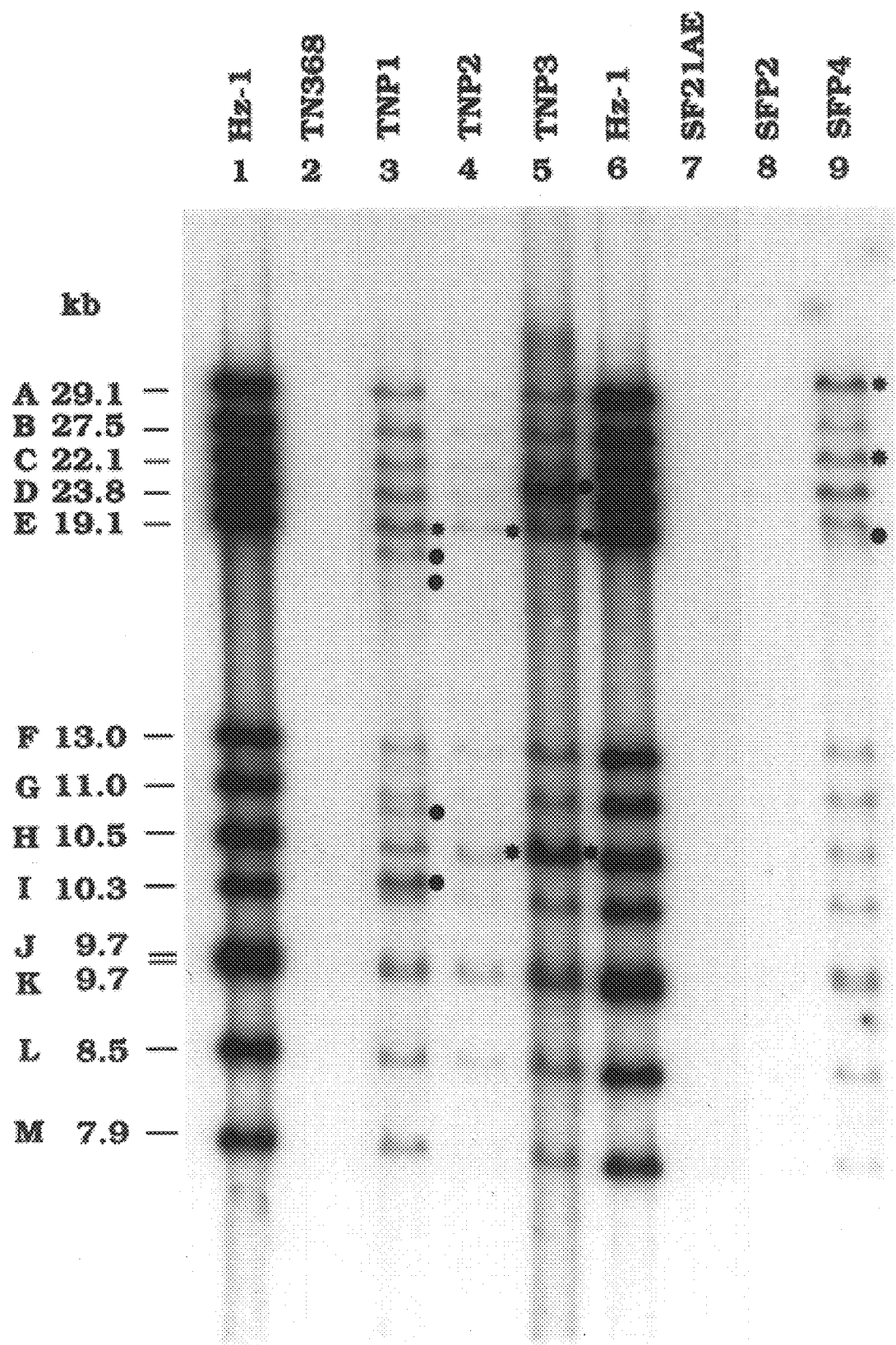
FIG. 18 shows: Southern hybridization of viral and cellular genomic DNAS. Total genomic DNAs of the parental and persistently infected cells were digested with restriction enzyme EcoRI. After fractionation through an agarose gel, the digested DNA was blotted onto a filter and then hybridized with viral genomic DNA probe. Dot () indicates extra fragments and asterisk (*) indicates multimolar bands which were detected from the viral genome of the persistently infected cells.

The viral DNA contained in these five cell lines were further analyzed. The total genomic DNAs purified from these five persistently infected cell lines were digested with EcoRI and fractionated through an agarose gel. After Southern blotting, they were hybridized with the genomic DNA probe of standard virus. The hybridized patterns showed that viral DNAs in these persistently infected cell lines contain all fragments found in the standard viral genome. However, all the lines contained additional and multimolar fragments (FIG. 18, fragments marked with dots and asterisks, respectively) indicating that viral genome deletions and possibly duplications occurred (Burand et al., 1986; Chao et al., 1990).

Figure 19:
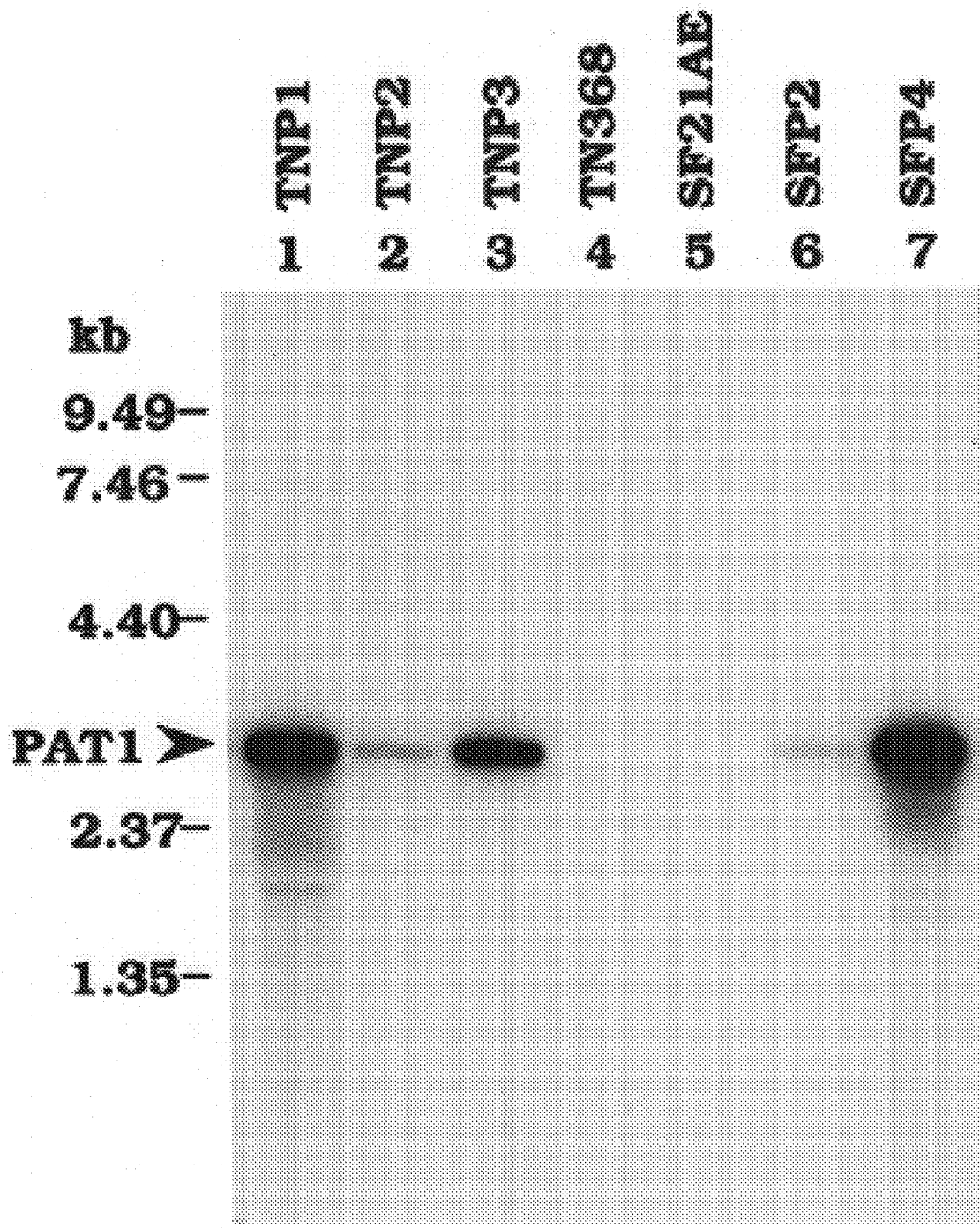
FIG. 19 shows: Detection of PAT1 expression by Northern hybridization. Total RNA was extracted from the healthy (TN368, and SF21AE) and the persistently infected (TNP1, TNP2, TNP3, SFP2, and SFP4) cells. The expression of PAT1 was detected by Northern hybridization using viral EcoRI-M fragment, by which PAT1 is encoded (Chao et al., 1992), as probe.

Since all of the persistently infected cell lines contained viral DNA, it was of interest to determine if PAT1, previously found as the only detectable persistence-associated transcript, was expressed in all the persistently infected cells. Total RNAs were extracted from the persistently infected cells and fractionated through agarose gel. After Northern hybridization, PAT1 was found in all of the persistently infected cells. The intensity of PAT1 signal was different in individual cell lines. Among them, PAT1 was expressed stronger in TNP1 and TNP3, than in TNP2; and in SFP4 than in SFP2 (FIG. 19). Although the expression of PAT1 was in general stronger in the cells which harbor more copies of viral genomes, the efficiency. of PAT1 expression was much higher in the newly established SFP4 cells than those long-passaged persistently infected cells.

Figure 20A:
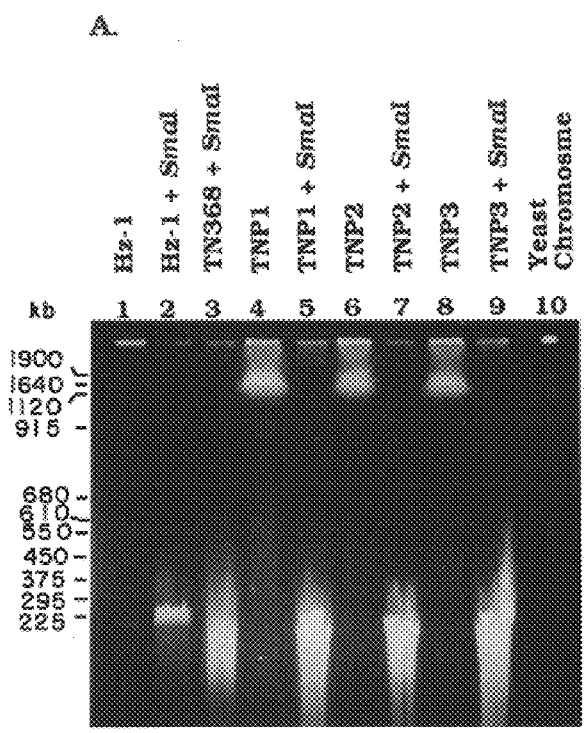
FIG. 20(A) shows: They were fractionated through PFGE with or without prior SmaI digestion.
Figure 20B:
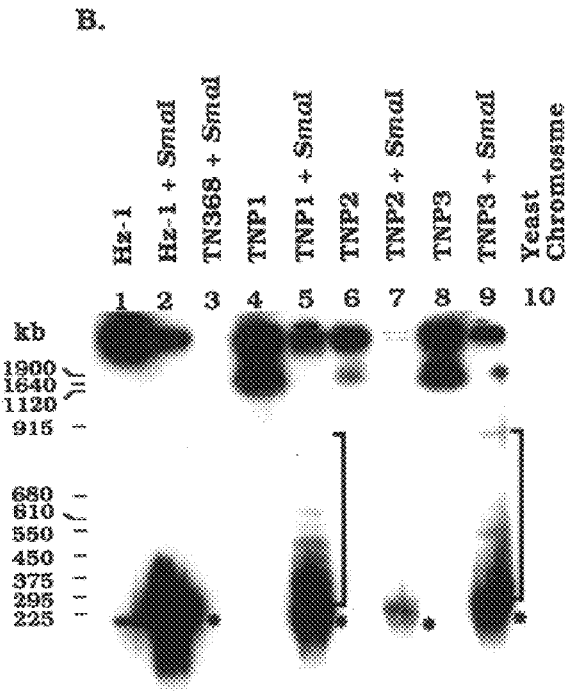
FIG. 20(B) shows: The gel was then blotted onto a filter and hybridized with viral genomic DNA probe. An asterisk (*) marks the bands or regions where linearlized viral genomic DNA resides. After SmaI digestion, viral DNAs which are larger than unit size and therefore likely to be inserted in the host genomes are marked with brackets.
Figure 22A:
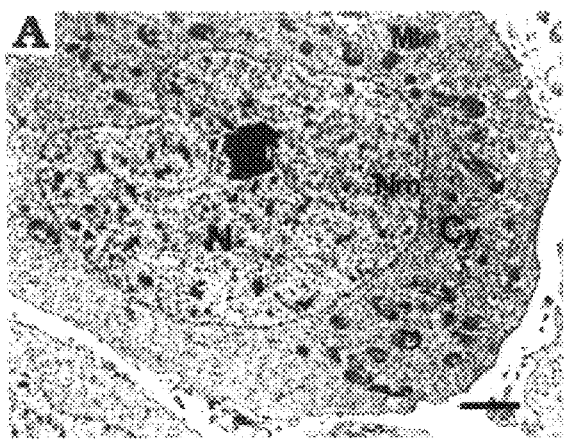
FIG. 22(A) shows: TN368 without viral infection.
Figure 22B:
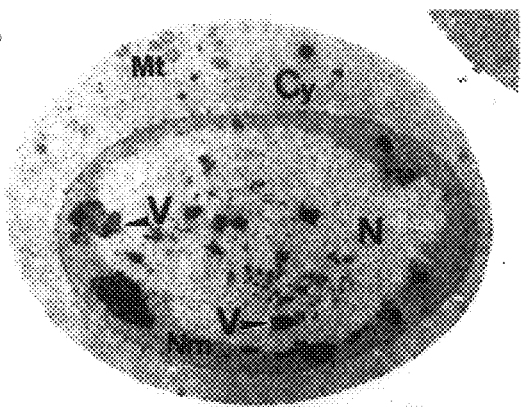
FIG. 22(B) shows: SF9 cell productively infected with Hz-1 virus to show the morphology of newly synthesized viruses in the cell. Virus particles (V) are indicated with arrowheads.
Figure 22C:
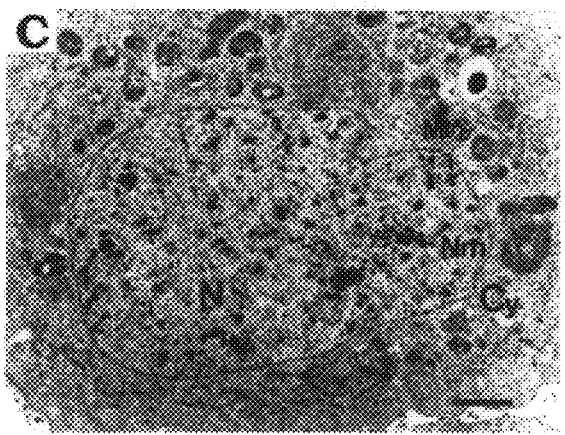
FIG. 22(C) and (D) show: Electron micrographs which show that virus particles are not detectable in TNP3 cells. Abbreviations: Nm, nuclear membrane; N, nucleus; Cy, cytoplasm; Mt, mitochondria. Bar=2.5 um.
Figure 22D:
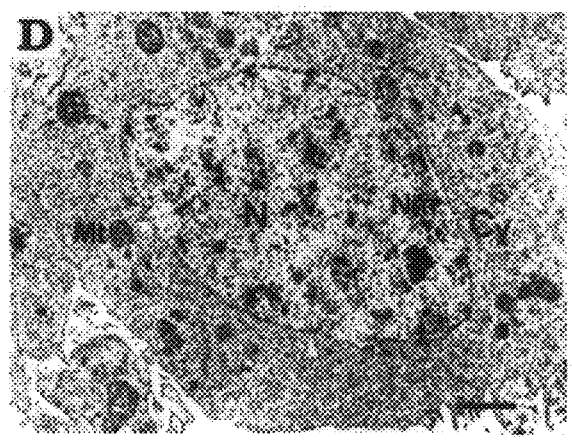
FIG. 22 contains (A), (B), (C) and (D) and shows: Electron microscopic study of the cells productively and persistently infected with Hz-1 virus.

PFGE analysis of the viral genomes in the persistently infected cell lines. PFGE was used to analyze the physical nature of the viral genome in the cells. Viral particles and different persistently infected cell lines were prepared in low-gelling-temperature agarose. They were either digested with or without SmaI and loaded onto the gel. Without SmaI digestion, the majority of viral DNAs stayed in the well (FIGS. 20A and 21A, lanes 1). With SmaI digestion, a single species DNA of about 230 kb migrate into the gels (FIGS. 20A and 21A, lanes 2). These DNAs were blotted onto filters and hybridized with viral genomic DNA probe. FIGS. 20B and 21B showed that without SmaI digestion, viral DNA isolated from the particle was primarily detected in the wells. However, relatively small portions of the viral DNA were detected as 230 kb molecules (FIGS. 20B and 21B, lanes 1). These viral DNAs may have resulted from nicking during sample preparation. After SmaI digestion, the majority of the viral DNA from the particles was converted to 230 kb linear molecules (FIGS. 20B and 21B, lanes 2, asterisks). A portion of the viral DNAs remained at the origin, presumably representing viral genome in virion particles which was not completely digested by proteinase K during sample preparation.

Genomic DNAs of different cell lines were also analyzed (FIG. 20, lanes 3–9; and FIG. 21, lanes 3–8). TN368, the parental cell of TNP1, 2, and 3 was digested with SmaI and subjected to PFGE analysis. The size ranges of the digested genomic DNAs were approximately 30–600 kb as revealed by ethidium bromide staining (FIG. 20A, lane 3). SF21AE, the parental cell for SFP2 and 4 was not digested before they were subjected to PFGE. The undigested genomic DNA clearly migrated into the gel and stayed in one to several thousand kb region (FIG. 21A, lane 3). These genomic DNAs, with or without SmaI digestion, were not hybridized by viral genomic probe (FIGS. 20B and 21B, lanes 3) thus served as negative controls.

Persistently infected TNP1, TNP2, and TNP3, and SFP2, and SFP4 cells were subjected to PFGE analyses. When they were not digested with any restriction enzyme, two signals in each cell lines were detected by the hybridization of viral genomic DNA probe. One were on the wells and the other one were in the 1–3 megabases region (FIGS. 20B, lanes 4, 6, and 8; and 6B, lanes 5 and 7. Cellular chromosomal DNAs which could migrate into the gels were indicated by arrowheads). When these genomic DNAs were digested with SmaI, the viral signals on the wells were largely decreased and the signals in the 1–3 megabases regions disappeared completely. Major new signals in 230 kb region appeared on SmaI digested lanes (FIGS. 20B, lanes 5, 7, and 9; and 6B, lanes 6 and 8, asterisks). Above these bands, multiple fragments with sizes ranging from 300–800 kb were observed (FIGS. 20B, lanes 5, 7, and 9; and 6B, lanes 6 and 8, brackets).

Since open circular viral genomic DNAs stayed at the origin and could migrate to the 230 kb region once they were linearlized by SmaI digestion (FIGS. 20B and 6B, lanes 1 and 2), those viral signals detected at the origin from the samples of the persistently infected cells must be mainly circular viral genomic DNAS. These viral DNA then migrated to 230 kb region and formed a major band when digested with SmaI. Multiple bands detected above these major 230 kb bands were resulted from the digestion of viral DNA inserts in the host chromosome (FIGS. 20B, lanes 5, 7, and 9; and 6B, lanes 6 and 8).

Virus particle was not detected in the cells persistently infected with Hz-1 virus. Since all the cells persistently infected with Hz-1 virus contain multiple copies of viral genome. TNP3, the cell with highest viral content was examined with electron microscopy. Although this line contains about 2500 copies of viral genome per cell, viral particle was not found for more than 50 cells inspected (FIG. 22).

Viral interference in the cells persistently infected with Hz-1 virus. When a host cell is persistently infected with a virus, it often becomes resistant to the challenge of the same and/or different viruses, a phenomenon known as homologous (resistant to the same virus) or heterologous (resistant to different viruses) interference (Abernathy et al., 1990; Adans and Brown 1985; Condreay and Brown 1986; Ahmed and Stevens 1991; Knutson and Sugden 1989; Riedel and Brown 1979). The cells persistently infected with Hz-1 virus were challenged with Hz-1 virus and AcMNPV, the latter is the best studied Baculovirus (Wison 1991). The results showed that all the cells that are persistently infected with Hz-1 virus resistant to the superinfection of the same virus. The differences in the viral progeny producing capabilities between the parental (TN368 and SF21AE) and the persistently infected cells were about 3 to 4 logs (FIG. 23A). However, all these cells persistently infected with Hz-1 virus were not significantly resistant to the challenge of AcMNPV as compared by the viral progeny producing capabilities in both parental and persistently infected cells (FIG. 23B).

DISCUSSION

Persistent viral infections are an interesting and important medical and agricultural issues. However, once the host cell is persistently infected with a virus, the viral genome can persist for indefinite cellular passages or the life span of the host organism. In addition, due to the fact that the virus is not readily detectable during this long period of life cycle, difficulties in experimentation are always encountered. For herpes simplex viruses, one of the best studied latent DNA viruses, the latency can only be established in neural tissues but rarely in the cultured cell lines. During this period of the virus life cycle, only 0.11–0.03 viral genome equivalent/cell in the latently infected tissue were detected. This renders the study of herpes simplex virus difficult, because the latent infection is limited and only detectable by the most sensitive technique (Fraser et al., 1986; Fraser et al., 1984; Leist et al., 1989). Epstein-Barr virus, another well-studied herpesvirus, lacks a host cell capable of supporting an efficient lytic replication cycle and infects only B cells or epithelial cells (Knutson and Sugden 1989). Hz-1 virus is quite different. Both viral productive and persistent infections can be established in cell lines. It takes only one to two weeks for persistent viral infection to be established and the host range of this virus is broad (Chao et al., 1990; Burand et al., 1986). Thus, it provides us a good opportunity for the study of persistent viral infections. Specifically, it provides us an easy and manipulatable model for the study of viral persistent infection in insects.

This invention demonstrates that newly established cell lines which are persistently infected with Hz-1 virus produce virus whereas the production of virus ceases after long passages. Certainly, applicant does not rule out the possibility that viral reactivation will still occur after long passages due to physiological or environmental stimulation. In the newly established cells which were persistently infected with Hz-1 virus, the virus was found to be produced by spontaneous reactivation of the minor cell populations. This is a phenomenon very similar to that of herpesviruses during viral latency. Viral reactivation is best studied in herpes viruses by monitoring the appearance of the viral antigens associated with productive viral infection (Metzenberg 1990; Bloom et al., 1994; Heston et al., 1982; Openshaw et al., 1979). After the detection of these antigens, the cells were either fixed or damaged. As a result, whether the mature viruses were finally produced from the particular reactivated cells and whether the specific individual cells die or survive and become virus producers after reactivation were only elucidated in a population but not possible to the fate of individual cells (Weigel and Miller 1983; Baichwal and Sugden 1988). By taking advantage of the fact that the Hz-1 virus being able to infect different host cell lines, applicant designed a simple and reproducible "plaque" assay technique to verify the nature of viral reactivation and to examine the final fate of the reactivated cells. It was found that during early persistent viral infection of Hz-1 virus, very small proportions of the host cells were reactivated, which is comparable to that of the herpesviruses (Weigel and Miller 1983). Furthermore, this method provides an excellent opportunity for elucidation of the production of viral progeny and final death of individual host cells upon viral reactivation.

The results of the dot blot hybridization experiments revealed that a host cell may harbor as much as 16% of the total DNA as the viral genome. These were quite unexpected results. This is obviously a very extreme case where a parasitic DNA can so abundantly infest a host cell during persistency, while the host cell is still growing well. Further analysis of the viral DNAs of the persistently infected host cells revealed that two different types of viral DNA, standard and deleted genomes, were found. This result further reflects the fact that the defective-interfering particle may play a role in the establishment and maintenance of persistent infections (Wood and Burand 1986; Burand et al., 1986).

The physical status of the viral DNAs in the persistently infected host cells is an important issue for the association of host and virus. Viral DNA can possibly exist in the persistently infected host cells as circular, linear, and/or inserted forms in the host genome. Conventionally, in order to determine whether a foreign DNA is inserted in the host genome or not, it is necessary to restrict digest the genome and use probe hybridization techniques to find the junction fragments. If a DNA is inserted into the host chromosome, the junction fragments resulted by suitable restriction digests will vary from the original sizes. Such change is the evidence of DNA insertion into the host genome. Unfortunately, this approach is not possible for the study of Hz-1 viral DNA insertion in the host cells. According to the data from this study (FIG. 18) and others (Burand et al., 1986; Chao et al., 1990; Huang et al., 1982), viral genome with deletions were always detected in these cells. When part of the viral genome is deleted, the sizes of restricted fragments and/or junction fragments of inserted viral genomes are changed, making the determination of possible existence of insertional junction fragments difficult. Also, the size of the viral genome is large. After restriction digestion, too many fragments are generated which complicates the identification of possible insertional junction fragments. Thus different approaches were used to resolve these problems.

Several techniques have been used to study the physical status of viral genomes in the latently infected cells. Anderson-Anveret and Lindahl Anderson-Anvret and Lindahl 1978) and Lindahl et al. (Lindahl et al., 1976), took advantage of the fact that the density of the viral DNA is slightly different from the genome of the host cell. The physical status of the viral DNA of herpes virus was examined by CsCl gradient centrifugation analysis. However, since the differences in the densities of these DNAs are small, those experiments rely on the careful analyses of the fractions from partially over-lapping viral and host genomic DNA peaks. Besides, it was not known if viral DNA exists as circular or linear form. A more recent approach is the use of chromosomal in situ hybridization technique to look into the locations of viral integration (Henderson et al., 1983; Teo and Griffin 1987; Hurley et al., 1991). This approach can locate the exact site of integration, however, less information is known about the unintergrated viral DNA. When this method was applied, Applicant found it was very delicate to pin-point the best timing of chromosome condensation. Besides, considering that extremely large numbers of viral episomes and inserted viral genomes are contained in almost all the cell lines (Table 2), it is almost impossible to distinguish the signals of viral episomes from inserted viral DNAs.

Although the first DNA CsCl gradient centrifugation analysis was performed more than a decade ago, it is still currently used to determine whether or not a large viral DNA is integrated in the host genome (Mellerick and Fraser 1987; Rowe et al., 1990). Another method which is also frequently used is the Gardella gel technique originally described by Gardella et al. (Gardella et al., 1984). This technique is powerful in analyzing circular and linear viral genomic DNAs. However, it cannot analyze viral DNAs which are inserted in the host chromosome nor further restriction digestion of genomic DNAs to analyze episomal or inserted forms of viral genomes.

In this example, a different approach is employed. The PFGE technique, was used to resolve this problem. The conventional agarose gel electrophoresis can only analyze DNAs with sizes lower than 30 Kb. Van Der Berg et al. (Van Den Berg et al., 1988) used field inversion technique to isolate viral genome from the cells productively infected with human cytomegalovirus. Similarly, PFGE was used by Harris and Bentley (Harris and Bentley 1988) and Silins et al. (Silins et al., 1992) to isolate 172 kb episomal DNA of Epstein-Barr virus. In this example, PFGE was, for the first time, adapted to resolve linear, circular and inserted forms of viral DNAs simultaneously. In principle, inserted viral DNA co-migrates with host chromosomal DNA and stays in the megabase region. However, for non-inserted large viral DNAs, if it is circular, the DNA will be trapped at the top of the gel; and, if it is linear, the DNA will be amenable to PFGE separation (Smith et al., 1987; Levene and Zimm 1987).

By using this approach, Applicant found that approximately half of the persistent viral DNAs are inserted in the host chromosomes, and the other half of viral DNAs exist as circular molecule. These experiments revealed that PFGE could be a very useful technique to analyze the physical status of the viral genomes in the persistently infected host cells. Since it was found that although viral DNA content can be as high as 16% of the total cellular DNA (Table 2), no virus particle was found by careful electron microscopic examination (FIG. 22) suggesting that at least most of these circular viral DNAs exist as episome rather than package in virions. These experiments also indicated that the 172 kb bands detected by both Harris and Bentley (Harris and Bentley 1988) and Silins et al. (Silins et al.,.1992) by PFGE techniques are likely linear rather than circular episomal Epstein-Barr viral genomes. These linear viral DNA may come from the reactivated virion or the nicking of episomal DNA during sample preparation.

Long term association of Hz-1 virus and the host cells has been referred as persistent infection since the discovery of this virus (Burand et al., 1986; Granados et al., 1978). In this application Applicant uncovered many new insights concerning the nature of persistent Hz-1 virus infection and found that persistent infection may not be the best term for describing such long term virus-host association.

Persistent infections can be classified into three categories, they are latent, chronic, and slow infections. Latent infection was defined as the condition under which the virus is usually not detectable and intermittent acute symptoms may occur (Wood and Burand 1986). Garcia-Blanco and Cullen (Garcia-Blanco and Cullen 1991) similarly proposed that latency is the reversible nonproductive infection of cells by a replication-competent virus. The latent infection of herpesviruses has also been defined as a type of persistent infection in which the viral genome is present but infectious virus is not produced except during intermittent episodes of reactivation (Stevens 1989; Baichwal and Sugden 1988). Similar to herpesviruses, differential viral gene expressions were observed in Hz-1 virus during viral productive and persistent infections (Chao et al., 1992). In addition, infectious Hz-1 virus is not released during persistency unless a lytic reactivation takes place (FIG. 16 and Table 2). These and many other features demonstrated herein suggest that persistent infection of insect cells by Hz-1 virus may be better described as latent viral infection.

Viral latent infection in insects is supposed to be a very common phenomenon occurring in the field and even in the long-term laboratory stocks (Burand et al., 1986; Chao et al., 1985; Chao et al., 1986; Hughes et al., 1993; Lee et al., 1993; Longworth and Cunningham 1968; Podgwaite and Mazzone 1986). Usually virus can be easily detected during productive infection. However, in between viral out-breaks, viruses may be harbored in insects as latent infections and difficult to find (Evans 1986; Briese 1986).

Having thus described in detail preferred embodiments of the present invention, it is to be understood that the invention defined by the appended claims is not to be limited by particular details set forth in the above description as many apparent variations thereof are possible without departing from the spirit or scope thereof.

Furthermore, the Hz-1 virus is not a human-infectious virus and is easy to manipulate for both productive and latent infections in broad host cell lines in insects. This, with the general similarity of Hz-1 to the latent DNA viruses of mammals, i.e., differential viral gene expression, reactivation, and other characteristics makes Hz-1 virus system could serve as a good vector.

TABLE 1

Summary of luciferase activity driven by pag 1 promoters which were deleted in various 5'-leader sequence regions

| Constructs | Promoter region | Enzyme activity in SF9 (CPM/Q) |
|---|---|---|
| pGL2pag 1 | −728 - - - +1 | 137 ± 3 |
| pGL2pag 6 | −728 - - - +6 | 1445 ± 318 |
| pGL2pag 9 | −728 - - - +9 | 2494 ± 509 |
| pGL2pag 29 | −728 - - - +29 | 9752 ± 1039 |
| pGL2pag 198 | −728 - - - +198 | 3006 ± 80 |
| pGL2Basic | non | 82 ± 11 |

TABLE 2

Characteristics of the cells persistently infected with Hz-1 virus

| Characteristics | Cells | | | | |
|---|---|---|---|---|---|
| | TNP1 | TNP2 | TNP3 | SFP2 | SFP4 |
| Spontaneous reactivation* | | | | | |
| 1. | 210 ± 90 | 32 ± 8 | 21 ± 6 | 21 ± 8 | — |
| 2. | 0 | 0 | 0 | 0 | 81 ± 11 |
| Titers of virus** | | | | | |
| 1. | $8.2 \times 10^4$ | $4.4 \times 10^3$ | $2.6 \times 10^3$ | $1.4 \times 10^2$ | — |
| 2. | 0 | 0 | 0 | 0 | $5.2 \times 10^3$ |
| Viral DNA content in hosts | | | | | |
| 1. percentage | 12.0% | 0.8% | 16.4% | 0.1% | 0.4% |
| 2. Copies of viral genome/cell | 4068 | 137 | 2570 | 16 | 68 |

*Rates of spontaneous reactivation detected per $1 \times 10^5$ cells of TNP1, TNP2, TNP3, and SFP2 at 1. 30th-passage, and 2. at 200–230th-passages. SFP4, a newly established persistently infected cells, at 30th-passage.
**Titers of virus (pfu/ml/48 h) released into the media of TNP1, TNP2, TNP3, and SFP2 at 1. 30th-passage, and 2. at 200–230th-passages. SFP4, a newly established persistently infected cells, at 30th-passage.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

Abernathy, E. S., C. N. Wang, and T. K. Frey. 1990. Effect of antiviral antibody on maintenance of long-term rubella virus persistent infection in vero cells. J. Virol. 64:5183–5187.

Adams, R. H., and D. T. Brown. 1985. BHK cells expressing Sindbis virus-induced homologous interference allow the translation of nonstructural genes of superinfecting virus. J. Virol. 54:351–357.

Ahmed, R. and J. G. Stevens. 1991. Viral persistence. In Fields Virology 2nd ed. Field, B. N. and D. M. Knipe, editors. Raven Press, New York., pp241–266.

Anderson-Anvret, M., and T. Lindahl. 1978. Integrated viral DNA sequences in Epstein-Barr virus-converted human lymphoma lines. J. Virol. 25:710–718.

Askew, D. S., J. Li, and J. N. Ihle. 1994. Retroviral insertions in the murine His-I locus activate the expression of a novel RNA that lacks an extensive open reading frame. Mol. Cell. Biol. 14:1743–1751.

Baichwal, V. R., and B. Sugden. 1988. Latency comes of age for herpesviruses. Cell 52:787–789.

Blissard, G. W., and G. F. Rohrmann. 1990. Baculovirus diversity and molecular biology. Annu. Rev. Entomol. 35:127–155.

Block, T. M., J. G. Spivack, I. Steiner, S. Deshmane, M. T. McIntosh, R. P. Lirette, and N. W. Fraser. 1990. A herpes simplex virus type 1 latency-associated transcript mutant reactivates with normal kinetics from latent infection. J. Virol. 64:3417–3426.

Bloom, D. C., G. B. Devi-Rao, J. M. Hill, J. G. Stevens, and E. K. Wagner. 1994. Molecular analysis of herpes simplex virus type 1 during epinephrine-induced reactivation of latently infected rabbits in vivo. J. Virol. 68:1283–1292.

Briese, D. T. 1986. Insect resistance to Baculoviruses. In The Biology of Baculovirus, Vol. II. R. R. Granados, and B. A. Federici editors. CRC Press. New York., pp237–265.

Brannan, C. I., E. C. Dees, and S. D. M. Brown. 1990. The product of the H19 gene may functional as an RNA. Mol. Cell. Biol. 10:28–36.

Brockdorff, N., A. Ashworth, F. K. Graham, V. M. McCabe, D. P. Norris, P. J. Cooper, S. Swift, and S. Rastan. 1992. The product of the mouse Xist gene is a 15 kb inactive X-specific transcript containing no conserved ORF and located in the nucleus. Cell 71:515–526.

Brown, C. J. B. D. Hendrich, J. L. Rupert, R. G. Lafreniere, Y. Xing, J. Lawrence, and H. F. Willard. 1992. The human XIST gene: Analysis of a 17 kb inactive X-specific RNA that contains conserved repeats and is highly localized within the nucleus. Cell 71:527–542.

Burand, J. P., H. A. Wood., and M. D. Summers. 1983. Defective particles from a persistent Baculovirus infection in *Trichoplusia ni* tissue culture cells. J. Gen. Virol. 64:391–398.

Burand, J. P., C. Y. Kawanishi, and Y. S. Huang. 1986. In The Biology of Baculovirus, Granados, R. R., and B. A. Federici eds., CRC Press Inc. Boca Raton, Fla. Persistent Baculovirus infections, pp 159–175.

Burand, J. P., H. A. Wood., and M. D. Summers. 1983. Defective particles from a persistent Baculovirus infection in *Trichoplusia ni* tissue culture cells. J. Gen. Virol. 64:391–398.

Calzone, F. J., J. J. Lee, R. J. Britten, and E. H. Davidson. 1988. A long, nontranslatable poly(A) RNA stored in the egg of the sea urchin *Stronglyocentrotus purpuratus*. Genes & Devel. 2: 305–318.

Chao, Y. -C., S. Y. Young, K. S. Kim, and H. A. Scott. 1985. A newly isolated densonucleosis virus from *Pseudoplusia includens* (Lepidoptera: Noctuidae). Journal of Invertebrate Pathology 46:70–82.

Chao, Y.-C., S. Y. Young, and K. S. Kim. 1986. Characterization of a picornavirus isolated from *Pseudeplusia includens* (Lepidoptera: Noctuidae). J. Invertebr. Pathol. 47:247–257.

Chao, Y.-C. and Wood, H. A. 1990. The physical map of Hz-1 Baculovirus genome from standard and defective interference viral particles. J. of Gen. Virol. 71:1265–1270.

Chao, Y.-C., S. S. Sheu, M. C. Chang, C. Y. Chang, C. W. Chen, H. C. Weng, Y. C. Lin, and H. D. Lin. 1990. Investigation of viral persistent infections using Hz-1 Baculovirus as a model system. Bulletin of the Institute of Zoology, Academia Sinica, Monograph 15:33–47.

Chao, Y.-C., Wood, H. A., Chang, C. Y., Lee, H. T., and Lee, H. R. 1992. Differential Gene Expressions of Hz-1 Baculovirus During Viral Productive and Persistent Infections. J. Virol. 66:1442–1448.

Chazenbalk, G. D., and B. Rapoport. 1995. Expression of the extracellular domain of the thyrotropin receptor in the baculovirus system using a promoter active earlier than the polyhedrin promoter. Implications for the expression of functional highly glycosylated proteins. J. Biol. Chem. 27:1543–1549.

Chen, E. Y. and P. H. Seeburg. 1985. Supercoil sequencing: a fast and simple method for sequencing plasmid DNA. DNA 4:165–170.

Chisholm, G. E., and Henner, D. J. (1988). Multiple early transcripts and splicing of the *Autographa californica* nuclear polyhedrosis virus IE-1 gene. J. Virol. 62:3193–3200.

Condreay, L. D., and D. T. Brown. 1986. Exclusion of superinfecting homologous virus by Sindbis virus-infected *Aedes albopictus* (mosquito) cells. J. Virol. 58:81–86.

Costantini, F. D., R. J. Britten, and E. H. Davidson. 1980. Message sequences and short repetitive sequences are interspersed in sea urchin egg poly(A)+RNAs. Nature 287:111–117.

Dobson, A. T., F. Sederati, G. Devi-Rao, W. M. Flanagan, M. J. Farrell, J. G. Stevens, E. K. Wagner, and L. T. Feldman. 1989. Identification of the latency-associated transcript promoter by expression of rabbit beta-globin MRNA in mouse sensory nerve ganglia latently infected with a recombinant herpes simplex virus. J. Virol. 63:3844–3851.

Evans, H. F. 1986. Ecology and epizootiology of Baculovirus. In The Biology of Baculovirus, Vol. II. R. R. Granados, and B. A. Federici editors. CRC Press. New York, 1986., pp89–132.

Fini, M. E., W. G. Bendena, M. L. Pardue. 1989. Unusual behavior of the cytoplasmic transcript of hsr omega: An abundant, stress-inducible RNA that is translated but yields no detectable protein product. J. Cell Biol. 108:2045–2057.

Fraser, N. W., M. I. Muggeridge, D. M. Mellerick, and D. L. Rock. 1984. Molecular biology of HSV-1 latency in a mouse model system. In UCLA Symposia on Molecular and Cellular Biology New Series, Vol. 21, Herpesvirus. F. Rapp ed. Alan R. Liss, Inc, New York., pp159–173.

Fraser, N. W., A. M. Deatly, D. M. Mellerick, M. Muggeridge, and J. G. Spivack. 1986. Molecular biology of latent HSV-1. In Human Herpesvirus Infections. Lopez, C., and B. Roizman, editors. Raven Press, New York., pp39–54.

Fritz, J. D., M. L. Greaser, and J. A. Wolff. 1991. A novel 3' extension technique using random primers in RNA-PCR. Nucl. Acids Res. 19:3747.

Garcia-Blanco, M. A. and B. R. Cullen. 1991. Molecular basis of latency in pathogenic human viruses. Science 254:815–820.

Gardella, T., P. Medveczky, T. Sairenji, and C. Mulder. 1984. Detection of circular and linear herpesvirus DNA molecules in mammalian cells by gel electrophoresis. J. Virol. 50:248–254.

Granados, R. R., Nguyen, T., and Cato, B. 1978. An insect cell line persistently infected with a Baculovirus-like particle. Intervirol. 10:309–317.

Guarino, L. A., Smith, G., and Dong, W. 1995. Ubiquitin is attached to membranes of Baculovirus particles by a novel type of phosphokipid anchor. Cell 80:301–309.

Han, K., M. S. Levine, and J. L. Manley. 1989. Synergistic activation and repression of transcription by Drosophila homeobox proteins. Cell 56:573–583.

Harris, A., and D. R. Bentley. 1988. Separation of episomal Epstein-Barr virus from Burkitt's lymphoma host cell DNA in pulse field gels. Nucleic Acids Res. 16:4172.

Henderson, A., S. Ripley, M. Heller, and E. Kieff. 1983. Chromosome site for Epstein-Barr virus DNA in a Burkitt tumor cell line and in lymphocytes growth-transformed in vitro. Proc. Natl. Acad. Sci. USA 80:1987–1991.

Henikoff, S. 1984. Unidirectional digestion with exonuclease III creates targeted breakpoints for DNA sequencing. Gene 28:351–359.

Hills, D., and Crane-Robinson, C. 1995. Baculovirus expression of human basic fibroblast growth factor from a synthetic gene: role of the Kozak consensus and comparison with bacterial expression. Biochim. Biophys. Acta 1260:14–20.

Hink, W. F. 1970. Established insect cell line from the cabbage looper, *Trichoplusia ni*. Nature 226:466–467.

Ho, D. Y., and E. S. Mocarski. 1989. Herpes simplex virus latent RNA (LAT) is not required for latent infection in the mouse. Proc. Natl. Acad. Sci. USA 86:7596–7600.

Huang, Y. S., M. Hedberg, and C. Y. Kawanishi. 1982. Characterization of the DNA of a nonoccluded Baculovirus, Hz-1 V. J. Virol. 43:174–181.

Hughes, D. S., R. D. Possee, and L. A. King. 1993. Activation and detection of a latent Baculovirus resembling *Mamestra brassicae* nuclear polyhedrosis virus in *M. brassicae* insects. Virology 194:608–615.

Hurley, E. A., S. Agger, J. A. Mcneil, J. B. Lawrence, A. Calendar, G. Lenoir, and D. A. Thorley-Lawson. 1991. When Epstein-Barr virus persistently infects B-cell lines, it frequently integrates. J. Virol. 65:1245–1254.

Jacks, T., and H. E. Varmus. 1985. Expression of the *Rous sarcoma* virus pol gene by ribosomal frameshifting. Science 230:1237–1242.

Jurkovicoba, M. 1979. Activation of latent infections in larvae of *Adoxophyes orana* (Lepidoptera: Torticidae) and *Barathra brassicae* (Lepidoptera: Noctuidae) by foreign polyhedra. J. Invertebr. Pathol. 34:213–215.

Kay, G. F., G. D. Penny, D. Patel, A. Ashworth, N. Brockdorff, and S. Rastan. 1993. Expression of Xist during mouse development suggests a role in the initiation of X chromosome inactivation. Cell 72:171–182.

Kidd, M. and Emery, V. C. 1993. The use of Baculoviruses as expression vectors. App. Biochem. Biotechnol. 42:137–159.

Kimelman, D., M. W. Kirschner. 1989. An antisense MRNA directs the covalent modification of the transcript encoding fibroblast growth factor in Xenopus oocyte. Cell 59:687–696.

Klein, G. 1989. Viral latency and transformation: the strategy of Epstein-Barr virus. Cell 58:5–8.

Knight, P. 1991. Baculovirus vectors for making proteins in insect cells. ASM News 57:567–570.

Knutson, J. C. and B. Sugden. 1989. Immortalization of B lymphocytes by Epstein-Barr virus: What does the virus contribute to the cell? Adv. Vir. Oncol. 8:151–172.

Laakkonen, P., Hyvonen, M., Peranen, J., and Kaariainen, L. 1994. Expression of Semliki Forest virus nsP1-specific methyltransferase in insect cells and in *Escherichia coli*. J. Virol. 68:7418–7425.

Lee, J. C., H. H. Chen, H. L. Wei, and Y. C. Chao. 1993. Superinfection-induced apoptosis and its correlation with the reduction of viral progeny in cells persistently infected with Hz-1 Baculovirus. J. Virol. 67:6989–6994.

Lee, S. T., S. M. Yu, E. L. Hsu, and Y. C. Chao. 1995. Identification of a very early promoter of insect of Hz-1 virus using a novel dual-expression shuttle vector. Nucleic Acids Res. 23:4683–4689.

Lee, S. E. and G. Brawerman. 1971. Pulse labelled ribonucleic acid complexes released by dissociation of rat liver polysomes. Biochemistry 10:510–516.

Leist, T. P., R. M. Sandri-Goldin, and J. G. Stevens. 1989. Latent infections in spinal ganglia with thymidine kinase-deficient herpes simplex virus. J. Virol. 63:4976–4978.

Leib, D. A., C. L. Bogard, M. Kosz-Vnenchak, K. A. Hicks, D. M. Coen, D. M. Knipe, and P. A. Schaffer. 1989. A deletion mutant of the latency-associated transcript of herpes simplex virus type 1 reactivates from the latent state with reduced frequency. J. Virol. 62:2893–2900.

Levene, S. D., and Zimm, B. H. 1987. Separation of open-circular DNA using pulse-field gel electrophoresis. Proc. Natl. Acad. Sci. USA 84:4054–4057.

Liebovitch, M. P., V. C. Nguyen, M. S. Gross, B. Solhonne, S. A. Liebovitch, and A. Bernheim. 1991. The human ASM (adult skeletal muscle) gene: expression and chromosomal assignment to 11p15. Biochem. Biophys. Res. Commun. 180:1241–1250.

Lindahl, T., A. Adams, G. Bjursell, and G. W. Bornkamm. 1976. Covalently closed circular duplex DNA of Epstein-Barr virus in a human lymphoid cell line. J. Mol. Biol. 102:511–530.

Longworth, J. F. and J. C. Cunningham. 1968. The activation of occult nuclear polyhedrosis virus by foreign nuclear polyhedra. J. Invertebr. Pathol. 10:361–367.

Luckow, V. A. 1991. Cloning and expression of heterologous genes in insect cells with Baculovirus vectors, p. 97–151. In A. Prokop, R. K. Bajpai, and C. Ho. (ed.), Recombinant DNA technology and applications. McGraw-Hill, Inc., New York.

McIntosh, A. H. and C. M. Ignoffo. 1981. Establishment of a persistent Baculovirus infection in a lepidopteran cell line. J. Invertebr. Pathol. 38:395–403.

Mellerick, D. M., and N. W. Fraser. 1987. Physical state of the latent herpes simplex virus genome in a mouse model system: evidence suggesting an episomal state. Virology 158:265–275.

Metzenberg, S. 1990. Levels of Epstein-Barr virus DNA in lymphoblastoid cell lines are correlated with frequencies of spontaneous lytic growth but not with levels of expression of EBNA-1, EBNA-2, or latent membrane protein. J. Virol. 64:437–444.

Miller, L. K. 1988. Baculoviruses as gene expression vectors. Ann. Rev. Microbiol. 42:177–199.

Nowak, R. 1994. Mining treasures from junk DNA. Science 263:608–610.

O'Reilly, D. R., L. K. Miller, and V. A. Luckow. 1992. Baculovirus expression vectors, a laboratory manual. W. H. Freeman and Company, New York., p347.

Oldstone, M. B. 1989. Viral persistence. Cell 56:517.

Openshaw, H., L. V. S. Asher, C. Wohlenberg, T. Sekizawa, and A. L. Notkins. 1979. Acute and latent infection of sensory ganglia with herpes simplex virus: Immune control and virus reactivation. J. Gen. Virol. 44:205–215.

Podgwaite J. D., and H. K. Mazzone. 1986. Latency of insect viruses. Adv. Virus Res. 31:293–320.

Poirier, F., C. T. J. Chan, P. M. Timmons, E. J. Robertson, M. J. Evans, and P. W. J. Rigby. 1991. The murine H19 gene is activated during embryonic stem cell differentiation in vitro and at the time of implantation in the developing embryo. Development 113:1105–1114.

Possee, R. D., S. C. Howard. 1987. Analysis of the polyhedrin gene promoter of the *Autographa californica* nuclear polyhedrosis virus. Nucleic Acids Research 15:10233–266.

Powell, L. M., S. C. Wallis, R. J. Pease, Y. H. Edwards, T. J. Knott, and J. Scott. 1987. A novel form of tissue-specific RNA processing produces apolipoprotein-B48 in intestine. Cell 50:831–840.

Ralston, A. L., Y. Huang, and C. Y. Kawanishi. 1981. Cell culture studies with the IMC-Hz-1 nonoccluded virus. Virology 115:33–44.

Riedel, B., and D. T. Brown. 1979. Novel antiviral activity found in the media of sindbis virus-persistently infected mosquito (*Aedes algopictus*) cell cultures. J. Virol. 29:51–60.

Rowe, D. T., L. Hall, I. Joab, and L. Gerhard. 1990. Identification of the Epstein-Barr virus terminal protein gene products in latently infected lymphosytes. J. Virol. 64:2866–2875.

Schmidt, E. E., and G. F. Merrill. 1991 Changes in dihydrofolate reductase (DHFR) MRNA levels can account fully for changes in DHFR synthesis rates during terminal differentiation in a highly amplified myogenic cell line. Mol. Cell. Biol. 11:3726–3734.

Silins, S. L., V. P. Argaet, and T. B. Sculley. 1992. Isolation of Epstein-Barr virus genomes using pulse-field gel electrophoresis. Nucleic Acids Res. 20:2901.

Smith, C. L., J. G. Econome, A. Schutt, S. Klco, and C. R. Cantor. 1987. A physical map of the *Escherichia coli* K12 genome. Science 236:1448–1453.

Smith, G. S., Summers, M. D., and Fraser, M. J. 1983. Production of human beta interferon in insect cells infected with a Baculovirus expression vector. Mol. Cell. Biol. 3:2156–2165.

Spivack, J., and N. W. Fraser. 1987. Detection of herpes simplex virus type 1 transcripts during latent infection in mice. J. Virol. 61:3841–3847.

Steiner, I., J. G. Spivack, R. P. Lirette, S. M. Brown, A. R. McLean, J. H. Subak-Sharpe, and N. W. Fraser. 1989. Herpes simplex virus type 1 latency associated transcripts are evidently not essential for latent infection. EMBO J. 8:505–511.

Stevens, J. G., E. K. Wagner, G. B. Devi-Rao, M. L. Cook, and L. T. Feldman. 1987. RNA complementary to a herpesvirus gene MRNA is prominent in latently infected neurons. Science 235:1056–1059.

Summers, E. and M. D. 1982. DNA homology among subgroup A, B, and C Baculoviruses. Virology 123:393–406.

Summers, M. D. and G. E. Smith. 1988. A manual of methods for Baculovirus vectors and insect cell culture procedures. Texas Agricultural Experiment Station Bulletin No. 1555.

Tabor, S., and C. C. Richardson. 1987. DNA sequence analysis with a modified bacteriophage T7 DNA polymerase. Proc. Natl. Acad. Sci. U.S.A. 84:4767–4771.

Takayama, K. M., and M. Inouye. 1990. Antisense RNA. Crit. Rev. Biochem. 25:155–184.

Templeton, D. and W. Eckhart. 1984. N-terminal amino acid sequences of the polyoma middle-size T antigen are important for protein kinase activity and cell transformation. Mol. Cell. Biol. 4:817–21.

Teo, G., and B. E. Griffin. 1987. Epstein-Barr virus genomes in lymphoid cells: Activation in mitosis and chromosomal location. Proc. Natl. Acad. Sci. USA 84:8473–8477.

Van Den Berg, F. M., M. Jiwa, R. Rook, and J. L. Geelen. 1988. Analysis and isolation of cytomegalovirus DNA by field inversion gel electrophoresis. J. Gen. Virol. 69:699–704. Volkman, L. E. 1995. Virus Taxonomy: the classification and nomenclature of viruses. In The sixth report of the ICTV. Springer-Verlag, Vienna. In press.

Weigel, R. and G. Miller. 1983. Major EB virus-specific cytoplasmic transcripts in a cellular clone of the HR-1 Burkitt lymphoma line during latency and after induction of viral replicative cycle by phorbol esters. Virology 125:287–298.

Wilkinson, G. W. G. and A. Akrigg. 1992. Constitutive and enhanced expression from the CMV major IE promoter in a defective adenovirus vector. NUCLEIC ACIDS RES. 20:2233–2239.

Wilson, M. 1991. The family and groups of Baculoviridae. In Classification and nomenclature of viruses. Fifth report of the International Committee on Taxonomy of Viruses. Archives of Virology Supplementum 2. P117–123. Francki, R. I. B., Fauquet, C. M., Knudson, D. L., and Brown, F. eds. Springer-Verlag Wien, Inc., New York.

Wood, H. A., and J. P. Burand. 1986. Persistent and productive infections with the Hz-1 Baculovirus. In Current Topics in Microbiology and Immunology Vol. 131, The Molecular Biology of Baculovirus. Doefler, W. and P. Bohm, editors. Springer-Verlag. Berlin Heidelberg., pp119–134.

Zwaagstra, J. C., H. Ghiasi, S. M. Blanina, A. B. Nesburn, S. C. Wheatley, K. Lillycrop, J. Wood, D. S. Latchman, K. Patel, and S. L. Wechsler. 1990. Activity of herpes simplex virus type 1 latency-associated transcript (LAT) promoter in neuron-derived cells: evidence for neuron specificity and for a large LAT transcript. J. Virol. 64:5019–5028.

---

What is claimed is:

1. An isolated nucleic acid molecule which has a nucleotide sequence coding for Hz-1 pag1 promotor and having a sequence of bases 1 to 1095 of FIG. 1B (SEQ ID NO: 1).

2. An isolated nucleic acid molecule which has a nucleotide sequence coding for a functional portion of Hz-1 pag1 promoter and having the sequence of any of bases −728 to +1, −728 to +6, −728 to +9, −728 to +29, −728 to +198, −727 to +29, −607 to +29, −493 to +29, −403 to +29, −42 to +29, −14 to +29, and 0 to +29 of the nucleotide sequence of pag1 as set forth in FIG. 1B (SEQ ID NO: 1), wherein base 1066 is counted as +1.

3. An isolated nucleic acid molecule which has a nucleotide sequence coding for a functional portion of Hz-1 pag1 promoter and having a sequence of bases 976 to 1095 of FIG. 1B (SEQ ID NO:1).

4. An insect cell line infected with a Nuclear Polyhedrosis Virus containing the nucleic acid molecule as claimed in any one of claims 1, 2, or 3.

5. A vector containing the isolated nucleic acid of any of claims 1, 2, or 3.

6. The vector of claim 5 wherein the vector is Hz-1 virus.

7. A method for expressing a gene product in a cell cultured in vitro comprising introducing into the cell the vector of claim 5 and culturing said cell so as to express said gene product.

8. A cell containing the vector of claim 6.

9. The vector of claim 5 wherein the vector is a Baculovirus.

10. A method for expressing a cytocidal gene product in a cell cultured in vitro comprising introducing into the cell the vector of claim 9, wherein there is expressing of said cytocidal gene and a cytocidal effect therefrom.

11. A method for expressing a gene product in a cell cultured in vitro comprising introducing into the cell the vector of claim 7 and culturing said cell so as to express said gene product.

12. A cell containing the vector of claim 9.

13. The vector of claim 7 further comprising exogenous coding DNA operably linked to the Hz-1 PAG1 promoter or the functional portion thereof.

14. An insecticidial or pesticidal comprising the vector as claimed in claim 13 in admixture with a suitable carrier.

15. A cell containing the vector of claim 13.

16. A method for expressing a gene product comprising introducing into a cell the vector or claim 13, and culturing said cell so as to express said gene product.

17. The method of claim 16 wherein the cell is not a natural host of the vector.

18. An insecticidial or pesticidal comprising the gene product from the method as claimed in claim 16 in admixture with a suitable carrier.

19. The method of claim 16 wherein there is expression of the gene product and a cytocidal effect therefrom.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 4286 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GGTACCAGAC TATGGTGCCA GACTTTCAGA CATCATCTTT CCAGACTTTA CTCATTCAAA      60

TCATCTTTAT ACATTCACAT TCAAATCATC TCTCTACATC CATATTCAAA TTATTCTATT     120
```

-continued

| | |
|---|---|
| CATCCTCTCT CAACATCACC CCTCGTAGAC CTAAGTTTTC ATCACGTCTA CTTTTAAAAT | 180 |
| AAACACGGAC TATACTTGTA ATTAAATATT AAACAATTGT AATTTAGTAT TAAATAATTT | 240 |
| AGTATTGAAC AATCTCTATA TACATAATCG TCTACATTTG AGGTTATAAA ACGTTGTATG | 300 |
| CAAAATTGAA AATTGACACA GTTACCCCTC GCGCAGAGTC CCGGCTATGC GCAAGAGTGT | 360 |
| AGTTTAAAGT GTCTGGCTAC ATTTTAGCAT CAGTCAAATG TCTTGATTTG CATCTGAATT | 420 |
| GGTATAACCT CGATTGTAAA CAATGAACTG GGTGTGCACG TCGCCATCTT GTTGTGTTAA | 480 |
| TTTATTATGC ATGTTAATTT AAGCGTTTGT TTATAGCTTT ATACGTTGAA GATACATTCA | 540 |
| AAATTCATTC ACACGGTTAG AATAACGGTA TTGGAATCTA GAAACTAGAC CTTTAGGTCG | 600 |
| CAACAGACCC TCGGGACCGG TATAATTGTA GGCGTTTAAT TATTGTTATA AAAGGGTAGT | 660 |
| ATTTAATGTT GTAGCGAGCC GTCCAATGAC TGGCTATAGA CTAGACAACG CCAGAGACGG | 720 |
| GACAGATGCA TTGGATGCAT CAAAAGTGTA AAATTTAAAG AGCTAGCGGT AAAAATGATA | 780 |
| AAAAGTATAC AAATGTACAC TTTTAGGACA AACCAGAGTA CAGAGACACC ACATGTGAGG | 840 |
| TATCCCACAG ATGGTCTTGT GAAAAGGAGT CCAAAAATGT AAAAAAGAAT AATCATGTAG | 900 |
| AAGAATCATT AAGAGGAATC GTTCCCCCCG CAGAAGAATC TAGTAGGTGT GCACGTTTTT | 960 |
| CTGATAAAGT TTTATTACTC ATCGACCAAT GGCGTCGCTC GGTTCTTATC GCAACAGAGT | 1020 |
| GGGGGCCATC CGCACTATAA AAAGCCGAGA CTGGTGACGA ACACCATCAG TCTGATTCGA | 1080 |
| GTCGTGTTCA TACCGCACTG GTGTAGGCAG CGTCTGGTAC TAGGTGAGTG GCTCATTCTT | 1140 |
| ATTTAATTCA TTTAATTTGT CTGCTCTGTT TATTCAATTT TAAAATGTGC AGTCTCGGGT | 1200 |
| CATCTGATAC ACTTTTTATA GCTCTTAGCA TACTTAAATT TTATGGAGCG GAGTAATCGA | 1260 |
| CCCGAATCGG ACCTCGGTCT GGTACGAAAC GATAGCACTG CTCTTTGCCA AAACCAAACA | 1320 |
| CAACTCGCAT CTGATCCGCT CTGTGTTCGA GACATGTTGT CCGAATGTGT TCCTTAAAGG | 1380 |
| CGACATGCGA CCTTGTTGGT CACAAGCCAC TGCTCCTATG CAAACGGGTT CCTTTGGTTC | 1440 |
| GATTGTGTCG CACGAGTGGA TGCTAAATTC GCGTGCAGGT GTCGAGACTT AGACTTTTTA | 1500 |
| GGGAGTAGGT AGCATAGATG ACTCGGGCTG TCGCTTAACG TTGAATACGC AGGGTGGACT | 1560 |
| CTTTGAATGG ATTTTATTCA GATGCCACCT CGACTCGAAT CATACTGGTA CCCGTTTTGG | 1620 |
| CACTGTAGTA TCGGCAACGG TAATGCAGTG TCGAGACTTA AACTCTTGGT GGCACAGTGT | 1680 |
| ATAAACTGTA GGTTCTCTCT CTCGTTTATG AATAATGTTA TTATTCTACA TTAGTCTTAT | 1740 |
| CTGGCCCGGC ATGTACTAGG TAGGATGTTT TTATTATATA CACACATGTG CATTTGAGGA | 1800 |
| TAATAACAAT GGTAATGTGT GCGTGTCGGG CATCTATAAA TACACGTGTG CGTGTGTGCT | 1860 |
| GTTTTATTAT TATTAGGTAG GCGTAGCTTG CACATGTGCC ACCATAGGGA CTTTTAGTTT | 1920 |
| TGTTAGTGTA GTGTTTTTGA GTGCAAGATG TTTGTTTTTA CTGTGCATTT ACAAGAGACT | 1980 |
| TGATGGAACA CTTATATGTA GAACAGTACT ACTACTAGAG GATAGCGTTT AGTAGAGGTG | 2040 |
| CTGGGAACAA TAGTGTGCCG AGTATAATCA TAGGTATGTG TTGCAATACT TTTTATTTTA | 2100 |
| TGCTTTTACA TTTTATGGTT CATTACTTGA CACTGATTGA TATTTTATAC TTGTTGATAT | 2160 |
| TGTGTGGATA ATTTATGAGA TAATTTATGA CCATCTGTGG GAATCTAGGT AGGTAGGGTT | 2220 |
| TTACACATGC TTACACATAC ACACTGACAC TGACACACAT TTTACAAACC AAACCAAACA | 2280 |
| AAACAAAAGT ACATTAAAAC AAACGGAAAA CCAATACCAT ACATTCTATC ATTCTATCCT | 2340 |
| TCTACTATTA CTACCACTAT CTACTATGGG TACCTACCAA ACATTTTTAA ATCTATACAT | 2400 |
| ACACACATGG ATTTGTGCTC ACAACAACAA AACACAATCG GTTAGGGTCG TTGGGTCTGT | 2460 |
| TGCAGTCTCG GCAGCTTAGG TCGGTTAGTT TTAGGCTCGG TTAGTCTGTA AGCGGTACGG | 2520 |

```
CTAGTTTATA AGGCTCGGTT AGTTATAAGG TAGGCTCGGT TAGATATAAG GTTCGGTTAG    2580

CTATAAGTCG GTGCGGCTAG TTTATAAGTC CGGTTAGATT TAAGTGCGGC TAGTGTATAA    2640

GTCGGTGTGA GCACAAATCA ATAGATGTAG TAAGATGTGA TACTTTATGA ATTGAATTAT    2700

AAATTGATAC ACGACGGTAA ACAAGAGTTG ATTTGTGTAG TATACGTCTT CTTCTTCCTA    2760

CTTCCTACTA TTGCAAACAA TATAAAAAAA ACATATAAAA TAAAAACACG GGTTGTACAC    2820

ATTTACACAT ACACACTATA CACACCAATT TAGGGTTACG ATAATTTAGG ACATTTAGGA    2880

TAATGACAAA GTGTCTCTGG TAAAGACTGG TGGTAAGACT GGCATATACT GGTATATAAA    2940

TGCAAGGATA CAACTAGGTA CGGTACTCTG CAACTACTAT ACTCTGGTAT ACTCGGCAAA    3000

CTTTGTGTAC TCTGGTACTC TGATAAAGCT ATACTCTGGT AAATACTCTG GTAGAACTCT    3060

GTACTCTGAT ATACTCTGGT ACTTTTGTAC ATATACAACT ACAACAACAA ATCTGGTAAC    3120

TCGGTGACTC TGACTCTGGC GTCTCTTGGT AACTCTGGTG GTATTGGTAT TGGTTAATAA    3180

AGGTATCAAC GGTTTCAAAC AAAGGTATTG GTATCAAATA ACGGTATCAA AGGTATTACA    3240

CAAAGGTATT AAACAAAGGT ATTAAACAAA AGGTATCAAA CAATAGGTTT AGGCAAATGC    3300

ACACACATAA GTTAAGCACA CGTAGTAAAT GCACAGTACG TAGGGTGTCT AGTGCAGAAT    3360

TTGATACTAT GAGCGTTTCG GTTCGGTACC GTTTAAGAGG GCGTAGAGTC AAACCTTTGG    3420

CATGGTTTGT ATCGCATGCA ACACCAAAGC TAGTGGTGCA TGTTATGCTC TCCGTGCCTC    3480

ATATCCCAAT AATAACCAAC CCATCCCCAT ACAAGAGTTC ACTAACCATA CTCTAAATGG    3540

TATCGTATTG AAAGAGTTTG TTGTATTCAA TTCTTGCACA ATTCGTGTAG ATTAGAATGC    3600

AGCAAAAGTC TTGCACACCT AGGCGTGCGA TGCGATCGTT AGGCTCTGTG TACGAGTATC    3660

GCATTGCACA ACAACCCACT GACCAACCCC CTCGCACCGT CACGTTGTCT TTCAGGCAGT    3720

CTCTCGTGGC GTGTGCGCTT GTTTGCTTTG CAAAGAGATT GCCTTAGTGC CTTGTTGCAA    3780

CCGTGGCGTG CAAGTGTTTG AGTTGTGGAC ATATGCGATC GATTGCCTCG CAGTAATCGG    3840

CTACGATAAC GCTGCCTGGT ATCTCCGATG TACATTGTCG TTAACACACA AAAAACGTGC    3900

ACGCTCTTGC CAATTAACGT TAACGTAGAG TCAGTATTTT AATATTAAAA CGGTTTTTTT    3960

CTTTTTTTTT CACCACCCAA TAAACTAACA ATTACTGGTG ACATTTGTTG TTTCATTTTA    4020

TACATCCTGC ATCCTGATAC AACCTTTACA CGAACTGCTG TTAGGTAGAG TGTTTTATTA    4080

GGTAGAGTGT TTTGTTACAG TTAGGTAGAC TGTACTGTAG GCTGTTGTTG TGTGTTAGGT    4140

TTGATACAAA CATACAAATA TACAAATACA TAAAACCAGA GTTACCACTA GGGTTTGAGA    4200

CTATTATAGA GTTGTGATTG AGTATAGAGT TACTTTTTGA AGAGTATTGG TATTCTGAAG    4260

AGTATTGGTA TTCTACAAGT ATCCTG                                        4286
```

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
TCGGTTAGTT                                                            10
```

(2) INFORMATION FOR SEQ ID NO:3:

(i) SEQUENCE CHARACTERISTICS:

(A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AGGCTCGGTT AGTT                                                            14

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TAGGCTCGGT TAGT                                                            14

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TAGGCTCGGT TAG                                                             13

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGGCTAGTTT ATAAG                                                           15

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTGCGGCTAG TTTATAAG                                                        18

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TATAAGTCGG TG                                                    12

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TATAAGTCGG TG                                                    12

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTGCGGCTAG T                                                     11

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTCTGGTAAA                                                       10

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTATACTCTG GTA                                                   13

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TACTCTGGTA CTCTGATA                                              18

(2) INFORMATION FOR SEQ ID NO:14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTATACTCTG GTA        13

(2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATACTCTGGT A        11

(2) INFORMATION FOR SEQ ID NO:16:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTACTCTGAT A        11

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TATACTCTGG TACT        14

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TGGTATTGGT AT        12

(2) INFORMATION FOR SEQ ID NO:19:

(i) SEQUENCE CHARACTERISTICS:

```
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

TGGTATTGGT                                                              10

(2) INFORMATION FOR SEQ ID NO:20:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

AAAGGTATCA A                                                            11

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

AAACAAAGGT ATTGGTAT                                                     18

(2) INFORMATION FOR SEQ ID NO:22:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CAAAGGTATT A                                                            11

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

ACAAAGGTAT TAAACAAA                                                     18

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

-continued (ii) MOLECULE TYPE: DNA (genomic)

(xi) SEQUENCE DESCRIPTION: SEQ ID NO:24:

AAACAAAGGT ATTAAACAAA                                                    20

(2) INFORMATION FOR SEQ ID NO:25:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:25:

AAAGGTATCA AACAA                                                          15